(12) United States Patent
Rump et al.

(10) Patent No.: US 8,110,369 B2
(45) Date of Patent: Feb. 7, 2012

(54) METHODS, KITS, REAGENTS AND DEVICES FOR DETECTING MESOTHELIN AND/OR MEGAKARYOCYTE POTENTIATING FACTOR IN PERITONEAL FLUIDS

(75) Inventors: Armin Rump, Reading, MA (US); Yoshihiro Fujii, Nagano (JP)

(73) Assignee: Medical & Biological Laboratories Co., Ltd, Nagoya (JP)

( * ) Notice: Subject to any disclaimer, the term of this patent is extended or adjusted under 35 U.S.C. 154(b) by 286 days.

(21) Appl. No.: 12/488,139

(22) Filed: Jun. 19, 2009

(65) Prior Publication Data

US 2010/0022026 A1    Jan. 28, 2010

Related U.S. Application Data

(60) Provisional application No. 61/074,341, filed on Jun. 20, 2008.

(51) Int. Cl.
*G01N 33/53* (2006.01)
(52) U.S. Cl. .......................................... 435/7.1; 436/518
(58) Field of Classification Search .................. None
See application file for complete search history.

(56) References Cited

OTHER PUBLICATIONS

Breborowicz et al., "Limitations of CA125 as an Index of Peritoneal Mesothelial Cell Mass", Nephron Clin. Pract. 100:c46-c51, (2005).
Endemann et al., "Evidence for HSP-mediated cytoskeletal stabilization in mesothelial cells during acute experimental peritoneal dialysis", Am J Physiol Renal 292:47-56 (2007).
Fussholler et al., "Effluent CA 125 Concentration in Chronic Peritoneal Dialysis Patients: Influence of PD Duration, Peritoneal Transport and PD Regimen", Kidney Blood Press Res., 26:118-122 (2003).
Hermans et al., "Association of serum fetuin-A levels with mortality in dialysis patients" International Society of Nephrology, http://www.kidney-international.org, pp. 1-6 (2007).
Hirahara et al., "The potential of matrix metalloproteinase-2 as a marker of peritoneal injury, increased solute transport, or progression to encapsulation peritoneal sclerosis during peritoneal dialysis—a multicentre study in Japan", Nephrol Dial Transplant, 22:560-567 (2007).
Iwahori et al., "Megakaryocyte potentiating factor as a tumor marker of malignant pleural mesothelioma: Evaluation in comparison with mesothelin", Lung Cancer pp. 1-10 (2003).
"An overview of regular dialysis treatment in Japan" Japanese Society for Dialysis Therapy pp. 1-43, Dec. 31, 2005.
Kim et al., "Low glucose degradation products dialysis solution modulates the levels of surrogate markers of peritoneal inflammation, integrity, and angiogenesis: preliminary report" Nephrology, 8, S28-S32 (2003).
Kojima,et al., "Molecular cloning and expression of Megakaryocyte potentiating factor cDNA", The Journal of Biological Chemistry, vol. 270, No. 37, Issue of Sep. 15, pp. 21984-21990 (1995).
Otsuka, et al., "Restoration of peritoneal integrity after withdrawal of peritoneal dialysis: characteristic features of the patients at risk of encapsulating peritoneal sclerosis" Clin Exp Nephrol, 9:315-319 (2005).
Scholler et al., "Soluble member(s) of the mesothelin/megakaryocyte potentiating factor family are detectable in sera form patients with ovarian carcinoma" Proc. Natl. Acad. Sci. USA, vol. 96, pp. 11531-11536 (1999).
Witowski et al., "Peritoneal dialysis with solutions low in glucose degradation products is associated with improved biocompatibility profile towards peritoneal mesothelial cells" Nephrol Dial Transplant, 19:917-924 (2004).

*Primary Examiner* — Jacob Cheu
(74) *Attorney, Agent, or Firm* — Lando & Anastasi, LLP

(57) ABSTRACT

Certain embodiments disclosed herein are directed to methods and kits for detecting and quantifying in patient peritoneal fluid, such as spent peritoneal dialysis buffer, peptides having amino acid sequences related to megakaryocyte potentiating factor. The methods and kits can be used to monitor the biological status of the mesothelial lining of the peritoneal cavity in a patient, to predict development of a pathology of the mesothelium in an otherwise asymptomatic patient, and/or to assess the risk and suitability of a therapeutic method. In particular, the method can be used to assess negative effects of peritoneal dialysis on the biological integrity of the peritoneum, and thus to determine the time point when peritoneal dialysis treatment should be discontinued in favor of hemodialysis in a patient with kidney dysfunction, in order to avoid the development of peritoneal hypertrophy and other progressive mesothelial disorders such as encapsulating peritoneal sclerosis.

5 Claims, 16 Drawing Sheets

SRTLAGETGQEAAPLDGVLANPPNISSLSPRQLLGFPCAEVSGLS
TERVRELAVALAQKNVKLSTEQLRCLAHRLSEPPEDLDALPLDLL
LFLNPDAFSGPQACTRFFSRITKANVDLLPRGAPERQRLLPAALAC
WGVRGSLLSEADVRALGGLACDLPGRFVAESAEVLLPRLVSCPGP
LDQDQEAARAALQGGGPPYGPPSTWSVSTMDALRGLLPVLGQP
IIRSIPQGIVAAWRQRSSSRDPSWRQPERTILRPRFRR

SEQ ID NO: 1

EVEKTACPSGKKAREIDESLIFYKKWELEACVDAALLATQMDRVNAIP
FTYEQLDVLKHKLDELYPQGYPESVIQHLGYLFLKMSPEDIRKWNVTS
LETLKALLEVNKGHEMSPQAPRRPLPQVATLIDRFVKGRGQLDKDTLD
TLTAFYPGYLCSLSPEELSSVPPSSIWAVRPQDLDTCDPRQLDVLYPK
ARLAFQNMNGSEYFVKIQSFLGGAPTEDLKALSQQNVSMDLATFMKL
RTDAVLPLTVAEVQKLLGPHVEGLKAEERHRPVRDWILRQRQDDLDTL
GLGLQGGIPNGYLVLDLSMQEALS

SEQ ID NO: 2

FIG. 1

Anti-MPF Clone 20-10 Heavy Chain

```
        signal sequence                                                              FR1
1    ATGGGATGGAGCGGGGTCTTTCTCTTCTTGGCAGCAACAGCTACAGGTGTCCACTCCCAGGTCCAACTGCAGCAGTCTGGGCCTGAACTG          90
     M   G   W   S   G   V   F   L   F   L   A   A   T   A   T   G   V   H   S   Q   V   Q   L   Q   Q   S   G   P   E   L
                                                                              CDR1                                FR2
91   GTGAGGCCTGGGCTTCAGTGAAGATGTCCTGCAAGGCTTCAGGCTATACCTTCACA ACTACTGGATGCAC TGGGTGAGACAGAGGCCT         180
     V   R   P   G   A   S   V   K   M   S   C   K   A   S   G   Y   T   F   T   T   Y   W   M   H   W   V   R   Q   R   P
                                                   CDR2                                                          FR3
181  GGACAAGGCCTTGAGTGGATTGG  GTGATTGATCCTTCCAATAATGATTCTAAATTAAACCAGAAGTTCAACGAT AAGGCCTCATTGACT         270
     G   Q   G   L   E   W   I   G   V   I   D   P   S   N   N   D   S   K   L   N   Q   K   F   N   D   K   A   S   L   T
                                                                                                 CDR3
271  GTAGACACATCCTCCAACACAGCCTACATGCAGCTGAGCAGCCTGACATCTGAGGACTCTGCAGTCTATTACTGTGCAAGA CGACTGGTT         360
     V   D   T   S   S   N   T   A   Y   M   Q   L   S   S   L   T   S   E   D   S   A   V   Y   Y   C   A   R   R   L   V
                    FR4                                                      CH1
361  TACTATGCTATGGACTCC TGGGGTCAAGGAACCCCAGTCACCGTCTCCTCA GCCAAAACGACACCCCCATCTGTCTATCCACTGGCCCCT        450
     Y   Y   A   M   D   S   W   G   Q   G   T   P   V   T   V   S   S   A   K   T   T   P   P   S   V   Y   P   L   A   P 451  GGATCTGCTGCCCAAACTAACTCCATGGTGACCCTGGTGTCCTGCCTGGTGCTGGGCCTGTACTCCCTGAGCCAGTGACCTGGAACTCT         540
     G   S   A   A   Q   T   N   S   M   V   T   L   G   C   L   V   K   G   Y   F   P   E   P   V   T   V   T   W   N   S 541  GGATCCCTGTCCAGCGGTGTGCACACCTTCCCAGCTGTCCTGCAGTCTGACCTCTACACTCTGAGCAGCTCAGTGACTGTCCCCTCCAGC         630
     G   S   L   S   S   G   V   H   T   F   P   A   V   L   Q   S   D   L   Y   T   L   S   S   S   V   T   V   P   S   S 631  ACCTGGCCCAGCGAGACCGTCACCTGCAACGTTGCCCACCCGGCCAGCAGCACCAAGGTGGACAAGAAAATTGGATCCAGATCTGCGG          718
     T   W   P   S   E   T   V   T   C   N   V   A   H   P   A   S   S   T   K   V   D   K   K   I   G   S   R   S   A
```

FIG. 2

SEQ ID NO: 5 and SEQ ID NO: 14

Anti-MPF Clone 20-10 Light Chain

```
        signal sequence                                                              FR1
    1   ATGAGTGTGCTCACTCAGGTCCTGGCGTTGCTGCTGTGCTGTTACAGACGCAGGATGTGACATCCAGATGACTCAGTCTCCAGCCTCC   90
        M  S  V  L  T  Q  V  L  A  L  L  L  W  L  T  D  A  G  C  D  I  Q  M  T  Q  S  P  A  S
                                                                                                    FR2
                                                       CDR1
   91   CTGGCTGCATCTGTGGGAGAAACTGTCACCATCACATGTCGAGCAAGTGAGAACATTTACTACAGTTTAACATGGTATCAGCAGAAGCAA  180
        L  A  A  S  V  G  E  T  V  T  I  T  C  R  A  S  E  N  I  Y  Y  S  L  T  W  Y  Q  Q  K  Q
                                                                                FR3
                    CDR2
  181   GGGAGATCCTCAGCTCCTGATCTATAATGCAATCAACTTGGAAGATGGTGTCCCATCGAGGTTCAGTGGCAGTGGATCTGGACACAG    270
        G  R  S  P  Q  L  L  I  Y  N  A  I  N  L  E  D  G  V  P  S  R  F  S  G  S  G  S  G  T  Q
                                                                                     FR4
                                        CDR3
  271   TTTTCTATGAAGATCAACAGCATGCAGCCTGAAGATTCCGCAACTTATTTCTGTAAACAGGCTTATGACGTTCCATTCACGTTCGGCTCG  360
        F  S  M  K  I  N  S  M  Q  P  E  D  S  A  T  Y  F  C  K  Q  A  Y  D  V  P  F  T  F  G  S
                    CL1
  361   GGGACAAAGTTGGAAATAAAACGGGCTGATGCTGCACCAACTGTATCCATCTTCCCACCATCCAGT   426
        G  T  K  L  E  I  K  R  A  D  A  A  P  T  V  S  I  F  P  P  S  S
```

FIG. 3

SEQ ID NO: 6 and SEQ ID NO: 15

Anti-MPF Clone 41-28 Heavy Chain signal sequence → FR1

```
  1 ATGGCTTGGGTGTGGACCTTGCTATTCCTGATGGCAGCTGCCAAAGTGCCCAAGCACAGATGCCAAAGTGCCCAGCAGATCCAGTTGGTGCAGTCTGGACCTGAGCTG   90
    M   A   W   V   W   T   L   L   F   L   M   A   A   A   Q   S   A   Q   A   Q   I   Q   L   V   Q   S   G   P   E   L
                                                                                                            FR2
                                                                                            CDR1
 91 AAGAAGCCTGGAGAGACAGTCAAGATCTCCTGCAAGGCTTCTGGGTATACCTTCACACACTATGGAATGAACTGGGTGAAGCAGGCTCCA   180
    K   K   P   G   E   T   V   K   I   S   C   K   A   S   G   Y   T   F   T   T   H   Y   G   M   N   W   V   K   Q   A   P
                                                                                                                    FR3
                                                CDR2
181 GGAAAGGGTTTAAAGTGATGGGCTGGATAAACACTTACACTGGAGAGCCATCATATGCTGATGACTTCAAGGGACGGTTTGCCTTCTCT   270
    G   K   G   L   K   W   M   G   W   I   N   T   Y   T   G   E   P   S   Y   A   D   D   F   K   G   R   F   A   F   S
                                                                                                                CDR3
271 TTGGAAACCTCTGCCAGTACTGCCTATTTGCAGATCAACAACCTCAAAAATGAGGACATGGCTACATATTTCTGTGCCAGAGAGGAGGAC   360
    L   E   T   S   A   S   T   A   Y   L   Q   I   N   N   L   K   N   E   D   M   A   T   Y   F   C   A   R   R   R   D
                                                FR4                                                     CH1
361 TACGGTACTAGCCACTGGTACCTCGATGTCTGGGGCGCAGGGACCACGGTCACCGTCTCCTCAGCCAAAACGACACCCCCATCTGTCTAT   450
    Y   G   T   S   H   W   Y   L   D   V   W   G   A   G   T   T   V   T   V   S   S   A   K   T   T   P   P   S   V   Y
451 CCACTGGCCCCTGGATCTGCCAAACTAACTCCATGGTGACCCTGGTCAAGGGCTATTTCCCTGAGCCAGTGACAGTG   540
    P   L   A   P   G   S   A   A   Q   T   N   S   M   V   T   L   G   C   L   V   K   G   Y   F   P   E   P   V   T   V
541 ACCTGGAACTCTGGATCCCTGTCCAGCGGTGTGCACACCTTCCAGCTGTCCTGACTCTACACTCTGAGCAGCTCAGTGACT   630
    T   W   N   S   G   S   L   S   S   G   V   H   T   F   P   A   V   L   Q   S   D   L   Y   T   L   S   S   S   V   T
631 GTCCCCTCCAGCACCTGGCCCAGCCAGCGAGACCGTCACCTGCAACGTTGCCCAGCGGCCAGCAGCACCAAGGTGGACAAGAAAATTGGATCC   720
    V   P   S   S   T   W   P   S   E   T   V   T   C   N   V   A   H   P   A   S   S   T   K   V   D   K   K   I   G   S
721 AGATCTGCGG   730
    R   S   A
```

SEQ ID NO: 7 and SEQ ID NO: 16

FIG. 4

Anti-MPF Clone 41-28 Light Chain

```
             signal sequence                                    FR1
  1  ATGAAGTTGCCTGTTAGGCTGTTGGTGCTGATGTTCTGATTCTGCTTCCAGCAGTGATGTTTTGATGACCCAAACTCCACTCTCCCTG   90
     M  K  L  P  V  R  L  L  V  L  M  F  W  I  P  A  S  S  S  D  V  L  M  T  Q  T  P  L  S  L
                                                                                         CDR1                    FR2
 91  CCTGTCAGTCTTGGAGATCAAGCCTCCATCTCTGCAGATCTAGTCAGAGCTTTGTACATAGTAGTAATGGAAATACTTATTTAGAATGGTAC   180
     P  V  S  L  G  D  Q  A  S  I  S  C  R  S  S  Q  S  F  V  H  S  N  G  N  T  Y  L  E  W  Y
                                           CDR2                                    FR3
181  CTGCAGAAACCAGGCCAGTCTCCAAAGCTCCTGATCTACAAAGTTTCCAACCGATTTTCTGGGGTCCCAGACAGGTTCAGTGGCAGTGGA   270
     L  Q  K  P  G  Q  S  P  K  L  L  I  Y  K  V  S  N  R  F  S  G  V  P  D  R  F  S  G  S  G
                                                                    CDR3
271  TCAGGGACAGATTTCACACTCAAGATCAGCAGAGTGGAGGCTGAGGATCTGGGATTTTATTACTGCTTTCAAGGTTCACATGTTCCGTAC   360
     S  G  T  D  F  T  L  K  I  S  R  V  E  A  E  D  L  G  F  Y  Y  C  F  Q  G  S  H  V  P  Y
                                             CL1
                     FR4
361  ACGTTCGGAGGGGGGACCAAGCTGGAAATAAAACGGGCTGATGCTGCACCAACTGTATCCATCTTCCCACCATCCAGT   438
     T  F  G  G  G  T  K  L  E  I  K  R  A  D  A  A  P  T  V  S  I  F  P  P  S  S
```

FIG. 5

SEQ ID NO: 8 and SEQ ID NO. 17

Anti-MSLN Clone IC14-30 Heavy Chain

```
     signal sequence                                                         FR1
1    ATGAAATGCAGCTGGGGCATCTTCTTCCTGATGGCAGTGGTTACAGGGGTCAATTCAGAGGTTCAGCTGCAGCAGTCGGGGGCAGACCTT    90
     M  K  C  S  W  G  I  F  F  L  M  A  V  V  T  G  V  N  S  E  V  Q  L  Q  Q  S  G  A  D  L CDR1                              FR2
91   GTGAAGCCAGGGGCCTCAGTCAAGTTGTCCTGCATAGTTTCTGCCTTCAACATTGAAGACACCTATATGCACTGGGTGAAGCAGAGGCCT    180
     V  K  P  G  A  S  V  K  L  S  C  I  V  S  A  F  N  I  E  D  T  Y  M  H  W  V  K  Q  R  P FR3
181  GAACAGGGCCTGGAGTGGATTGGAAGTATTGACCCTGCCATGATAATGACTAAATATGACCCGAAGTTCCAGGTCAAGGCCACTATCACA    270
     E  Q  G  L  E  W  I  G  S  I  D  P  A  H  D  N  A  K  Y  D  P  K  F  Q  V  K  A  T  I  T CDR2                                                                      CDR3
271  GCAGACACATCCTCCAATACAGCCTACTTGCAGCTCAGCAGCCTGACATCTGAGGACTCTGCTGTCTATTACTGTGCCAAATCGGATGGT    360
     A  D  T  S  S  N  T  A  Y  L  Q  L  S  S  L  T  S  E  D  T  A  V  Y  Y  C  A  K  S  D  G FR4
361  TTCTACTTTGACTCCTGGGGCCAAGGCACCACTCTCACAGTCTCCTCAGCCAAAACGACACCCCCATCTGTCTATCCACTGGCCCCTGGA    450
     F  Y  F  D  S  W  G  Q  G  T  T  L  T  V  S  S  A  K  T  T  P  P  S  V  Y  P  L  A  P  G CH1
451  TCTGCTGCCCAAACTAACTCCATGGTGACCCTGGGATGCCTGGTCAAGGGCTATTTCCCTGAGCCAGTGACAGTGACCTGGAACTCTGGA    540
     S  A  A  Q  T  N  S  M  V  T  L  G  C  L  V  K  G  Y  F  P  E  P  V  T  V  T  W  N  S  G 541  TCCCTGTCCAGCGGTGTGCACACCTTCCCAGCTGTCCTGCAGTCTGACCTCTACACTCTGAGCAGCTCAGTGACTGTCCCCTCCAGCACC    630
     S  L  S  S  G  V  H  T  F  P  A  V  L  Q  S  D  L  Y  T  L  S  S  S  V  T  V  P  S  S  T 631  TGGCCCAGCGAGAGCGTCACCTGCAACGTGGCCCACCCGGCCAGCAGCACAAAGGTGGACAAGAAAATTGATCCAGATCTGCG           714
     W  P  S  E  T  V  T  C  N  V  A  H  P  A  S  S  T  K  V  D  K  K  I  G  S  R  S  A SEQ ID NO: 9 and SEQ ID NO> 18                       FIG. 6
```

Anti-MSLN Clone IC14-30 Light Chain

SEQ ID NO: 10 and SEQ ID NO.19

Anti-MSLN Clone 11-25 Heavy Chain

```
    signal sequence                                                        FR1
1   ATGGCTGTCTTGGGGCTGCTCTTCTGCCTGCTGGTTGCATTTCCAAGCTGTGTCCTGTCCCAGGTGCAGCTGAAGGAGTCAGGACCTGGCCTG    90
    M   A   V   L   G   L   L   F   C   L   L   V   A   F   P   S   C   V   L   S   Q   V   Q   L   K   E   S   G   P   G   L
                                                                              CDR1                                FR2
91  GTGGCGCCCTCACAGAGTCTGTCCATCACTTGCACTGTCTCTGGGTTTTCATTAAC AGCTATGGTGTACAG TGGGTTCGCCAGCCTCCA   180
    V   A   P   S   Q   S   L   S   I   T   C   T   V   S   G   F   S   L   T   S   Y   G   V   Q   W   V   R   Q   P   P
                                                                              CDR2                                FR3
181 GGAAAGGGTCTGGAGTGGCTGGGA GTAATATGGGCTGGTGAAGCACAAAATATAATTCGGCTCTCATGTC AGACTGAGCATCAGCAAA    270
    G   K   G   L   E   W   L   G   V   I   W   A   G   G   S   T   K   Y   N   S   A   L   M   S   R   L   S   I   S   K
                                                                                                  CDR3
271 GACAACTCCAAGAGCCAAGTTTTCTTAAAAATGAACAGTCTGCAAACTGATGACACAGCCATGTACTACTGTGCCAGA GATGATTACTAC   360
    D   N   S   K   S   Q   V   F   L   K   M   N   S   L   Q   T   D   D   T   A   M   Y   Y   C   A   R   D   D   Y   Y
                                                        FR4                                      CH1
361 CGTCGTACCTCCCTCTATGCTATGGACTAC TGGGGTCAAGGAACCTCAGTCACCGTCTCCTCA GCCAAAACAACACCCCCATCAGTCTAT   450
    R   R   T   S   L   Y   A   M   D   Y   W   G   Q   G   T   S   V   T   V   S   S   A   K   T   T   P   P   S   V   Y

451 CCACTG  456
    P   L
```

FIG. 8

SEQ ID NO: 11 and SEQ ID NO: 20

SEQ ID NO: 12 and SEQ ID NO. 21

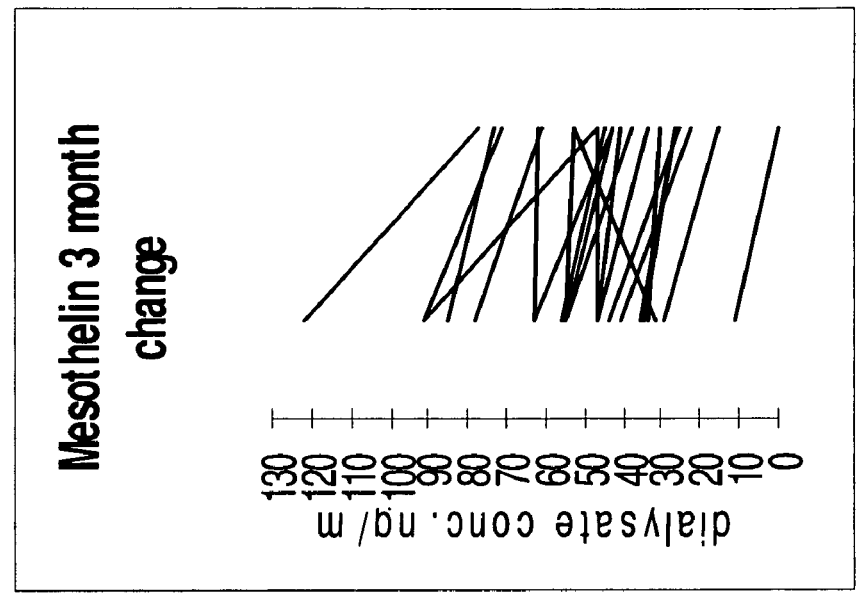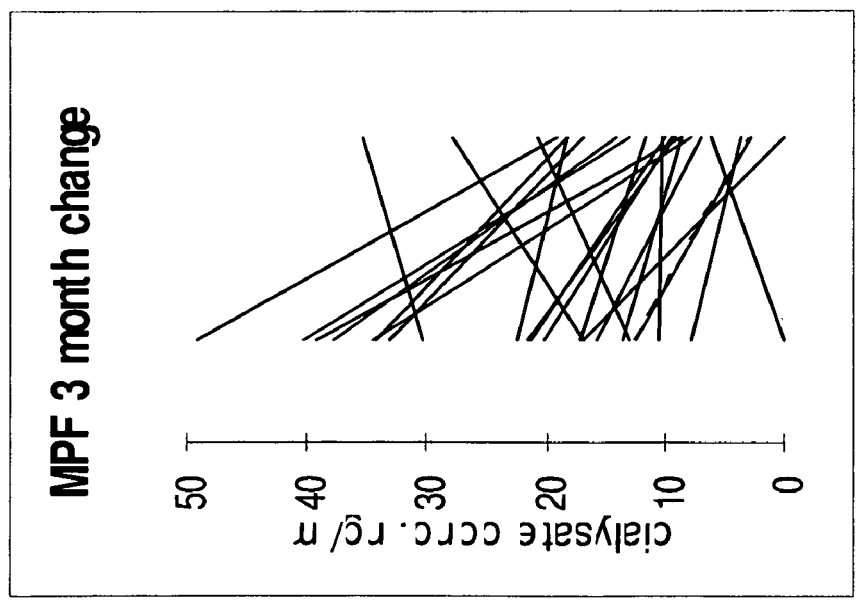
FIG. 12

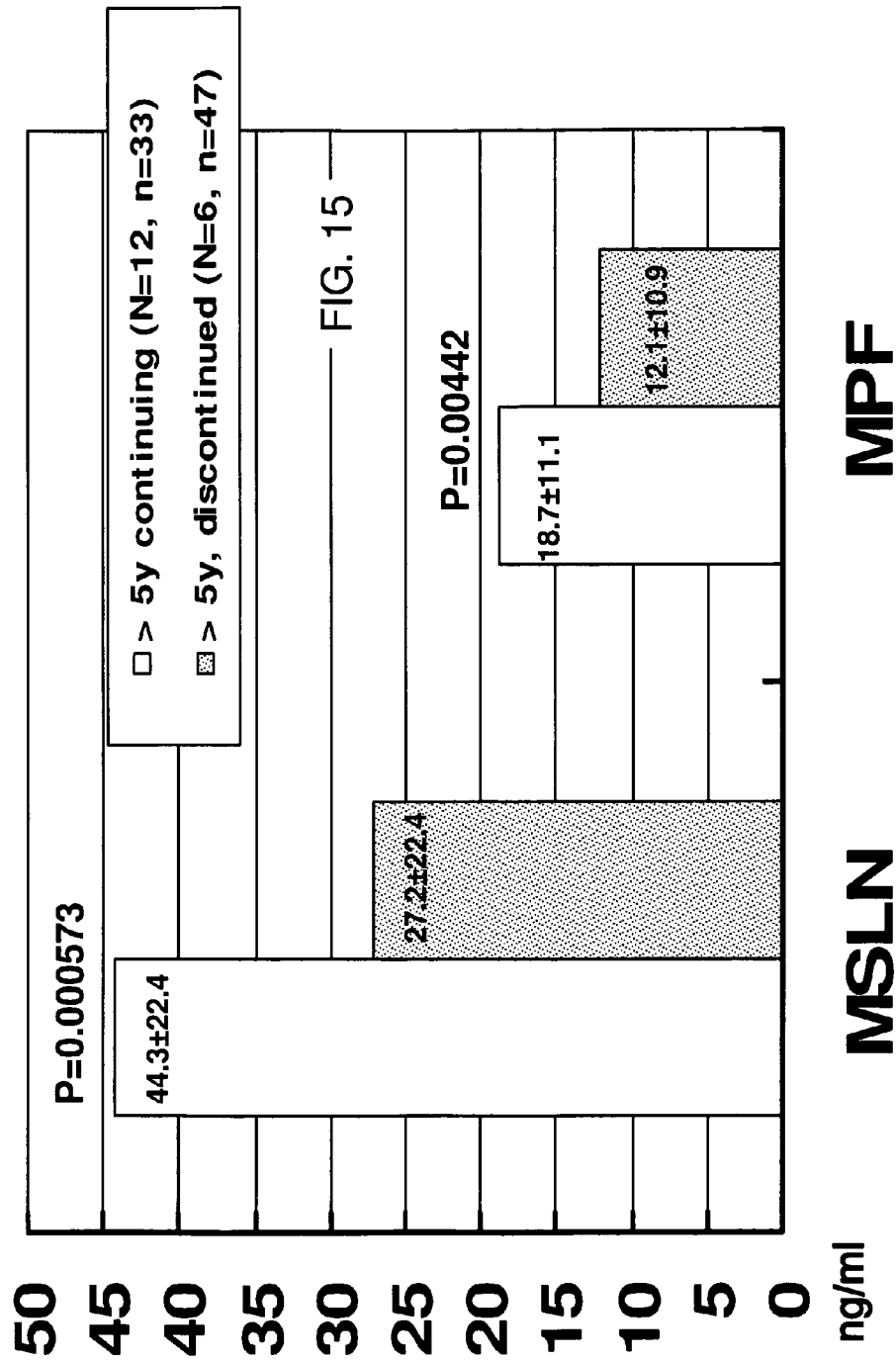

METHODS, KITS, REAGENTS AND DEVICES FOR DETECTING MESOTHELIN AND/OR MEGAKARYOCYTE POTENTIATING FACTOR IN PERITONEAL FLUIDS

PRIORITY APPLICATION

This application claims priority to U.S. Provisional Application No. 61/074,341 filed on Jun. 20, 2008, the entire disclosure of which is hereby incorporated herein by reference for all purposes.

TECHNOLOGICAL FIELD

Certain embodiments disclosed herein are directed to assays, kits, reagents and devices for detecting mesothelin fragments in peritoneal fluids. More particularly, certain embodiments are directed to monitoring the condition of the peritoneal cavity, fluids therein, and the cellular integrity of peritoneal membranes by detecting a decrease in mesothelin, megakaryocyte potentiating factor (MPF), or both, e.g., as compared to a reference standard.

BACKGROUND

Peritoneal dialysis (PD) is a common therapeutic method for the treatment of kidney failure. Patients whose kidneys have insufficient capacity to filter the blood inject dialysis solution into their peritoneal body cavity in order to clear excessive salts, uric acid and other waste substances. By osmosis across the peritoneal membrane, solutes are exchanged between the blood and the dialysis fluid. After a suitable time, the dialysis fluid is removed from the peritoneum and discarded. In this way, the blood becomes equilibrated and terminal metabolic products, such as uric acid, are prevented from indefinitely accumulating in the blood.

An alternative treatment to PD is hemodialysis (HD). It is known that PD is superior to HD in preserving the patient's residual kidney function and also is accompanied by less severe anemia than HD. As a consequence, PD has a superior survival rate during the first two years of treatment (mainly due to a lower risk of cardiovascular events). In the long term, however, PD can lead to peritoneal hypertransport, peritoneal hypertrophy, non-bacterial peritonitis and encapsulating peritoneal sclerosis (EPS). Peritoneal hypertrophy describes an inflammation-like thickening of the peritoneal mesothelium, accompanied by intense vascularization and consequentially more efficient solute exchange between the blood and dialysis solution—thus hypertransport. Unfortunately, peritoneal hypertrophy often progresses to obstructive symptoms in the bowel, ranging from chronic pain and toilet difficulties to death.

SUMMARY

In certain aspects discussed herein, the devices, reagents, methods and kits described advantageously detect a decrease in megakaryocyte potentiating factor (MPF), mesothelin (MSLN) or both to assess the condition of the peritoneal cavity of a subject, e.g., a subject undergoing treatment for kidney malfunction. The MPF and MSLN levels may be measured in a body fluid including, but not limited to, serum and peritoneal fluid, using the illustrative devices, reagents, methods and kits described herein or other suitable devices, reagents, methods and kits that will be selected by the person of ordinary skill in the art, given the benefit of this disclosure.

In one aspect, a method of assessing the condition of the peritoneal cavity and/or peritoneal membrane of a subject undergoing treatment for kidney malfunction is described. In certain examples, the method comprises exposing peritoneal fluid of the subject to at least one binding agent specific for MPF to determine the level of MPF in the peritoneal fluid.

In one embodiment, the method may further comprise comparing the determined level of MPF in the peritoneal fluid to a reference standard, e.g., the level of MPF detected in the blood prior to or at the time of initiation of dialysis treatment, or detected in the peritoneal fluid at the initiation or within one, two, three months of initiating dialysis treatment for kidney malfunction in the subject. In another embodiment, the method may further comprise selecting a treatment for the subject based upon the level of MPF in the peritoneal fluid. In some examples, the treatment selected may be peritoneal dialysis. In some embodiments, if the MPF level is greater than a threshold level, e.g., the MPF level is statistically the same or greater than, for example, a certain/defined fraction of the reference standard, the treatment selected is peritoneal dialysis. In some embodiments, if the MPF level is statistically less than the same fraction of the reference standard or decreases below the same fraction of the reference standard, the treatment selected is hemodialysis.

In certain embodiments, the binding agent is selected from a small molecule and a protein (e.g., a ligand, antibody or antigen binding fragments thereof). In some embodiments, the binding protein is an antibody or antigen binding fragment thereof that binds to MPF, e.g., binds to at least 10 or at least 20 contiguous amino acids shown in SEQ ID NO.: 1 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 4). In some embodiments, the binding protein is an antibody or antigen binding fragment thereof comprising three light chain (LC) complementarity determining regions (CDRs) of antibody 20-10 (as shown in FIG. 3) or antibody 4'-28 (as shown in FIG. 5). In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 5) and three light chain (LC) complementarity determining regions (CDRs) of antibody 20-10 (as shown in FIG. 3) or antibody 41-28 (as shown in FIG. 5). In some embodiments, the binding protein further includes one or more framework regions from the heavy chain and/or light chain of antibody 20-10 or antibody 41-28. In some embodiments, the antibody or antigen binding fragment thereof includes a constant region or a portion of a constant region, e.g., a constant region or portion of a constant region as described herein. In certain embodiments, the antibody, or antigen binding fragment thereof, binds to the same epitope as antibody 20-10. In other embodiments, the antibody, or antigen binding fragment thereof, binds to the same epitope as antibody 41-28.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In other embodiments, the level of MPF may be determined by contacting the MPF with a second binding agent of MPF, e.g., a second binding agent that binds to a region of MPF that is different from the first binding agent, comprising a detectable label. In an additional embodiment, the detectable label is a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In some embodiments, the level of MPF is determined at one, two, three, four, five or six months, one year, two years or up to ten years or more after treatment for kidney malfunction is initiated.

In some embodiments, the method may further comprise determining the level of MPF in a body fluid more than once during treatment of kidney malfunction, e.g., peritoneal dialysis. In certain examples, the MPF level may be determined weekly, monthly, every two or three months, every six months or yearly.

In an additional aspect, a method of assessing the condition of the peritoneal cavity and/or peritoneal membrane of a subject receiving treatment for kidney malfunction is disclosed. In some examples, the method comprises exposing peritoneal fluid of the subject to at least one binding agent specific for MSLN to determine the level of MSLN in the peritoneal fluid.

In certain embodiments, the method may further comprise comparing the determined level of MSLN in the peritoneal fluid to a reference standard, e.g., the level of MSLN detected in the blood prior to or at the time of initiation of dialysis treatment, or detected in the peritoneal fluid at the initiation or within one, two, three months of initiating dialysis treatment for kidney malfunction in the subject. In other embodiments, the method may further comprise selecting a treatment for the subject based upon the level of the MSLN in the peritoneal fluid. In some embodiments, the treatment selected may be peritoneal dialysis. In certain embodiments, if the MSLN level is more than a threshold level, e.g., the MSLN level is statistically the same or greater than, for example, a certain fraction of the reference standard, the treatment selected is peritoneal dialysis. In other embodiments, if the decrease in MSLN level is statistically less than the same fraction of the reference standard or decreases below a certain fraction of the reference standard, the treatment selected is hemodialysis.

In certain examples, the binding agent is selected from a small molecule and a protein (e.g., a ligand, antibody or antigen binding fragments thereof). In some embodiments, the binding protein is an antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of IC14-30 (as shown in FIG. 6) or antibody 11-25 (as shown in FIG. 8). In some embodiments, the binding protein is an antibody or antigen binding fragment thereof comprising three light chain (LC) complementarity determining regions (CDRs) of antibody IC14-30 (as shown in FIG. 7) or antibody 11-25 (as shown in FIG. 9). In some embodiments, the binding protein is an antibody or antigen binding fragment thereof comprising three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the binding protein further includes one or more framework regions from the heavy chain and/or light chain of antibody IC14-30 or antibody 11-25. In some embodiments, the antibody or antigen binding fragment thereof includes a constant region or a portion of a constant region, e.g., a constant region or portion thereof described herein. In certain embodiments, the antibody, or antigen binding fragment, thereof binds to the same epitope as antibody IC14-30. In other embodiments, the antibody, or antigen binding fragment thereof, binds to the same epitope as antibody 11-25.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In some embodiments, the level of MSLN may be determined by contacting the MSLN with a second binding agent of MSLN, e.g., a second binding agent that binds to a region of MSLN that is different from the first binding agent, comprising a detectable label. In an additional embodiment, the detectable label is a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In some embodiments, the method may further comprise determining the level of MSLN in a body fluid more than once during treatment of kidney malfunction, e.g., peritoneal dialysis. In certain examples, the MSLN level may be determined weekly, monthly, every two or three months, every six months, or yearly.

In other embodiments, the method may further comprise selecting a treatment for the subject based upon the level of the MSLN in the peritoneal fluid. In some embodiments, the treatment selected may be peritoneal dialysis. In certain embodiments, if the MSLN level is more than a threshold level, e.g., the MSLN level is statistically the same or greater than, for example, a certain fraction of the reference standard, the treatment selected is peritoneal dialysis. In other embodiments, if the decrease in MSLN level is statistically less than a certain fraction of the reference standard or decreases below the reference standard, the treatment selected is hemodialysis.

In another aspect, a method of detecting MPF in a body fluid of a subject is described. In some examples, the method comprises contacting the body fluid of the subject to at least one antibody, or antigen binding fragment thereof, that binds to a first epitope of MPF, contacting the body fluid to a second antibody, or antigen binding fragment thereof, comprising a detectable label that binds to a second epitope of MPF different from the first epitope, and detecting the level of MPF in the body fluid using the first and second antibodies or antibody fragments. The detectable label can be, e.g., a radioactive label, a fluorescent label, a luminescent label, a paramagnetic label, or an enzyme.

In certain embodiments, the method may comprise comparing the determined level of MPF in the body fluid (or more particularly, the level in peritoneal fluid) to a reference standard, e.g., the level of MPF detected in the blood prior to or at the time of initiation of dialysis treatment, or detected in the peritoneal fluid at the initiation or within one, two, three months of initiating dialysis treatment for kidney malfunction in the subject.

In another embodiment, the method may further comprise selecting a treatment for the subject based upon the level of MPF in the peritoneal fluid. In some examples, the treatment selected may be peritoneal dialysis. In some embodiments, if the MPF level is greater than a threshold level, e.g., the MPF level is statistically the same or greater than, for example, a certain fraction of the reference standard, the treatment selected is peritoneal dialysis. In some embodiments, if the MPF level is statistically less than the same fraction of the reference standard or decreases below the same fraction of the reference standard, the treatment selected is hemodialysis.

In certain embodiments, the antibody or antigen binding fragment thereof that binds to MPF, e.g., binds to at least 10 or at least 20 contiguous amino acids shown in SEQ ID NO.: 1 or a variant thereof. In some embodiments, the antibody, or antigen binding fragment thereof, is an antibody or antigen binding fragment described herein. In some embodiments, the antibody, or antigen binding fragment thereof, comprises three heavy chain (HC) complementarity determining regions (CDRs) of antibody 20-10 (as shown in FIG. 2) or antibody 41-28 (as shown in FIG. 4). In some embodiments, the antibody, or antigen binding fragment thereof, comprises three light chain (LC) complementarity determining regions (CDRs) of antibody 20-10 (as shown in FIG. 3) or antibody 41-28 (as shown in FIG. 5). In some embodiments, the antibody, or antigen binding fragment thereof, comprises three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the antibody, or antigen binding fragment thereof, further includes one or more framework regions from the heavy chain and/or light chain of antibody 20-10 or antibody 41-28. In some embodiments, the antibody, or antigen binding fragment thereof, includes a constant region or a portion of a constant region, e.g., a constant region or portion of a constant region described herein.

In some embodiments, the method includes contacting MPF in a sample of peritoneal fluid with a first antibody that removes the MPF from the sample, and a second binding antibody that comprises a detectable label. In certain examples, the method may further comprise exposing the peritoneal fluid to MPF labeled with a detectable label. In some embodiments, the method may further comprise determining the level of MPF in the body fluid more than once during treatment of kidney malfunction, e.g., peritoneal dialysis. In certain examples, the MPF level may be determined weekly, monthly, tri-monthly, every six months or yearly.

In another aspect, a method of detecting MSLN in a body fluid of a subject is described. In some examples, the method comprises contacting the body fluid of the subject to at least one antibody, or antigen binding fragment thereof, that binds to a first epitope of MSLN, contacting the body fluid to a second antibody, or antigen binding fragment thereof, comprising a detectable label that binds to a second epitope of MSLN different from the first epitope, and detecting the level of MSLN in the body fluid using the first and second antibodies or antibody fragments.

In certain embodiments, the method may further comprise comparing the determined level of MSLN in the peritoneal fluid to a reference standard, e.g., the level of MSLN detected in the blood prior to or at the time of initiation of dialysis treatment, or detected in the peritoneal fluid at the initiation or within one, two, three months of initiating dialysis treatment for kidney malfunction in the subject. In other embodiments, the method may further comprise selecting a treatment for the subject based upon the level of the MSLN in the peritoneal fluid. In some embodiments, the treatment selected may be peritoneal dialysis. In certain embodiments, if the MSLN level is more than a threshold level, e.g., the MSLN level is statistically the same or greater than, for example, a certain fraction of the reference standard, the treatment selected is peritoneal dialysis. In other embodiments, if the decrease in MSLN level is statistically less than the same fraction of the reference standard or decreases below the same fraction of the reference standard, the treatment selected is hemodialysis.

In certain examples, an antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the antibody or antigen binding fragment thereof comprises three heavy chain (HC) complementarity determining regions (CDRs) of IC14-30 (as shown in FIG. 6) or antibody 11-25 (as shown in FIG. 8). In some embodiments, the antibody or antigen binding fragment thereof comprises three light chain (LC) complementarity determining regions (CDRs) of antibody IC14-30 (as shown in FIG. 7) or antibody 11-25 (as shown in FIG. 9). In some embodiments, the antibody or antigen binding fragment thereof comprises three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the antibody or antigen binding fragment thereof includes one or more framework regions from the heavy chain and/or light chain of antibody 14-30 or antibody 11-25. In some embodiments, the antibody or antigen binding fragment thereof includes a constant region or a portion of a constant region, e.g., a constant region or portion thereof described herein.

In some embodiments, the method may further comprise determining the level of MSLN in the body fluid more than once during treatment of kidney malfunction, e.g., peritoneal dialysis. In certain examples, the MSLN level may be determined weekly, monthly, tri-monthly, every six months or yearly.

In another aspect, a kit for use in detecting the level of MPF in a body fluid (or more particularly, the level in peritoneal fluid), the kit comprising a first binding agent that binds to an epitope of MPF is provided.

In certain embodiments, the binding agent is selected from a small molecule and a protein (e.g., a ligand, antibody or antigen binding fragments thereof). In some embodiments, the binding protein is an antibody or antigen binding fragment thereof that binds to MPF, e.g., binds to at least 10 or at least 20 contiguous amino acids shown in SEQ ID NO.: 1 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 4). In some embodiments, the binding protein is an antibody or antigen binding fragment thereof comprising three light chain (LC) complementarity determining regions (CDRs) of antibody 20-10 (as shown in FIG. 3) or antibody 41-28 (as shown in FIG. 5). In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the binding protein further includes one or more framework regions from the heavy chain and/or light chain of antibody 20-10 or antibody 41-28. In some embodiments, the antibody or antigen binding fragment thereof includes a constant region or a portion of a constant region, e.g., a constant region or portion of a constant region described herein.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the kit includes an agent that binds to the binding agent wherein the agent that binds to the binding agent is labeled. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody. In some embodiments, the kit may include instructions, e.g., instructions for use to determine the condition of the peritoneal cavity and/or peritoneal membrane.

In one embodiment, the kit may further comprise a second binding agent of MPF, for example an antibody or antigen binding fragment thereof that is effective to bind to a different epitope than the first binding agent. In certain examples, the second binding agent may be an antibody, or antigen binding fragment thereof. In some examples, the second binding agent comprises a detectable label. In certain examples, the detectable label is a radioactive label, a fluorescent label, a luminescent label, a paramagnetic label, or an enzyme. In certain embodiments, the kit may further comprise a detectable label that can be coupled to the first binding agent or the second binding agent or both. In some examples, the detectable label is a radioactive label, a fluorescent label, a luminescent label, a paramagnetic label, or an enzyme. In other examples, the kit may comprise a set of MPF standards for use in constructing a standard curve. In some examples, the MPF standards are recombinant MPF. In some examples, the kit may comprise MPF comprising a detectable label. In certain examples, the detectable label is a radioactive label, a fluorescent label, a luminescent label, a paramagnetic label, or an enzyme.

In another aspect, a kit for use in detecting the level of MSLN in a body fluid (or more particularly, the level in peritoneal fluid), the kit comprising a first binding agent that binds to an epitope of MSLN is provided.

In certain examples, the binding agent is selected from a small molecule and a protein (e.g., a ligand, antibody or antigen binding fragments thereof). In some embodiments, the binding protein is an antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of IC14-30 (as shown in FIG. 6) or antibody 11-25 (as shown in FIG. 8). In some embodiments, the binding protein is an antibody or antigen binding fragment thereof comprising three light chain (LC) complementarity determining regions (CDRs) of antibody IC14-30 (as shown in FIG. 7) or antibody 11-25 (as shown in FIG. 9). In some embodiments, the binding protein is an antibody or antigen binding fragment thereof comprising three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the binding protein further includes one or more framework regions from the heavy chain and/or light chain of antibody IC14-30 or antibody 11-25. In some embodiments, the antibody or antigen binding fragment thereof includes a constant region or a portion of a constant region, e.g., a constant region or portion thereof described herein.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the kit further includes an agent that binds to the binding agent and, e.g., the agent that binds the binding agent is labeled. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody. In some embodiments, the kit may include instructions, e.g., instructions for use to determine the condition of the peritoneal cavity and/or peritoneal membrane.

In one embodiment, the kit may further comprise a second binding agent of MSLN, for example an antibody or antigen binding fragment thereof that is effective to bind to a different epitope or site than the first binding agent. In some examples, the second binding agent comprises a detectable label. In certain examples, the detectable label is a radioactive label, a fluorescent label, a luminescent label, a paramagnetic label, or an enzyme. In certain embodiments, the kit may further comprise a detectable label that can be coupled to the first binding agent or the second binding agent or both. In some examples, the detectable label is a radioactive label, a fluorescent label, a luminescent label, a paramagnetic label, or an enzyme. In other examples, the kit may comprise a set of MSLN standards for use in constructing a standard curve. In some examples, the MSLN standards are recombinant MSLN. In some examples, the kit may comprise MSLN comprising a detectable label. In certain examples, the detectable label is a radioactive label, a fluorescent label, a luminescent label, a paramagnetic label, or an enzyme.

In an additional aspect, a kit for detecting the level of MPF or MLSN in a body fluid (or more particularly, the level in peritoneal fluid) is provided. In certain examples, the kit comprises a first antibody, or antigen binding fragment thereof, effective to bind to MPF and a second antibody, or antigen binding fragment thereof, effective to bind to MSLN, e.g., at a different epitope than the first antibody or antigen binding fragment thereof.

In certain embodiments, the first antibody, or antigen binding fragment thereof, binds to MPF, e.g., binds to at least 10 or at least 20 contiguous amino acids shown in SEQ ID NO.: 1 or a variant thereof. In some embodiments, the antibody, or antigen binding fragment thereof, is an antibody or antigen binding fragment described herein. In some embodiments, the first antibody or antigen binding fragment thereof comprising three heavy chain (HC) complementarity determining regions (CDRs) of antibody 20-10 (as shown in FIG. 2) or antibody 41-28 (as shown in FIG. 4). In some embodiments, the first antibody or antigen binding fragment thereof comprising three light chain (LC) complementarity determining regions (CDRs) of antibody 20-10 (as shown in FIG. 3) or antibody 41-28 (as shown in FIG. 5). In some embodiments, the first antibody or antigen binding fragment thereof comprising three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the first antibody includes one or more framework regions from the heavy chain and/or light chain of antibody 20-10 or antibody 41-28. In some embodiments, the first antibody or antigen binding fragment thereof includes a constant region or a portion of a constant region, e.g., a constant region or portion thereof described herein.

In certain examples, the second antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the second antibody or antigen binding fragment thereof comprises three heavy chain (HC) complementarity determining regions (CDRs) of IC14-30 (as shown in FIG. 6) or antibody 11-25 (as shown in FIG. 8). In some embodiments, the second antibody or antigen binding fragment thereof comprises three light chain (LC) complementarity determining regions (CDRs) of antibody IC14-30 (as shown in FIG. 7) or antibody 11-25 (as shown in FIG. 9). In some embodiments, the second antibody or antigen binding fragment thereof comprises three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the second antibody or antigen binding fragment thereof includes one or more framework regions from the heavy chain and/or light chain of antibody IC14-30 or antibody 11-25. In some embodiments, the second antibody or antigen binding fragment thereof includes a constant region or a portion of a constant region, e.g., a constant region or portion thereof described herein.

In certain embodiments, the kit may include instructions for using the first and second antibodies. In some examples, one of the first and second antibodies comprises a detectable label. In certain examples, the detectable label is a radioactive label, a fluorescent label, a luminescent label, a paramagnetic label, or an enzyme. In other examples, the kit may include a detectable label that can be coupled to the first antibody or the second antibody or both. In some examples, the detectable label is a radioactive label, a fluorescent label, a luminescent label, a paramagnetic label, or an enzyme. In one embodiment, the kit may include a set of MPF standards for use in constructing a standard curve. In some examples, the MPF standards are recombinant MPF. In other examples, the kit may include a set of MSLN standards. In some examples, the MSLN standards are recombinant MSLN. In additional examples, the kit may comprise MPF comprising a detectable label, MSLN comprising a detectable label, or both. In some examples, the detectable label is a radioactive label, a fluorescent label, a luminescent label, a paramagnetic label, or an enzyme.

In another aspect, an assay for assessing continuation of peritoneal dialysis for a subject in need of dialysis, the assay comprising contacting peritoneal dialysis fluid, e.g., spent peritoneal fluid, from the subject to at least one binding agent, e.g., an antibody or antigen binding fragment thereof, specific for MPF or MSLN, determining the level of MPF or MSLN in the peritoneal dialysis fluid, and assessing whether to provide peritoneal dialysis or hemodialysis based on the determined level of MPF or MSLN, or based on a decrease in the determined level of MPF or MSLN compared to a reference standard, e.g., a level of MPF and/or MSLN determined at an earlier time, for example the individual's initial level of MPF or MSLN at the onset of peritoneal dialysis treatment or one, two or three months after peritoneal dialysis treatment is initiated is described.

In certain embodiments, the antibody, or antigen binding fragment thereof, specific for MPF binds to MPF, e.g., binds to at least 10 or at least 20 contiguous amino acids shown in SEQ ID NO.: 1 or a variant thereof. In some embodiments, the antibody, or antigen binding fragment thereof, is an antibody or antigen binding fragment described herein. In some embodiments, the antibody or antigen binding fragment thereof specific for MPF comprises three heavy chain (HC) complementarity determining regions (CDRs) of antibody 20-10 (as shown in FIG. 2) or antibody 41-28 (as shown in FIG. 4). In some embodiments, antibody, or antigen binding fragment thereof, specific for MPF comprises three light chain (LC) complementarity determining regions (CDRs) of antibody 20-10 (as shown in FIG. 3) or antibody 41-28 (as shown in FIG. 5). In some embodiments, the antibody, or antigen binding fragment thereof, specific for MPF comprises three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the antibody, or antigen binding fragment thereof, specific for MPF includes one or more framework regions from the heavy chain and/or light chain of antibody 20-10 or antibody 41-28. In some embodiments, the antibody, or antigen binding fragment thereof, specific for MPF includes a constant region or a portion of a constant region, e.g., a constant region or portion thereof described herein.

In certain examples, the antibody, or antigen binding fragment thereof, specific for MSLN binds to, e.g., binds to at least 10 or at least 20 contiguous amino acids shown in SEQ ID NO.: 2 or a variant thereof. In some embodiments, the antibody, or antigen binding fragment thereof, specific for MSLN is an antibody or antigen binding fragment described herein. In some embodiments, the antibody, or antigen binding fragment thereof, specific for MSLN comprises three heavy chain (HC) complementarity determining regions (CDRs) of IC14-30 (as shown in FIG. 6) or antibody 11-25 (as shown in FIG. 8). In some embodiments, the antibody, or antigen binding fragment thereof, specific for MSLN comprises three light chain (LC) complementarity determining regions (CDRs) of antibody IC14-30 (as shown in FIG. 7) or antibody 11-25 (as shown in FIG. 9). In some embodiments, the antibody, or antigen binding fragment thereof, specific for MSLN comprises three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the antibody, or antigen binding fragment thereof, specific for MSLN includes one or more framework regions from the heavy chain and/or light chain of antibody IC14-30 or antibody 11-25. In some embodiments, the antibody, or antigen binding fragment thereof, specific for MSLN includes a constant region or a portion of a constant region, e.g., a constant region or portion thereof described herein.

In some embodiments, the method further comprises discontinuing peritoneal dialysis treatment if the determined level of MPF or MSLN is about 20%, 30%, 40%, 50% or more lower as compared to a reference standard. In some examples, hemodialysis is administered after discontinuing of the peritoneal dialysis treatment. In some embodiments, the method comprises detecting the level of MPF or MSLN using another antibody comprising a detectable label.

In an additional aspect, an antibody of antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MPF is provided. In one embodiment, the HC includes three CDRs from antibody 20-10. In one embodiment, the LC includes three CDRs from antibody 20-10. In some embodiments, the antibody or antigen binding fragment thereof includes one or more frameworks regions from the HC and/or LC of antibody 20-10.

In an additional aspect, an antibody of antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MPF is provided. In one embodiment, the HC includes three CDRs from antibody 41-28. In one embodiment, the LC includes three CDRs from antibody 41-28. In some embodiments, the antibody or antigen binding fragment thereof includes one or more frameworks regions from the HC and/or LC of antibody 41-28.

In an additional aspect, an antibody of antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MSLN is provided. In one embodiment, the HC includes three CDRs from antibody IC14-30. In one embodiment, the LC includes three CDRs from antibody IC14-30. In some embodiments, the antibody or antigen binding fragment thereof includes one or more frameworks regions from the HC and/or LC of antibody IC14-30.

In another aspect, an antibody of antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MSLN is provided. In one embodiment, the HC includes three CDRs from antibody 11-25. In one embodiment, the LC includes three CDRs from antibody 11-25. In some embodiments, the antibody or antigen binding fragment thereof includes one or more frameworks regions from the HC and/or LC of antibody 11-25.

In another aspect, a method of selecting a dialysis treatment is provided. In certain examples, the method comprises selecting peritoneal dialysis if an MPF level in peritoneal fluid is above, for example, a certain fraction of a reference standard, and selecting hemodialysis if the MPF level in the peritoneal fluid is below a certain fraction of a reference standard. In some examples, the reference standard value may be based, at least in part, on a change from an initial MPF value measured at the initiation of or within one, two or three months from the initiation of dialysis treatment. For example, if the MPF level is 50%, 40%, 30%, 20% or less than the reference standard value, then peritoneal dialysis may be discontinued and hemodialysis may be initiated.

In an additional aspect, a method of selecting a dialysis treatment is provided. In certain examples, the method comprises selecting peritoneal dialysis if an MSLN level in peritoneal fluid is above a certain fraction of a reference standard, and selecting hemodialysis if the MSLN level in the peritoneal fluid is below a certain fraction of reference standard. In some examples, the reference standard may be based, at least in part, on a change from an initial MSLN value measured at the initiation of or within one, two, three months from the initiation of dialysis treatment. For example, if the MSLN level is 50%, 40%, 30%, 20% or less than the reference standard, then peritoneal dialysis may be discontinued and hemodialysis may be initiated.

In another aspect, a method of assessing the suitability of continued peritoneal dialysis treatment is described. In certain examples, the method comprises continuing peritoneal dialysis if an MPF level in peritoneal fluid is above a certain fraction of a reference standard, and discontinuing peritoneal dialysis if the MPF level in the peritoneal fluid is below a certain fraction of a reference standard. In some examples, the reference standard may be based, at least in part, on a change from an initial MPF value measured at the initiation of dialysis treatment or within one, two three months from the initiation of dialysis treatment. For example, if the MPF level is 50%, 40%, 30%, 20% or less than the reference standard value, then peritoneal dialysis may be discontinued. In certain examples, hemodialysis may be initiated if peritoneal dialysis is discontinued.

In an additional aspect, a method of assessing the suitability of continued peritoneal dialysis treatment is described. In certain examples, the method comprises continuing peritoneal dialysis if an MSLN level in peritoneal fluid is above a certain fraction of a reference standard, and discontinuing peritoneal dialysis if the MSLN level in the peritoneal fluid is below a certain fraction of a reference standard. In some examples, the reference standard may be based, at least in part, on a change from an initial MSLN value measured at the initiation of dialysis treatment or within one, two, three months of initiating dialysis treatment. For example, if the MSLN level is 50%, 40%, 30%, 20% or less than the reference standard, then peritoneal dialysis may be discontinued. In certain examples, hemodialysis may be initiated if peritoneal dialysis is discontinued.

These and other aspects, features, examples and embodiments are described in more detail below.

BRIEF DESCRIPTION OF THE FIGURES

Certain embodiments are described below with reference to the accompanying figures in which:

FIG. 1 includes the amino acid sequence (SEQ ID NO: 1) of MPF (for known variants, see Swiss-Prot Q13421, residues 32-295) and also includes the amino acid sequence (SEQ ID NO: 2) of mesothelin (for known variants, see Swiss-Prot Q13421, residues 296-606), in accordance with certain examples;

FIG. 2 shows an amino acid sequence (SEQ ID NO. 5) of, and the nucleic acid sequence (SEQ ID NO. 14) encoding, an anti-MPF Clone 20-10 Heavy Chain;

FIG. 3 shows an amino acid sequence (SEQ ID NO. 6) of, and the nucleic acid sequence (SEQ ID NO. 15) encoding, an anti-MPF Clone 20-10 light chain;

FIG. 4 shows an amino acid sequence (SEQ ID NO. 7) of, and the nucleic acid sequence (SEQ ID NO. 16) encoding, an anti-MPF Clone 41-28 heavy chain;

FIG. 5 shows an amino acid sequence (SEQ ID NO. 8) of, and the nucleic acid sequence (SEQ ID NO. 17) encoding, an anti-MPF Clone 41-28 light chain;

FIG. 6 shows an amino acid sequence (SEQ ID NO. 9) of, and the nucleic acid sequence (SEQ ID NO. 18) encoding, an anti-MSLN Clone IC14-30 heavy chain;

FIG. 8 shows an amino acid sequence (SEQ ID NO. 11) of, and the nucleic acid sequence (SEQ ID NO. 20) encoding, an anti-MSLN Clone 11-25 heavy chain;

FIGS. 12A and 12B shows the change over a span of 91 days in MPF and mesothelin, respectively, accumulated in the spent peritoneal dialysis buffer of individual patients undergoing peritoneal dialysis as a treatment of chronic kidney failure, in accordance with certain examples;

FIG. 15 is a bar graph showing that both mesothelin and MPF accumulation in spent dialysis solution are predictive factors with respect to the therapeutic outcome (continuation or abandonment) of the peritoneal dialysis treatment, in accordance with certain examples.

DETAILED DESCRIPTION

Figure 7:
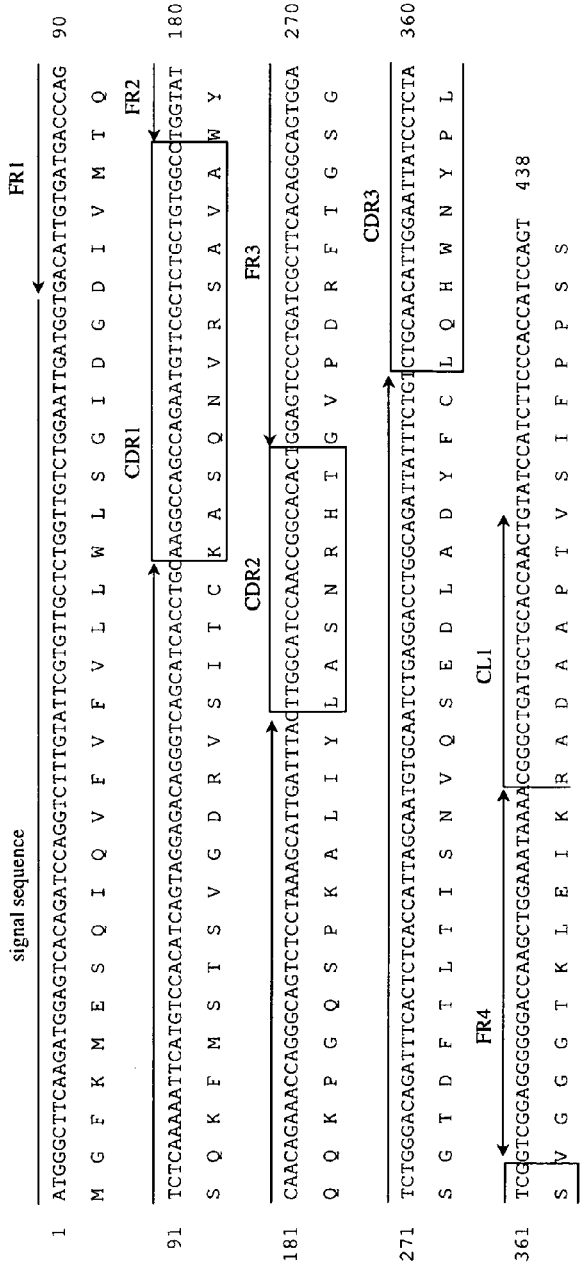
FIG. 7 shows an amino acid sequence (SEQ ID NO. 10) of, and the nucleic acid sequence (SEQ ID NO. 19) encoding, an anti-MSLN Clone IC14-30 light chain.

Certain examples, embodiments, features and aspects described below detect a decrease in the level of megakaryocyte potentiating factor (MPF), mesothelin (MSLN) or both from a reference standard, e.g., the level of MPF or MLSN present in peritoneal fluid at the initiation of peritoneal dialysis or within one, two or three months from the initiation of peritoneal dialysis to assess the health status of a subject, for example, the condition of the peritoneal cavity and/or the peritoneal membrane. Existing assay are designed to detect an increase in MPF as an indicator of cancer or other disease states —See, for example, Iwahori, K. et al. (Lung Cancer 2008, 2008 October; 62(1):45-54. Epub 2008 Apr. 3, the entire disclosure of which is hereby incorporated herein by reference). In contrast to existing methods that measure increases, it has been unexpectedly found that the decreases in the level of MPF, MSLN or both may be used to determine the suitability of a particular treatment for a disease such as malfunction of the kidney. The treatment can be peritoneal dialysis or hemodialysis. In some examples, a decrease in MPF or MSLN may be used to monitor the cytological integrity or general condition of the peritoneal cavity. Additional uses and indications of a decrease in MPF, MSLN or both are discussed in more detail below.

Mesothelial membranes line various body cavities, such as the peritoneal cavity, the pleural cavity, and the pericardial cavity. Peritoneal hypertrophy may be thought of as an inflammatory response to the mechanical stress exerted by an unusual amount of peritoneal fluid and the resulting loss of the mesothelium, a monolayer of cells which protectively cover the peritoneal membrane. As peritoneal hypertrophy may progress even after PD is discontinued, an early diagnostic marker is needed, which can indicate the loss of mesothelial cells before the onset of peritoneal hypertrophy and before hypertransport becomes apparent.

One known diagnostic marker which can be measured in spent dialysate to indicate the health of the mesothelial cell lining is CA125. CA125 has been observed to be present on the surface of some, but not all peritoneal mesothelial cells which detach from the peritoneum during peritoneal dialysis (Kamida at al., poster P-268, 50$^{th}$ symposium of the Japanese Kidney Society). CA125 concentration in spent dialysate fluctuates greatly, and it has not yet proven useful in clinical practice, even though its use in combination with solute transport markers is controversially discussed in the scientific literature (see for example, Krediet, Kidney International 55: 341-356; Otsuka et al., Clin. Exp. Nephrol 9:315-319; Breborowicz et al. Nephron Clin. Pract. 100:c46-c51).

There is no diagnostic marker in clinical practice today which provides an appropriate time point for a PD patients to switch to HD treatment in order to take advantage of the benefits of PD in the early phase (namely protection of residual renal function, less severe anemia and lower risk of cardiovascular events), but avoid the long-term risks (namely bowel obstruction due to peritoneal hypertrophy and EPS).

Mesothelial cells are known to synthesize mesothelin precursor protein. The precursor protein is thought to be efficiently cleaved by a furin protease, yielding a short N-terminal fragment (31 kDa), MPF, that is secreted into the extracellular space, and a longer C-terminal fragment, mesothelin, that remains bound to the cell membrane through a glycophosphatidylinositol (GPI)-anchor.

Mesothelin has been observed on the cell surface of mesothelial cells, mesotheliomas, some squamous cell carcinomas, and ovarian cancers, pancreatic and lung cancers (Chang et al., 1996, Proc. Natl. Acad. Sci. USA 93: 136-140; U.S. Pat. No. 6,083,502), and is under investigation as a target for therapeutic antibodies against those cancers (e.g. US clinical trial no. NCT00325494 by Morphotek, Inc.). MPF, on the contrary, has never been observed on the cell surface. Rather, MPF was first identified in the culture supernatant of a pancreatic cancer cell line, HPC-Y5 (Kojima et al., J. Biol. Chem. 270: 21984-21990; also Japanese patent No. 3490125). This report shows that only MPF, but not full length mesothelin precursor protein, was detected in the culture supernatant of COS cells transfected with full length mesothelin precursor cDNA, indicating that mesothelin precursor is not secreted from the cells but completely cleaved into MPF and mesothelin on before reaching the cell surface.

Scholler et al. (Proc. Natl. Acad. Sci. USA 96: 11531-11536, also U.S. Pat. No. 6,770,445) have reported the generation of several mouse monoclonal antibodies, which could bind to the cell surface of cancer cells expressing mesothelin precursor mRNA, as well as to a recombinant mesothelin fusion protein. This recombinant protein did not incorporate the MPF (N-terminal) portion of mesothelin precursor protein, indicating that the antibodies only bound to the mature mesothelin (C-terminal) portion after proteolytic cleavage. Scholler et al. used two of those antibodies, clones OV659 and 4H3, to construct a sandwich ELISA and demonstrate the presence of Mesothelin or related peptides, which they termed SMR (for soluble mesothelin-related peptides). It is thought that SMR arise from several sources, including release from the cell surface by enzymatic cleavage of the GPI anchor (catalyzed, for example, by phospholipase C).

In contrast, MPF is believed to be cleaved off the precursor protein before the protein reaches the cell surface, because furin protease, which is thought to be responsible for cleaving off MPF from the mesothelin precursor peptide, is ubiquitously expressed in human cells and mainly located in the trans-golgi network (e.g. Nakayama, Biochem. J. 327: 625-635). It is therefore evident that mesothelin precursor protein does not normally enter the blood stream, but rather, the cleavage products, MPF and mesothelin, enter the blood stream separately, after being released from the cells by different and independent mechanisms. It is further evident that MPF and mesothelin would display different pharmacokinetics after entering the blood, as mesothelin has been demonstrated to bind to CA125, a very large glycoprotein which is found on the surface of cells of mullerian epithelial cells and also partially cleaved into the blood stream. In fact, Iwahori et al. (Lung Cancer 2008, referenced herein) measured 70 ng/ml of MPF in the culture supernatant of NCI-H226 cells, a human lung cancer cell line known to express mesothelin precursor mRNA, and 20 ng/ml in the supernatant of HEK 293T cells transfected with a cDNA expression vector of mesothelin precursor. The same culture supernatants only contained 4 ng/ml and 2.8 ng/ml of mesothelin, respectively, suggesting that approximately 80-95% of mesothelin remained bound to the cells under the culture conditions used. In contrast, Iwahori et al. found that healthy Japanese have 9.0+/−2.9 ng/ml MPF and 61.4+/−21.4 ng/ml mesothelin their serum, a finding that suggests that mesothelin may be more stable (approximately by a factor 50-100) in the blood stream than MPF. Taken together, there is ample and consistent evidence over the years indicating that mesothelin and MPF are distinct biomarkers with different mechanisms of secretion, sequestration and degradation.

Patent application WO2005072341 uses the same antibodies as Scholler et al., clones OV659 and 4H3, to demonstrate the presence of mesothelin in peritoneal fluid. The patent discusses the conceptual idea that mesothelial cancers lead to accumulation of peritoneal fluid and the accumulation of mesothelin in the fluid. Therefore, a measurement of a high concentration of mesothelin in peritoneal fluid may indicate that the cause of the accumulation of peritoneal fluid is a cancer, rather than a non-malignant cause. To demonstrate that mesothelin can be detected in peritoneal fluid, the applicants, presumably due to difficulties to find patients with an accumulation of peritoneal fluid due to natural pathological causes, instead showed that about 5-65 ng/ml of mesothelin can be detected in spent peritoneal dialysis fluid.

Dialysis fluid is commonly used in peritoneal dialysis therapy of kidney failure. It is an artificial buffer that is injected into a person's peritoneum for a given span of time and then drained again. WO2005072341 suggests that mesothelial cells in the peritoneum can release mesothelin into peritoneal fluid. Mesothelin concentration is thus an indicator of the condition of the mesothelial cells, and an increase suggests a malignant proliferation of the mesothelial cells. Conceptually, malignant conditions may be particularly conductive to the secretion of mesothelin from the cell surface into the peritoneal fluid, because malignancies often create hypoxic areas of low pH where cells die from necrosis and proteolysis occurs.

These articles, patent publications and patents do not consider the diagnostic usefulness of reduced MPF or MSLN concentration, the use of MPF or MSLN for the diagnosis of any non-neoplastic disease, or the measurement of MPF in body fluids other than blood. While both mesothelin and MPF have attracted attention as diagnostic markers of cancers, these markers have not been considered for monitoring PD therapy, in particular for assessing the risk of future complications or for determination of the optimal time point for patients with kidney dysfunction to stop PD treatment in the favor of HD treatment. MPF has not been demonstrated to exist in detectable amounts in peritoneal or pleural fluids, such as spent peritoneal dialysis solution. In addition, decreases in MPF or MSLN from an initial level were not used in any of the applications as an indicator of a particular condition.

Certain embodiments of the methods, kits, reagents and devices disclosed herein advantageously detect MPF, MSLN or both and in particular detect decreases in MPF, MSLN or both from a reference level, which is typically a level measured or determined at the initiation of treatment. In some embodiments, the levels of MPF, MSLN or both may be used to assess health status including, for example, the health of the abdominal cavity of a subject undergoing peritoneal dialysis. Kits configured to implement the methods are also described.

Certain embodiments disclosed herein are directed to a diagnostic assay that can be performed using a sample of body fluid or peritoneal fluid. In some examples, that fluid sample may be obtained from the peritoneal cavity in order to monitor the cytological integrity of the mesothelial lining of the peritoneal cavity. By way of non-limiting example, the assay can be performed using spent peritoneal dialysis solution to assess the risk of peritoneal complications from peritoneal dialysis treatment.

In some embodiments, a non-invasive method of monitoring the cytological integrity of the mesothelium in a human patient may be performed using the methods and materials described herein. In some examples, the method comprises assessing occurrence of MSLN or MPF, or proteolytic fragments thereof, in a spent dialysis solution obtained from the patient. For example, the amount of MSLN or MPF or fragments thereof that is measured in the spent dialysis fluid, and a decrease over the time of PD therapy in the accumulation of said peptides in the spent dialysis fluid, can be used as an indication of risk that the patient may develop peritoneal hypertrophy and related complications.

In certain embodiments, MSLN or MPF, or fragments thereof, may be assessed in the patient's spent dialysis fluid by exposing the spent dialysis fluid (or centrifuged or filtered dialytic effluent) with a binding agent such as, for example, a first antibody that binds specifically with the MSLN or MPF peptide. By determining whether the MSLN or MPF peptide binds to the first antibody, the presence and level of MSLN or MPF peptide in the patient's mesothelial fluid can be assessed. For example, a first antibody may be bound to a substrate, such as a plastic multi-well plate of the type adapted for automated analysis in a robotic apparatus. Binding of the MSLN or MPF peptide and the first antibody can, for example, be assessed by contacting the first antibody with a second antibody that binds specifically with the MSLN or MPF peptide and assessing co-localization of the first and second antibodies. In some examples, as discussed further below, the second antibody can be detectably labeled, such as with a compound selected from the group consisting of an enzyme, a radionuclide, a fluorophore, and a chromophore or other detectable label. The levels of MPF, MSLN or fragments thereof may be monitored during treatment, and treatment can be discontinued or altered when the MPF or MSLN level falls below a threshold level, whereas the threshold may either be defined as an absolute level or as a decrease relative to the same patient's past MPF or MSLN level, preferably the MPF or MSLN level determined within three months of the initiation of peritoneal dialysis therapy.

In some embodiments, a method comprising contacting a plate, which includes an anti-MSLN or anti-MPF peptide "capture" antibody bound thereto, with spent dialysis fluid obtained from a patient may be performed. The spent dialysis fluid can, optionally, be incubated with the plate for a period such as, for example, ten minutes, twenty minutes, thirty minutes or an hour or other selected times. The plate can then be contacted with a biotinylated second antibody that binds with an epitope of the respective MSLN or MPF peptide that is distinct from the epitope bound by the capture antibody. A streptavidin-linked enzyme can be bound to the biotinylated antibody to enable its detection in the presence of a chromogenic substrate (for example, 3,3',5,5'-tetramethylbenzidine (TMB), which is a chromogenic substrate of horseradish peroxidase). Of course, the second antibody could instead be fluorescently labeled, radiolabeled, or otherwise detectably labeled as discussed in more detail below.

In another embodiment, a method of monitoring the cytological integrity of the mesothelium is provided. In some examples, the method comprises exposing a first antibody with a labeled ligand thereto and contacting the first antibody with the mesothelial fluid. By comparing the amount of labeled ligand that binds with the first antibody that has been contacted with the mesothelial fluid with the amount of labeled ligand that binds with an equivalent amount of the first antibody that has not been contacted with the mesothelial fluid, it is possible to assess how much of MSLN or MPF from the mesothelial fluid has bound with the first antibody.

In certain embodiments of the assays and kits disclosed herein, it is desired, but not necessarily required, that the amino acid sequence of the MPF or MSLN peptide comprises at least 10, 20, 30, 40, 50, 60, 70, 80, 90, 100, 120, 140, 160, 180 or 200 consecutive residues of SEQ ID NO. 1 or SEQ ID NO. 2, or the known variants listed in Swiss-Prot accession number Q13421. Alternatively, the MPF or MSLN peptide can comprise a portion of at least 20 consecutive amino acid residues, wherein the amino acid sequence of the portion is at least 90% (or 95%) identical to 20 consecutive residues of SEQ ID NO. 1 (for MPF) or SEQ ID NO. 2 (for MSLN), or the known variants listed in Swiss-Prot accession number Q13421.

In certain examples, the kits, devices and methods disclosed herein can be used in conjunction with known or hereafter developed kits and methods for assessing the status of the peritoneal cavity (be it for example from spent dialysis fluid, serum, or with imaging techniques such as ultrasound), for example, with indicators of inflammatory and proliferatory processes, indicators of solute transport between blood and dialysate, indicators of proper hemostasis in the patients, and additional indicators of cellular integrity or damage of the peritoneum. Assessment of occurrence of MSLN or MPF, or fragments thereof, in a patient's peritoneal fluid can likewise be performed in conjunction with assessment of MSLN or MPF, or fragments thereof, in the patient's serum.

Substantially the same kits and methods can be used to characterize the peritoneal pathology of a symptomatic patient, such as a patient with symptoms of bacterial or non-bacterial peritonitis or encapsulating peritoneal sclerosis (EPS). Substantially the same kits and methods can also be used to monitor the effect of any given dialysis buffer has on the cellular integrity of the peritoneal mesothelium in vivo or in vitro, for example in order to assess the biocompatibility of a novel dialysis buffer. A rapid change, particularly a decrease, in the accumulation of MSLN or MPF, or fragments thereof, in the dialysis buffer, can prove an indication that the dialysis buffer is not well tolerated by a patient, while a slower change in accumulation of MSLN of MPF, or fragments thereof, in the dialysis buffer can provide an indication of a buffer which causes less risk of peritoneal complications. Such kits, devices and methods can therefore be used to assess the therapeutic value and safety of new agents added to peritoneal dialysis solutions.

These and other embodiments, features, aspect and examples are described in more detail below with reference to the following definitions Megakaryocyte Potentiating Factor ("MPF") refers to a polypeptide having a molecular weight of about 31 kDa and including an amino acid sequence that either (i) comprises at least 10 consecutive residues of SEQ ID NO: 1 or (ii) comprises a portion of at least 20 consecutive amino acid residues wherein the amino acid sequence of the portion is at least 90% (preferably at least 95% or 100%) identical to 20 consecutive residues of SEQ ID NO: 1 as shown in FIG. 1, or the known variants thereof listed in Swiss-Prot accession number Q13421. MPF may be N-glycosylated, and some known small sequence variations are known (see Swiss-Prot accession number Q13421).

Mesothelin ("MSLN") refers to a polypeptide having a molecular weight of about 40 kDa and having an amino acid sequence that either (i) comprises at least 10 consecutive residues of SEQ ID NO: 2 or the known variants listed in Swiss-Prot accession number Q13421, or (ii) comprises a portion of at least 20 consecutive amino acid residues wherein the amino acid sequence of the portion is at least 90% (preferably at least 95% or 100%) identical to 20 consecutive residues of SEQ ID NO: 2 as shown in FIG. 1, or the known variants listed in Swiss-Prot accession number Q13421. Variants of mesothelin are known including, but not limited to, a variant in which eight amino acids, PQAPRRPL (SEQ ID NO: 3), are deleted, and a variant with VQGGRGGQARAG-GRAGGVEVGALSHPSLCRGPLGDALP-PRTWTCSHRPGTAPSLHPGLRAPLPC (SEQ ID NO: 4)

replacing MQEALS (SEQ ID NO: 13) and the hydrophobic GPI linker motif (GTPCLLGPGPVLTVLALLLASTLA (SEQ ID NO: 22)) on the C-terminal side. The mesothelin may include a glycophosphatidylinositol (GPI) anchor and several N-linked sugar chains as post-translational modifications. The GPI anchor binds Mesothelin to the cell membrane but can be cleaved by a phospholipase to provide a soluble form of mesothelin.

MPF/Mesothelin precursor is about a 70 kDa protein that after cleavage by a furin protease provides MPF and MSLN.

The term "body fluid," as used herein is intended to include body fluids that may be extracted, isolated or sampled including fluids naturally occurring in the body (for example, blood, lymph, urine, etc.). Body fluid is also intended to include an artificial solution of fluid that has been equilibrated with the blood (or otherwise mixed with a naturally occurring body fluid) and thus taken up considerable fluid and solutes from the body. For example, in certain embodiments peritoneal fluid may be considered a body fluid. Peritoneal fluid is, for example, fluid found in the peritoneal cavity of an individual, often due to insertion of peritoneal dialysis buffer into the peritoneal cavity.

The term "kidney malfunction" is intended to include kidney disorders, kidney disease, kidney dysfunction, kidney cancer, absence of at least one kidney due to accidents, surgical removal or genetic disorders, or other conditions wherein one or both of the kidneys are not properly functioning.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J. Immunol. 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred. Either or both of polyclonal and monoclonal antibodies can be used in the assays and kits described herein.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with an MPF or MSLN protein, for example, MPF or MSLN in peritoneal fluid.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, for example, disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, for example, HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, for example, derived from a human somatic cell (for example, a hematopoietic cell that produces immunoglobulins or a non-hematopoietic cell). In one embodiment, the human sequences are germline sequences, for example, encoded by a germline nucleic acid. In one embodiment, the framework (FR) residues of a selected antibody can be converted to the amino-acid type of the corresponding residue in the most similar primate germline gene, especially the human germline gene. One or more of the constant regions can be human or effectively human. For example, at least 70, 75, 80, 85, 90, 91, 92, 93, 94, 95, 96, 97, 98, 99, or 100% of an immunoglobulin variable domain, the constant region, the constant domains (CH1, CH2, CH3, CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids) are similarly encoded by a variable region gene (about 116 amino acids) and one of the other aforementioned constant region genes, for example, gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include, but are not limited to, (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See, for example, U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, for example, an epitope. This term includes a "monoclonal antibody" or "monoclonal antibody composition," which as used herein refer to a preparation of antibodies or fragments thereof of single molecular composition, irrespective of how the antibody was generated.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins can be found, for example, in U.S. Pat. Nos. 6,407,213 and 5,693,762.

As used herein, "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ M$^{-1}$ for a particular target molecule, for example, MPF, mesothelin, or fragments thereof. Higher affinity binding of a binding protein to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (for example, a protein in a first conformation or mimic thereof) relative to the second target (for example, the same protein in a second conformation or mimic thereof; or a second protein). Differences in binding affinity (for example, for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (for example, using a fluorescence assay, electron spin resonance or nuclear magnetic resonance). Exemplary conditions for evaluating binding affinity are in TRIS-buffer (50 mM TRIS, 150 mM NaCl, 5 mM CaCl$_2$ at pH 7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N \cdot [\text{Free}]/((1/Ka) + [\text{Free}]).$$

It is not always necessary to make an exact determination of $K_a$, though, since sometimes it is sufficient to obtain a quantitative measurement of affinity, for example, determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, for example, by activity in a functional assay (for example, an in vitro or in vivo assay).

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

An "epitope" refers to the site on a target compound that is bound by a binding protein (for example, an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

Calculations of "homology" or "sequence identity" between two sequences (the terms are used interchangeably herein) may be performed as follows. The sequences are aligned for optimal comparison purposes (for example, gaps can be introduced in one or both of a first and a second amino acid or nucleic acid sequence for optimal alignment and non-homologous sequences can be disregarded for comparison purposes). The optimal alignment is determined, for example, as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 85%, 90%, 91%, 92%, 93%, 94%, 95%, 96%, 97%, 98%, 99%, or 100% of the length of the reference sequence. For example, the reference sequence may be the length of the immunoglobulin variable domain sequence.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (for example, at least about 85% sequence identity) to the sequences disclosed herein are also part of this application. In some embodiments, the sequence identity can be about 60%, 65%, 70%, 75%, 80%, 85%, 90%, 91%, 92%, 93%, 94%, 95%, 96%, 97%, 98%, 99% or higher. In addition, substantial identity exists when the nucleic acid segments hybridize under selective hybridization conditions (for example, highly stringent hybridization conditions), to the complement of the strand. The nucleic acids may be present in whole cells, in a cell lysate, or in a partially purified or substantially pure form.

Clone 41-28 refers to the mouse monoclonal antibody clone 41-28, of isotype IgG1 kappa, specific to MPF, as reported by Iwahori et al., Lung Cancer 2008; the CDR's for Clone 41-28 are shown in FIGS. 4 and 5. This antibody is also referred to in certain instances herein as antibody 41-28.

Clone 20-10 refers to mouse monoclonal antibody 20-10, of isotype IgG1 kappa, specific to MPF, as reported by Iwahori et al., Lung Cancer 2008; the CDR's for Clone 20-10 are shown in FIGS. 2 and 3. This antibody is also referred to in certain instances herein as antibody 20-10.

Figure 9:
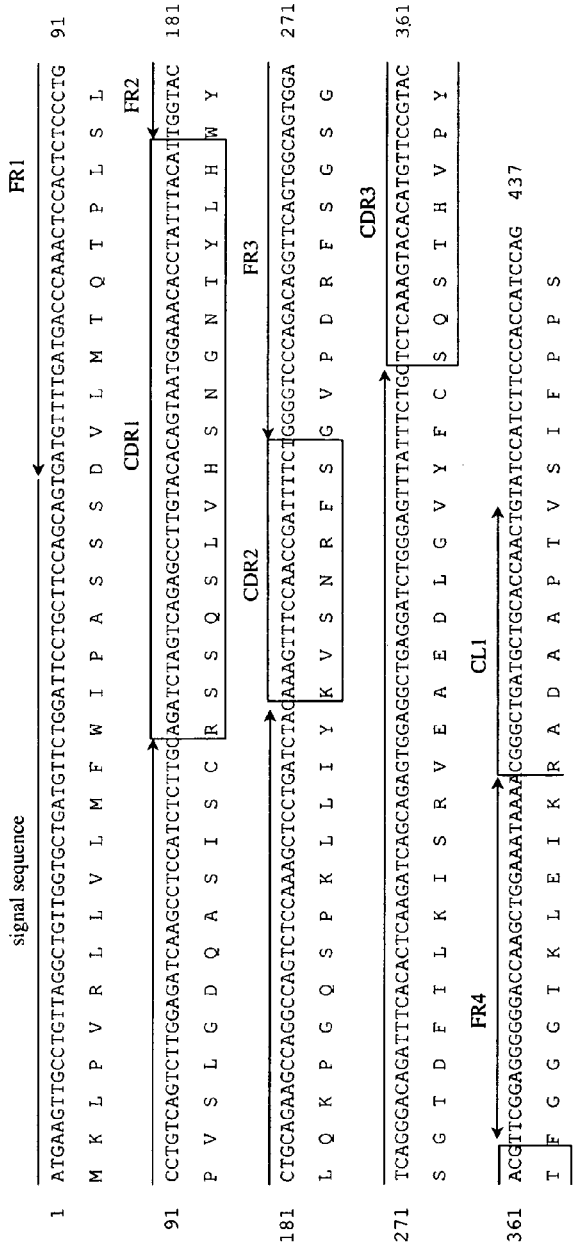
FIG. 9 shows an amino acid sequence (SEQ ID NO. 12) of, and the nucleic acid sequence (SEQ ID NO. 21) encoding, an anti-MSLN Clone 11-25 light chain.

Clone 11-25 refers to mouse monoclonal antibody clone 11-25, of isotype IgG2b kappa, specific to Mesothelin, as reported by Iwahori et al., Lung Cancer 2008; the CDR's for Clone 11-25 are shown in FIGS. 8 and 9. This antibody is also referred to in certain instances herein as antibody 11-25.

Clone IC14-30 refers to mouse monoclonal antibody clone IC14-30, of isotype IgG1 kappa, specific to Mesothelin; the CDR's for Clone IC14-30 are shown in FIGS. 6 and 7. This antibody is also referred to in certain instances herein as antibody IC14-30.

In certain examples, a substantially identical antibody of antibody 20-10 has about 60%, 65%, 70%, 75%, 80%, 85%, 90%, 95%, 96%, 97%, 98%, 99% or 100% of an identical sequence for each of the three CDR's of the light chain and each of the three CDR's of the heavy chain of antibody 20-10. The particular sequence identity of one HC or LC CDR may be the same or different than the sequence identity of the other HC or LC CDRs. In some embodiments, a substantially identical antibody has the three CDR's of the heavy chain and the three CDR's of the light chain of antibody 20-10 and has framework regions substantially identical to the framework regions of antibody 20-10, e.g., 60%, 65%, 70%, 75%, 80%, 85%, 90%, 95%, 96%, 97%, 98%, 99% or 100% identical to the framework region of antibody 20-10.

In certain examples, a substantially identical antibody of antibody 41-28 has about 60%, 65%, 70%, 75%, 80%, 85%, 90%, 95%, 96%, 97%, 98%, 99% or 100% of an identical sequence for each of the three CDR's of the light chain and each of the three CDR's of the heavy chain of antibody 41-28. The particular sequence identity of one HC or LC CDR may be the same or different than the sequence identity of the other HC or LC CDRs. In some embodiments, a substantially identical antibody has the three CDR's of the heavy chain and the three CDR's of the light chain of antibody 41-28 and has framework regions substantially identical to the framework regions of antibody 41-28, e.g., 60%, 65%, 70%, 75%, 80%, 85%, 90%, 95%, 96%, 97%, 98%, 99% or 100% identical to the framework region of antibody 41-28.

In certain examples, a substantially identical antibody of antibody IC14-30 has about 60%, 65%, 70%, 75%, 80%, 85%, 90%, 95%, 96%, 97%, 98%, 99% or 100% of an identical sequence for each of the three CDR's of the light chain and each of three CDR's of the heavy chain of antibody IC14-30. The particular sequence identity of one HC or LC CDR may be the same or different than the sequence identity of the other HC or LC CDRs. In some embodiments, a substantially identical antibody has the three CDR's of the heavy chain and the three CDR's of the light chain of antibody IC14-30 and has framework regions substantially identical to the framework regions of antibody IC14-30, e.g., 60%, 65%, 70%, 75%, 80%, 85%, 90%, 95%, 96%, 97%, 98%, 99% or 100% identical to the framework region of antibody IC14-30.

In certain examples, a substantially identical antibody of antibody 11-25 has about 60%, 65%, 70%, 75%, 80%, 85%, 90%, 95%, 96%, 97%, 98%, 99% or 100% of an identical sequence for the three CDR's of the light chain and three CDR's of the heavy chain of antibody 11-25. The particular sequence identity of one HC or LC CDR may be the same or different than the sequence identity of the other HC or LC CDRs. In some embodiments, a substantially identical antibody has the three CDR's of the heavy chain and the three CDR's of the light chain of antibody 11-25 and has framework regions substantially identical to the framework regions of antibody 11-25, e.g., 60%, 65%, 70%, 75%, 80%, 85%, 90%, 95%, 96%, 97%, 98%, 99% or 100% identical to the framework region of antibody 11-25.

The term "labeled", with regard to an antibody or a peptide, includes direct labeling of the peptide or antibody by coupling (i.e., physically linking) a detectable substance to the peptide or antibody, as well as indirect labeling of the peptide or antibody by coupling it with another reagent that is directly labeled. Examples of indirect labeling include detection of a primary antibody using a fluorescently labeled secondary antibody and end-labeling of a peptide with biotin such that it can be detected with fluorescently labeled streptavidin.

An "instructional material" is a publication, a recording, a diagram, or any other medium of expression which can be used to communicate how to use a kit described herein, information for interpreting occurrence of MPF or Mesothelin in spent peritoneal dialysis fluid as it relates to the cytological status, pathological state, or both, the peritoneal cavity, or relates to the risk of complications from continued peritoneal dialysis treatment, or recommendations of a change of therapy. The instructional material of the kit can, for example, be affixed to a container which contains a kit or be shipped together with a container which contains the kit. Alternatively, the instructional material can be shipped or made available separately from the container with the intention that the instructional material and the kit be used cooperatively by the recipient.

The terms "dialysis fluid" or "dialysis buffer" or "dialysis solution" synonymously refer to an aqueous solution that is commonly inserted into a patient's peritoneal cavity, usually through a surgically inserted access tubing, in order to equilibrate and detoxify the blood after chronic kidney failure. "Spent" dialysis solution refers to the dialysis solution which a patient has drained out of his peritoneal cavity a suitable amount of time (usually several hours) after inserting it. Therefore, spent dialysis solution contains many solutes from the patient's blood stream and peritoneal cavity, including the uremic toxins that the patient's failed kidneys failed to remove, and the concentration of those solutes can be measured to make a diagnostic judgment with respect to the therapeutic status of the patient.

An MPF or MSLN binding protein may have mutations (for example, at least one, two, or four, and/or less than 15, 10, 5, or 3) relative to a binding protein described herein (for example, conservative or non-essential amino acid substitutions), which do not have a substantial effect on protein function. Whether or not a particular substitution will be tolerated, for example, will not adversely affect biological properties, such as binding activity can be predicted (for example, by evaluating whether the mutation is conservative or by the method of Bowie, et al. (1990) Science 247:1306-1310.)

A "conservative amino acid substitution" is one in which the amino acid residue is replaced with an amino acid residue having a similar side chain. Families of amino acid residues having similar side chains have been defined in the art. These families include amino acids with basic side chains (for example, lysine, arginine, histidine), acidic side chains (for example, aspartic acid, glutamic acid), uncharged polar side chains (for example, glycine, asparagine, glutamine, serine, threonine, tyrosine, cysteine), nonpolar side chains (for example, alanine, valine, leucine, isoleucine, proline, phenylalanine, methionine, tryptophan), beta-branched side chains (for example, threonine, valine, isoleucine) and aromatic side chains (for example, tyrosine, phenylalanine, tryptophan, histidine). It is possible for many framework and CDR amino acid residues to include one or more conservative substitutions.

Motif sequences for proteins can include positions which can be varied amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

A "non-essential" amino acid residue is a residue that can be altered from the wild-type sequence of the binding agent, for example, the antibody, without abolishing or more preferably, without substantially altering a biological activity, whereas changing an "essential" amino acid residue results in a substantial loss of activity.

Statistical significance can be determined by many different methods commonly used to assess deviations and variations in data points. Illustrative statistical tests include, but are not limited to: the Students T-test, Mann Whitney U non-parametric test, and Wilcoxon non-parametric statistical test. Some statistically significant relationships have a P value of less than 0.05 or 0.02. Particular binding proteins may show a difference, for example, in specificity or binding, that are statistically significant (e.g., P value<0.05 or 0.02). The terms "induce", "inhibit", "potentiate", "elevate", "increase", "decrease" or the like, for example, which denote distinguishable qualitative or quantitative differences between two states, and may refer to a difference, for example, a statistically significant difference, between the two states, for example, a decrease in MPF or MSLN from an initial level to a current level.

Certain embodiments of the technology described herein are directed to the monitoring of MSLN and/or MPF levels to assess health status and/or health risk. For example, MSLN and MPF show a gradual decline in their ability to accumulate in peritoneal dialysis fluid of peritoneal dialysis patients. A declining accumulation of these biomarkers correlates with physiological changes in the peritoneal membrane, which can lead to treatment complications that indicate the discontinuation of peritoneal dialysis treatment, and may also lead to serious complications such as peritoneal sclerosis, bowel obstruction, chronic pain and death. As discussed herein, a low accumulation of each of these biomarkers in peritoneal dialysis fluid is a statistically significant predictor of the need to discontinue peritoneal dialysis.

A decrease in concentration or occurrence of MPF or MSLN can provide an indication of deterioration of the cytological integrity of the mesothelial membrane lining the peritoneal cavity, both chronically and during acute insults, such as bacterial peritonitis. The amount of MPF and MSLN rebounds after effective treatment of such pathological conditions. Thus, the accumulation of MPF or mesothelin in peritoneal dialysis fluid can also be used to monitor the recovery of the peritoneum after an acute disease or chronic peritoneal dialysis treatment, as well as to assess the biocompatibility of novel dialysis solutions, or to assess the therapeutic effectiveness of therapeutic agents added to a patient's dialysis solution or otherwise administered to a patient in order to protect or improve the health and integrity of the peritoneal membrane, or delay the occurrence of complications from peritoneal dialysis therapy.

MPF was first identified in the culture supernatant of a human pancreatic tumor cell line, HPC-Y5, which enhanced the colony formation of megakaryocytes in an in vitro culture system of mouse bone marrow cells (Yamaguchi N, Hattori K, Oh-eda M, Kojima T, Imai N, Ochi N. A novel cytokine exhibiting megakaryocyte potentiating activity from a human pancreatic tumor cell line HPC-Y5. J. Biol. Chem. 269(2): 805-8 (1994)). Cloning of the cDNA led to the discovery of the full coding sequence of the mesothelin precursor peptide, which comprises of the sequence for mesothelin and MPF, separated by a furin protease cleavage site (Kojima T, Oh-eda M, Hattori K, Taniguchi Y, Tamura M, Ochi N, Yamaguchi N., Molecular cloning and expression of megakaryocyte potentiating factor cDNA. J. Biol. Chem. 270(37):21984-90 (1995))). Mesothelin was subsequently identified to be the cognate antigen for the CAK1 antibody, an antibody known to bind to ovarian cancer cells, and named for its expression in the mesothelial cells lining the peritoneal, pleural and cardiac body cavities (Chang K, Pastan I. Molecular cloning of mesothelin, a differentiation antigen present on mesothelium, mesotheliomas, and ovarian cancers. Proc Natl Acad Sci USA. 93(1):136-40 (1996)). Various researchers subsequently demonstrated that mesothelin as well as MPF can be detected in human serum and are elevated in various cancers of mesothelium-related origin, such as ovarian carcinoma and certain lung cancers. Fujirebio Diagnostics has commercialized a blood test, Mesomark®, which is used for the diagnosis of mesothelioma by measuring mesothelin. http://www.fdi-.com/mesomark/world/home.html While an increase in mesothelin or MPF in a patient is well known to be of diagnostic value for the diagnosis of cancer, embodiments described herein advantageously monitor a decrease in the levels of MSLN or MPF, as compared to an initial level, and correlate the decrease with a deterioration of peritoneal heath during peritoneal dialysis.

Figure 13:
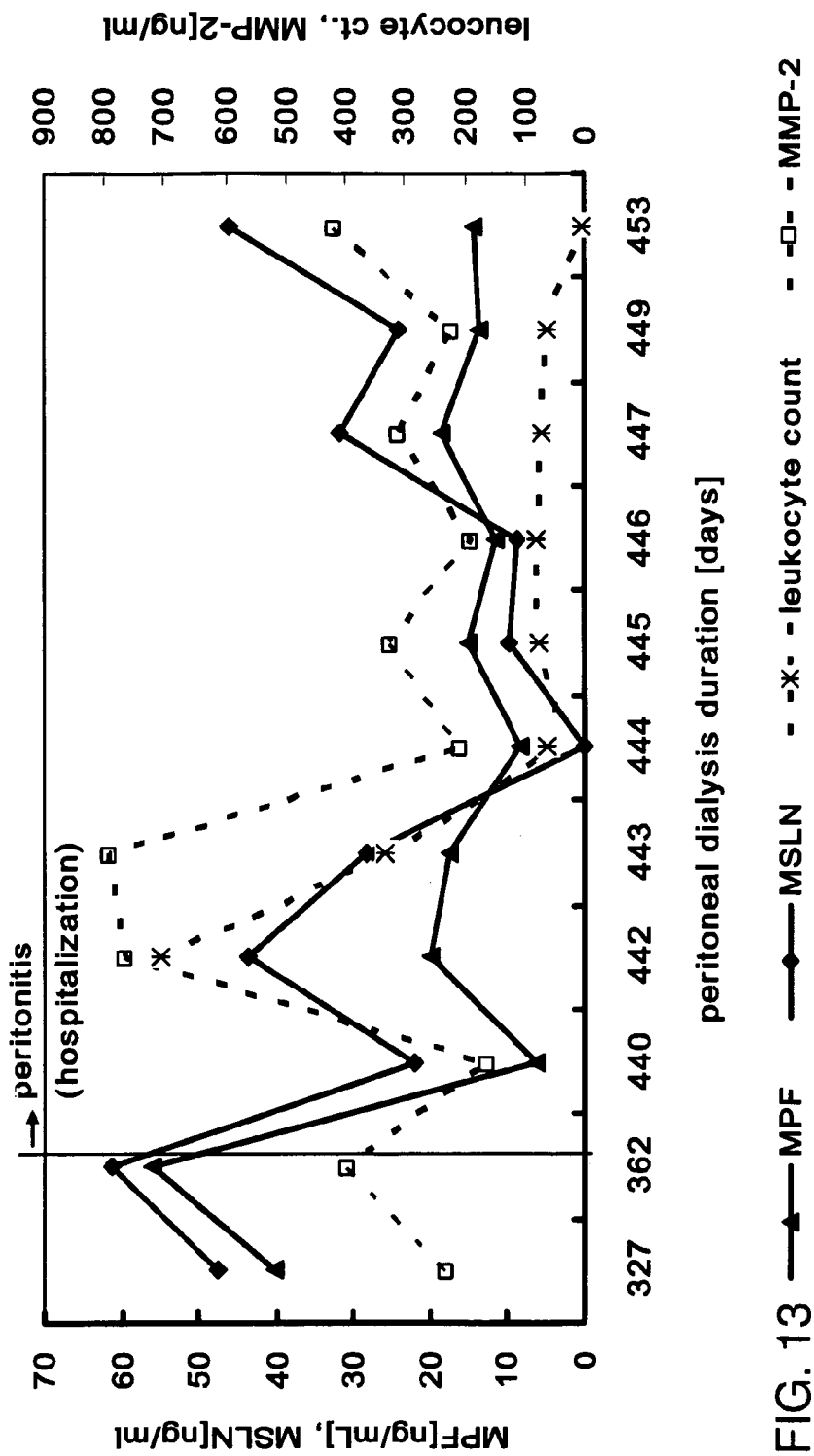
FIG. 13 is a graph showing the level of MPF, mesothelin and other markers accumulated in the peritoneal dialysis buffer of a patient before and after the occurrence of acute bacterial peritonitis, in accordance with certain examples.

The risk of serious complications, such as an inflammatory thickening of the peritoneum leading to obstruction of bowels and other organs, increases with the duration of peritoneal dialysis. Rarely, patients can carry on peritoneal dialysis treatment for much over ten years. Yet, in the first two years, peritoneal dialysis has a lower risk of cardiovascular events and death than hemodialysis. As demonstrated herein, MSLN and MPF accumulation in the peritoneal dialysis solution shows a significant decrease over the years of the therapy (FIG. 14) and showed a clear decrease over a three month span in most of the patients observed (FIG. 13). Importantly, in patients on peritoneal dialysis for 5 years or longer, the decrease in both mesothelin and MPF concentrations in spent dialysis solution were predictive with respect to the treatment, as patients who had to discontinue peritoneal dialysis had a statistically lower concentration of both mesothelin and MPF in their spent dialysis fluid (FIG. 15). In addition, a severe decrease of mesothelin and MPF levels was detected during acute peritonitis (contraction of a bacterial infection of the peritoneum), often to undetectable levels during the acute phase of the infection (FIG. 13). These results are consistent with mesothelin and MPF being biological indicators of the health of the peritoneal membrane, which is known to be sensitive to the physicochemical wear of the dialysis solution. It is known that mesothelial cells can be detached and be washed out by peritoneal dialysis treatment (see for example, Kamida et al., poster P-268, $5^{th}$ symposium of the Japanese Kidney Society), and gradually become replaced by fibroblasts over time during peritoneal dialysis. The decreased accumulation of Mesothelin and MPF in the peritoneal solution is a convenient indicator of this fibrotic process, which leads to dangerous inflammatory complications.

Furthermore, Mesothelin and MPF are not known to be expressed in any non-cancerous cells other than mesothelial cells. As the peritoneum is the largest mesothelium in the body, with the pleura and pericardium being minor additional sources, it is obvious that a person's serum concentration of MSLN or MPF, particularly a decrease of such concentration, is also a biological indicator of the deterioration of peritoneal health during dialysis. This is particularly noteworthy because spent dialysis solution is not available prior to the initiation of peritoneal dialysis treatment. Therefore, serum MSLN or MPF is useful in determining a patient's individual baseline to which later measurements of spent dialysate or serum Mesothelin or MPF can be compared so that the patient's individual decrease can be determined. In addition, serum Mesothelin or MPF may be useful indicators to determine prior to treatment how well a patient may tolerate peritoneal dialysis treatment, and thus give helpful guidance in the choice of therapy.

Furthermore, MSLN or MPF produced in the pleura and pericardium can enter the blood stream, and from there be secreted into the peritoneal cavity together with other serum proteins, and mask a decreased peritoneal production of MSLN and MPF. The amount of serum-derived versus peritoneal derived MSLN or MPF can be assessed by assessing the accumulation of MSLN or MPF in the peritoneal fluid in comparison to the accumulation of total protein, or certain serum proteins of comparable size and property, for example, albumin, beta-trace protein or cystatin C, or creatinine.

MPF and MSLN Level Measurement and Uses

In accordance with certain embodiments, methods to assess the level of MSLN or MPF in a body fluid are provided. In some examples, the methods may be used to diagnose the cytological status and biological integrity of the peritoneal cavity in a patient. In other embodiments, the methods may be used to determine a decrease in the MPF or MSLN level, as compared to an initial level, in a body fluid such as, for example, serum, spent dialysis fluid or the like.

In certain embodiments, the methods may comprise assessing occurrence of MPF or mesothelin in spent peritoneal dialysis solution obtained from a mammalian subject, for example, a human individual with kidney malfunction. A decrease in MPF or mesothelin levels can be used as an indication of a deterioration of the cytological status and biological integrity of the peritoneal lining and therefore an increased risk of treatment complications. After a decrease in the levels by a specific percentage, the peritoneal dialysis treatment may be discontinued and hemodialysis may be initiated. Periodically, the level of MPF or mesothelin in peritoneal fluid may be assessed to determine whether it is safe to resume peritoneal dialysis.

In certain examples, it may be desirable to determine an initial level of MPF or MSLN in a body fluid. Such initial level may be obtained at any point post-gestation including immediately after birth, 1 day from birth, 1 week from birth, 1 month from birth, 1 year from birth, 10 years from birth, 25 years from birth, 50 years from birth, 75 years from birth, 100 years from birth or any time in between. In some examples, it is desirable to determine an initial level of MPF or MSLN in peritoneal fluid as soon as possible after peritoneal dialysis has commenced. Such initial level may be used and compared with subsequent levels to assess whether or not the MPF or MSLN has decreased to the point where it would be advisable to discontinue peritoneal dialysis.

The exact initial level may vary from subject to subject and therefore, in certain embodiments, the change in the MPF or MSLN, rather than the absolute amount present, may be used to assess health status. In some examples, peritoneal dialysis may be discontinued when the MPF level decreases by at least 40%, more particularly decreases by about 80%, as compared to an initial level. In certain examples, a threshold level change may be used to assess whether or not peritoneal dialysis should be continued. In some examples, when the threshold level change is one-half, one-third or one-quarter, one-fifth, one-tenth or one-twentieth of an initial level then peritoneal dialysis may be discontinued. If the actual level shows a sub-threshold level change (such that the level remains above the threshold and thus the decrease compared to an initial value is relatively small), then peritoneal dialysis may be continued. If the actual level shows more than threshold level change (such that the level drops below the threshold and thus the decrease compared to an initial value is relatively large), then peritoneal dialysis may be discontinued and hemodialysis may be initiated.

In embodiments in which an antibody, for example, an anti-mesothelin or anti-MPF peptide antibody, is contacted with spent peritoneal dialysis solution obtained from a patient, the spent peritoneal dialysis solution can be used in its naturally expressed state or it can be partially purified or clarified or filtered or concentrated prior to use. For example, spent peritoneal dialysis solution can be centrifuged using standard methods to substantially remove any sediment therefrom prior to contacting the mesothelial fluid with the antibody. Alternatively, the spent peritoneal dialysis solution can be filtered or ultrafiltered to reduce its volume or to remove large contaminants. Because mesothelin and MPF peptides that occur in spent peritoneal dialysis solution can be expected to be glycosylated polypeptides having molecular weights in the range 10,000-50,000 Daltons, selection of an appropriate filtration/ultrafiltration is desirable to prevent loss of the mesothelin or MPF peptide prior to its detection. By way of example, a relatively large pore filter, for example, one that permits passage of globular particles having molecular weights of 250,000 to 1 million Daltons can be used to remove particulate material from spent peritoneal dialysis solution, and an ultrafiltration device equipped with a membrane that excludes passage of proteins having molecular weights greater than about 5,000 Daltons can be used to concentrate the filtrate. In this example, occurrence of mesothelin or MPF can be assessed in the retentate in the ultrafiltration device.

Because many of the methods (for example, the immunological methods) described herein are relatively sensitive, concentration of spent peritoneal dialysis solution is usually not necessary to detect occurrence of MPF or mesothelin peptides in spent peritoneal dialysis solution of patients. Instead, spent peritoneal dialysis solution may be diluted with a suitable dilution buffer in order to obtain an optimal quantitative readout in the concentration range of interest. In situations in which clarification of spent peritoneal dialysis solution is desired, centrifugation can be preferable, since the potential that mesothelin or MPF peptides present in the spent peritoneal dialysis solution will become bound with or enmeshed within the filter medium is not present.

In certain embodiments, many different methods may be used to assess the level of MPF or mesothelin in the patient's spent dialysis solution. In particular, any method that can be used to assess whether one of the respective peptides is present or absent is suitable. In one embodiment, the level of MPF or mesothelin peptide in the patient's peritoneal fluid may be assessed by exposing the peritoneal fluid to an antibody that binds specifically with the MPF or mesothelin peptide. Such exposing may be accomplished by adding a selected amount of an antibody to the peritoneal fluid. In some examples, a second antibody that binds may be added to the peritoneal fluid to assess whether the MPF or mesothelin peptide has bound with the first antibody. The two antibodies preferably do not compete for binding to the same epitope, but rather bind to the same antigen in a non-competitive manner.

One preferred method for assessing occurrence of MSLN or MPF in the spent peritoneal dialysis solution or other body fluids of a patient is the procedure commonly known as a "sandwich ELISA" assay. (ELISA is an abbreviation for enzyme-linked immunosorbent assay). In this technique an antibody is bound to a substrate, such as a glass bead or the bottom surface of a plastic multi-well assay plate. This antibody is designated a 'capture' antibody. Raw, clarified, or purified spent peritoneal dialysis solution from the patient or a sample of the respective body fluid can be contacted with the substrate under conditions (for example, low concentrations of salt and detergents and non-protein-denaturing conditions), so that any mesothelin or MPF peptide present in the spent peritoneal dialysis solution or body fluid sample can bind specifically with the capture antibody. The substrate is optionally rinsed with a fluid that does not comprise the capture antibody or the mesothelin or MPF peptide to remove residual spent peritoneal dialysis solution or body fluid. The substrate can then be contacted with a second antibody that specifically binds with the mesothelin or MPF peptide at an epitope independent of the epitope at which the capture antibody binds. The second antibody is either detectably labeled or linked with either a ligand or a receptor of the ligand. Either way, binding of the second antibody is detected (and, optionally, quantitated) after rinsing the substrate with a fluid that does not comprise the second antibody. Detection of the second antibody is indicative of the presence in the spent peritoneal dialysis solution or body fluid of respective MPF or MSLN peptides. If the amount of the second antibody is quantitated, then the amount of the MPF or mesothelin peptides in the spent peritoneal dialysis solution or body fluid can be quantitated, for example, by comparison of the amount of second antibody detected with measurements made using control samples or standards containing known amounts of MPF or MSLN.

In other embodiments, a competition assay may be used to assess the presence and/or level or MSLN or MPF in spent peritoneal dialysis solution or in a body fluid. In one embodiment of this assay, an antibody that binds specifically with the mesothelin or MPF peptide can be fixed to a substrate. Raw, clarified, purified or diluted spent peritoneal dialysis solution or body fluid is contacted with the substrate (preferably for a period of minutes or hours), so that any mesothelin or MPF peptides present in the spent peritoneal dialysis solution or body fluid bind with the antibody. A labeled ligand (for example, a labeled version of an MPF or mesothelin peptide) that binds specifically with the antibody is then contacted with the substrate (preferably for a period of minutes or hours). The amount of labeled ligand bound with the substrate is assessed after rinsing the substrate with a fluid that does not comprise the label or the labeled ligand. The amount of label bound with the substrate is compared with the amount of label bound with an otherwise identically treated substrate that is not contacted with the patient's spent peritoneal dialysis solution or body fluid. The difference between the two amounts of bound label represents the amount of MPF or mesothelin peptide bound to the substrate, and is indicative of the amount of MPF or mesothelin peptides that were present in the spent peritoneal dialysis solution or body fluid sample applied to the substrate.

When an immunological competition assay is used, the labeled ligand of the antibody bound with the substrate is desirably as nearly identical to the MPF or mesothelin peptide known or expected to be present in the patient's body fluid or spent peritoneal dialysis solution as possible. For example, the ligand and the MPF or mesothelin peptide should have or comprise the same amino acid sequence in the region bound by the antibody. Similarly, if the MPF or mesothelin peptide that may occur in the patient's spent peritoneal dialysis solution or body fluid is expected to be glycosylated (or modified in some other manner), then the ligand may be glycosylated in the same way, at the same position, and/or to the same extent. In this way, affinity differences of the antibody for the ligand and for the MPF or mesothelin analyte can be minimized and the accuracy of the competition assay can be improved.

In certain examples, a homogeneous assay may be used to assess the presence and level of MSLN or MPF in a body fluid. In a homogenous assay, after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on a first molecule (a donor) is selected such that its emitted fluorescent energy can be absorbed by a fluorescent label on a second molecule (an acceptor) if the second molecule is in proximity to the first molecule. The fluorescent label on the second molecule fluoresces when it absorbs the transferred energy. Since the efficiency of energy transfer between the labels is related to the distance separating the molecules, the spatial relationship between the molecules can be assessed. If the acceptor label is present on a competing ligand, then the overall fluorescence intensity may be reduced in the presence of MPF or MSLN. Where no MPF or MSLN is present, the fluorescent emission of the acceptor molecule label in the assay should be maximal. A binding event that is configured for monitoring by FRET can be conveniently measured through standard fluorimetric detection means, e.g., using a fluorimeter. By titrating the amount of the first or second binding molecule, a binding curve can be generated to estimate the equilibrium binding constant and/or to determine the level of MPF or MSLN in a body fluid. Some particular FRET technologies known to give precise quantitative result useful for monitoring of the change of biomarker levels in a patient over time include, but are not limited to, homogeneous time resolved fluorescence (HTRF) and TR-FRET, FRET techniques which use fluorophores with long emission half-lives, including lanthanides such as europium and terbium (caged in organic complexes called cryptates). Diagnostic HTRF assays for various biomarkers are marketed by BRAHMS AG of Berlin-Henningsdorf, Germany under license from Cisbio, Bagnols/Ceze, France, and essentially similar assays are feasible for the quantification of MSLN or MPF in spent peritoneal dialysis solution or body fluid samples.

Another example of a homogenous assay is ALPHAS-CREEN™ (Packard Bioscience, Meriden Conn.). ALPHAS-CREEN™ uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding. In some examples, a competitive ligand attached to a bead can be used to assess the level of MPF or MSLN in spent peritoneal dialysis solution or in a body fluid, with a decrease in the overall signal indicative of the presence of MPF or MSLN. Where quantitation is desired, standards may be implemented over a desired concentration range and used to determine how much MPF or MSLN is present in spent peritoneal dialysis solution or in a body fluid sample.

In certain examples, surface plasmon resonance (SPR) may be used to measure the level of MPF or MSLN in a body fluid. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr Opin. Struct. Biol.* 5:699-705 and on-line resources provide by BIAcore International AB (Uppsala, Sweden). BIAcore Flexchip can be used to compare and rank interactions in real time, in terms of kinetics, affinity or specificity without the use of labels. Information from SPR can be used to provide an accurate and quantitative measure of kinetic parameters and the levels of MPF or MSLN in spent peritoneal dialysis solution or in a body fluid.

In some examples, cellular assays may be performed to determine the presence and/or level of MPF and/or MSLN. For example, binding proteins can be screened for ability to bind to cells which transiently or stably express and display the target of interest on the cell surface. For example, MPF or MSLN binding proteins can be fluorescently labeled and binding to MPF or MSLN in the presence or absence of antagonistic antibody can be detected by a change in fluorescence intensity using flow cytometry, for example, a fluorescence activate cell sorter. In some examples, cells, beads or other detectable probes which display molecules on their surface that are known to bind to MSLN or MPF may be contacted with the a spent peritoneal dialysis solution of body fluid sample. Such molecules that are known to bind to MSLN or MPF include the antibodies disclosed herein, other antibodies specific to MSLN or MPF, or natural ligand molecules or fragments of such antibodies or ligands, for example CA125 or fragments of CA125 that contain at least one mucinous repeat domain of CA125, which is known to bind specifically to Mesothelin (Rump et al., J Biol. Chem. 5; 279(10): 9190-8 (2004). After suitably contacting the cells or probes with the sample, the amount of MSLN or MPF present in the sample may be quantified in comparison to standard samples by contacting the probe with a labeled molecule that binds MPF or MSLN non-competitively with the first binding molecule, or alternatively, by contacting the probe with a labeled peptide can compete with MSLN or MPF for binding to the binding molecule.

In certain embodiments, a scintillation proximity assay may be used to assess the presence and/or level of MPF or MSLN in spent peritoneal dialysis solution or in a body fluid sample. In a scintillation proximity assay, beads that contain a scintillant that can be stimulated to emit light are used. This stimulation event only occurs when radiolabeled molecules of interest are bound to the surface of the bead. When the molecules are bound, then light is emitted that can be detected on standard scintillation counters or using other suitable optical devices. In some examples, radioactively labeled MPF or MSLN may be added to a bead including a binding protein for MPF or MSLN. A body fluid containing unlabeled MPF or MSLN may be added, and the decrease in fluorescence may be used to determine the level of MPF or MSLN in the sample. A standard curve may be produced using various standard concentrations to facilitate determination of the MPF or MSLN level in a body fluid sample.

In certain embodiments, assays other than those mentioned above may be used or may be used in addition to the assays listed above. For example, agglutination/nephelometry assays, laminar flow/quick tests, antibody chips or other multiplex assays, or assays including nanomaterials such as, for example, carbon nanotube assay may be performed.

In certain examples, a method of assessing the condition of the peritoneal cavity and/or peritoneal membrane of a subject undergoing treatment for kidney malfunction is described. In certain examples, the method comprises exposing peritoneal fluid of the subject to at least one binding agent specific for MPF to determine the level of MPF in the peritoneal fluid.

In one embodiment, the method may further comprise comparing the determined level of MPF in the peritoneal fluid to a reference standard, e.g., the level of MPF detected in the blood prior to or at the time of initiation of dialysis treatment, or detected in the peritoneal fluid at the initiation or within one, two, three months of initiating dialysis treatment for kidney malfunction in the subject. In another embodiment, the method may further comprise selecting a treatment for the subject based upon the level of MPF in the peritoneal fluid. In some examples, the treatment selected may be peritoneal dialysis. In some embodiments, if the MPF level is greater than a threshold level, e.g., the MPF level is statistically the same or greater than, for example, a certain/defined fraction of the reference standard, the treatment selected is peritoneal dialysis. In some embodiments, if the MPF level is statistically less than the same fraction of the reference standard or decreases below the same fraction of the reference standard, the treatment selected is hemodialysis.

In certain embodiments, the binding agent is selected from a small molecule and a protein (e.g., a ligand, antibody or antigen binding fragments thereof). In some embodiments, the binding protein is an antibody or antigen binding fragment thereof that binds to MPF, e.g., binds to at least 10 or at least 20 contiguous amino acids shown in SEQ ID NO.: 1 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 4). In some embodiments, the binding protein is an antibody or antigen binding fragment thereof comprising three light chain (LC) complementarity determining regions (CDRs) of antibody 20-10 (as shown in FIG. 3) or antibody 41-28 (as shown in FIG. 5). In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 5) and three light chain (LC) complementarity determining regions (CDRs) of antibody 20-10 (as shown in FIG. 3) or antibody 41-28 (as shown in FIG. 5). In some embodiments, the binding protein further includes one or more framework regions from the heavy chain and/or light chain of antibody 20-10 or antibody 41-28. In some embodiments, the antibody or antigen binding fragment thereof includes a constant region or a portion of a constant region, e.g., a constant region or portion of a constant region as described herein.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In other embodiments, the level of MPF may be determined by contacting the MPF with a second binding agent of MPF, e.g., a second binding agent that binds to a region of MPF that is different from the first binding agent, comprising a detectable label. In an additional embodiment, the detectable label is a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In some embodiments, the level of MPF is determined at one, two, three, four, five or six months, one year, two years or up to ten years or more after treatment for kidney malfunction is initiated.

In some embodiments, the method may further comprise determining the level of MPF in a body fluid more than once during treatment of kidney malfunction, e.g., peritoneal dialysis. In certain examples, the MPF level may be determined weekly, monthly, tri-monthly, every six months or yearly.

In other examples, a method of assessing the condition of the peritoneal cavity and/or peritoneal membrane of a subject receiving treatment for kidney malfunction is disclosed. In some examples, the method comprises exposing peritoneal fluid of the subject to at least one binding agent specific for MSLN to determine the level of MSLN in the peritoneal fluid.

In certain embodiments, the method may further comprise comparing the determined level of MSLN in the peritoneal fluid to a reference standard, e.g., the level of MSLN detected in the blood prior to or at the time of initiation of dialysis treatment, or detected in the peritoneal fluid at the initiation or within one, two, three months of initiating dialysis treatment for kidney malfunction in the subject. In other embodiments, the method may further comprise selecting a treatment for the subject based upon the level of the MSLN in the peritoneal fluid. In some embodiments, the treatment selected may be peritoneal dialysis. In certain embodiments, if the MSLN level is more than a threshold level, e.g., the MSLN level is statistically the same or greater than, for example, a certain fraction of the reference standard, the treatment selected is peritoneal dialysis. In other embodiments, if the decrease in MSLN level is statistically less than the same fraction of the reference standard or decreases below a certain fraction of the reference standard, the treatment selected is hemodialysis.

In certain examples, the binding agent is selected from a small molecule and a protein (e.g., a ligand, antibody or antigen binding fragments thereof). In some embodiments, the binding protein is an antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of IC14-30 (as shown in FIG. 6) or antibody 11-25 (as shown in FIG. 8). In some embodiments, the binding protein is an antibody or antigen binding fragment thereof comprising three light chain (LC) complementarity determining regions (CDRs) of antibody IC14-30 (as shown in FIG. 7) or antibody 11-25 (as shown in FIG. 9). In some embodiments, the binding protein is an antibody or antigen binding fragment thereof comprising three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 1'-25 (as shown in FIG. 9). In some embodiments, the binding protein further includes one or more framework regions from the heavy chain and/or light chain of antibody IC14-30 or antibody 11-25. In some embodiments, the antibody or antigen binding fragment thereof includes a constant region or a portion of a constant region, e.g., a constant region or portion thereof described herein.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In some embodiments, the level of MSLN may be determined by contacting the MSLN with a second binding agent of MSLN, e.g., a second binding agent that binds to a region of MSLN that is different from the first binding agent, comprising a detectable label. In an additional embodiment, the detectable label is a radioactive label, a fluorescent label, a luminescent label, a paramagnetic label, or an enzyme. In some embodiments, the detectable label is directly associated with the binding agent. In other embodiments, the label may be associated with an agent that binds to the binding agent. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody.

In some embodiments, the method may further comprise determining the level of MSLN in a body fluid more than once during treatment of kidney malfunction, e.g., peritoneal dialysis. In certain examples, the MSLN level may be determined weekly, monthly, every two or three months, every six months, or yearly.

In other embodiments, the method may further comprise selecting a treatment for the subject based upon the level of the MSLN in the peritoneal fluid. In some embodiments, the treatment selected may be peritoneal dialysis. In certain embodiments, if the MSLN level is more than a threshold level, e.g., the MSLN level is statistically the same or greater than, for example, a certain fraction of the reference standard, the treatment selected is peritoneal dialysis. In other embodiments, if the decrease in MSLN level is statistically less than a certain fraction of the reference standard or decreases below the reference standard, the treatment selected is hemodialysis.

In another example, a method of detecting MPF in a body fluid of a subject is described. In some examples, the method comprises contacting the body fluid of the subject to at least one antibody, or antigen binding fragment thereof, that binds to a first epitope of MPF, contacting the body fluid to a second antibody, or antigen binding fragment thereof, comprising a detectable label that binds to a second epitope of MPF different from the first epitope, and detecting the level of MPF in the body fluid using the first and second antibodies or antibody fragments. The detectable label can be, e.g., a radioactive label, a fluorescent label, a luminescent label, a paramagnetic label, or an enzyme.

In certain embodiments, the method may comprise comparing the determined level of MPF in the body fluid (or more particularly, the level in peritoneal fluid) to a reference standard, e.g., the level of MPF detected in the blood prior to or at the time of initiation of dialysis treatment, or detected in the peritoneal fluid at the initiation or within one, two, three months of initiating dialysis treatment for kidney malfunction in the subject.

In another embodiment, the method may further comprise selecting a treatment for the subject based upon the level of MPF in the peritoneal fluid. In some examples, the treatment selected may be peritoneal dialysis. In some embodiments, if the MPF level is greater than a threshold level, e.g., the MPF level is statistically the same or greater than, for example, a certain fraction of the reference standard, the treatment selected is peritoneal dialysis. In some embodiments, if the MPF level is statistically less than the same fraction of the reference standard or decreases below the same fraction of the reference standard, the treatment selected is hemodialysis.

In certain embodiments, the antibody or antigen binding fragment thereof that binds to MPF, e.g., binds to at least 10 or at least 20 contiguous amino acids shown in SEQ ID NO.: 1 or a variant thereof. In some embodiments, the antibody, or antigen binding fragment thereof, is an antibody or antigen binding fragment described herein. In some embodiments, the antibody, or antigen binding fragment thereof, comprises three heavy chain (HC) complementarity determining regions (CDRs) of antibody 20-10 (as shown in FIG. 2) or antibody 41-28 (as shown in FIG. 4). In some embodiments, the antibody, or antigen binding fragment thereof, comprises three light chain (LC) complementarity determining regions (CDRs) of antibody 20-10 (as shown in FIG. 3) or antibody 41-28 (as shown in FIG. 5). In some embodiments, the antibody, or antigen binding fragment thereof, comprises three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the antibody, or antigen binding fragment thereof, further includes one or more framework regions from the heavy chain and/or light chain of antibody 20-10 or antibody 41-28. In some embodiments, the antibody, or antigen binding fragment thereof, includes a constant region or a portion of a constant region, e.g., a constant region or portion of a constant region described herein.

In some embodiments, the method includes contacting MPF in a sample of peritoneal fluid with a first antibody that removes the MPF from the sample and a second binding antibody that comprises a detectable label. In certain examples, the method may further comprise exposing the peritoneal fluid to MPF labeled with a detectable label. In some embodiments, the method may further comprise determining the level of MPF in the body fluid more than once during treatment of kidney malfunction, e.g., peritoneal dialysis. In certain examples, the MPF level may be determined weekly, monthly, every two or three months, every six months or yearly.

In an additional example, a method of detecting MSLN in a body fluid of a subject is described. In some examples, the method comprises contacting the body fluid of the subject to at least one antibody, or antigen binding fragment thereof, that binds to a first epitope of MSLN, contacting the body fluid to a second antibody, or antigen binding fragment thereof, comprising a detectable label that binds to a second epitope of MSLN different from the first epitope, and detecting the level of MSLN in the body fluid using the first and second antibodies or antibody fragments.

In certain embodiments, the method may further comprise comparing the determined level of MSLN in the peritoneal fluid to a reference standard, e.g., the level of MSLN detected in the blood prior to or at the time of initiation of dialysis treatment, or detected in the peritoneal fluid at the initiation or within one, two, three months of initiating dialysis treatment for kidney malfunction in the subject. In other embodiments, the method may further comprise selecting a treatment for the subject based upon the level of the MSLN in the peritoneal fluid. In some embodiments, the treatment selected may be peritoneal dialysis. In certain embodiments, if the MSLN level is more than a threshold level, e.g., the MSLN level is statistically the same or greater than, for example, a certain fraction of the reference standard, the treatment selected is peritoneal dialysis. In other embodiments, if the decrease in MSLN level is statistically less than the same fraction of the reference standard or decreases below the same fraction of the reference standard, the treatment selected is hemodialysis.

In certain examples, an antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the antibody or antigen binding fragment thereof comprises three heavy chain (HC) complementarity determining regions (CDRs) of IC14-30 (as shown in FIG. 6) or antibody 11-25 (as shown in FIG. 8). In some embodiments, the antibody or antigen binding fragment thereof comprises three light chain (LC) complementarity determining regions (CDRs) of antibody IC14-30 (as shown in FIG. 7) or antibody 11-25 (as shown in FIG. 9). In some embodiments, the antibody or antigen binding fragment thereof comprises three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the antibody or antigen binding fragment thereof includes one or more framework regions from the heavy chain and/or light chain of antibody 14-30 or antibody 11-25. In some embodiments, the antibody or antigen binding fragment thereof includes a constant region or a portion of a constant region, e.g., a constant region or portion thereof described herein.

In some embodiments, the method may further comprise determining the level of MSLN in the body fluid more than once during treatment of kidney malfunction, e.g., peritoneal dialysis. In certain examples, the MSLN level may be determined weekly, monthly, every two or three months, every six months or yearly.

In certain embodiments, an assay for assessing continuation of peritoneal dialysis for a subject in need of dialysis, the assay comprising contacting peritoneal dialysis fluid, e.g., spent peritoneal fluid, from the subject to at least one binding agent, e.g., an antibody or antigen binding fragment thereof, specific for MPF or MSLN, determining the level of MPF or MSLN in the peritoneal dialysis fluid, and assessing whether to provide peritoneal dialysis or hemodialysis based on the determined level of MPF or MSLN, or based on a decrease in the determined level of MPF or MSLN compared to a reference standard, e.g., a level of MPF and/or MSLN determined at an earlier time, for example the individual's initial level of MPF or MSLN at the onset of peritoneal dialysis treatment or one, two or three months after peritoneal dialysis treatment is initiated is described.

In certain embodiments, the antibody, or antigen binding fragment thereof, specific for MPF binds to MPF, e.g., binds to at least 10 or at least 20 contiguous amino acids shown in SEQ ID NO.: 1 or a variant thereof. In some embodiments, the antibody, or antigen binding fragment thereof, is an antibody or antigen binding fragment described herein. In some embodiments, the antibody or antigen binding fragment thereof specific for MPF comprises three heavy chain (HC) complementarity determining regions (CDRs) of antibody 20-10 (as shown in FIG. 2) or antibody 41-28 (as shown in FIG. 4). In some embodiments, antibody, or antigen binding fragment thereof, specific for MPF comprises three light chain (LC) complementarity determining regions (CDRs) of antibody 20-10 (as shown in FIG. 3) or antibody 41-28 (as shown in FIG. 5). In some embodiments, the antibody, or antigen binding fragment thereof, specific for MPF comprises three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the antibody, or antigen binding fragment thereof, specific for MPF includes one or more framework regions from the heavy chain and/or light chain of antibody 20-10 or antibody 41-28. In some embodiments, the antibody, or antigen binding fragment thereof, specific for MPF includes a constant region or a portion of a constant region, e.g., a constant region or portion thereof described herein.

In certain examples, the antibody, or antigen binding fragment thereof, specific for MSLN binds to, e.g., binds to at least 10 or at least 20 contiguous amino acids shown in SEQ ID NO.: 2 or a variant thereof. In some embodiments, the antibody, or antigen binding fragment thereof, specific for MSLN is an antibody or antigen binding fragment described herein. In some embodiments, the antibody, or antigen binding fragment thereof, specific for MSLN comprises three heavy chain (HC) complementarity determining regions (CDRs) of IC14-30 (as shown in FIG. 6) or antibody 11-25 (as shown in FIG. 8). In some embodiments, the antibody, or antigen binding fragment thereof, specific for MSLN comprises three light chain (LC) complementarity determining regions (CDRs) of antibody IC14-30 (as shown in FIG. 7) or antibody 11-25 (as shown in FIG. 9). In some embodiments, the antibody, or antigen binding fragment thereof, specific for MSLN comprises three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the antibody, or antigen binding fragment thereof, specific for MSLN includes one or more framework regions from the heavy chain and/or light chain of antibody IC14-30 or antibody 11-25. In some embodiments, the antibody, or antigen binding fragment thereof, specific for MSLN includes a constant region or a portion of a constant region, e.g., a constant region or portion thereof described herein.

In some embodiments, the method further comprises discontinuing peritoneal dialysis treatment if the determined level of MPF or MSLN is about 20%, 30%, 40%, 50% or more lower as compared to a reference standard. In some examples, hemodialysis is administered after discontinuing of the peritoneal dialysis treatment. In some embodiments, the method comprises detecting the level of MPF or MSLN using another antibody comprising a detectable label.

In another embodiment, a method of selecting a dialysis treatment is provided. In certain examples, the method comprises selecting peritoneal dialysis if an MPF level in peritoneal fluid is above, for example, a certain fraction of a reference standard, and selecting hemodialysis if the MPF level in the peritoneal fluid is below a certain fraction of a reference standard. In some examples, the reference standard value may be based, at least in part, on a change from an initial MPF value measured at the initiation of or within one, two or three months from the initiation of dialysis treatment. For example, if the MPF level is 50%, 40%, 30%, 20% or less than the reference standard value, then peritoneal dialysis may be discontinued and hemodialysis may be initiated.

In an additional aspect, a method of selecting a dialysis treatment is provided. In certain examples, the method comprises selecting peritoneal dialysis if an MSLN level in peritoneal fluid is above a certain fraction of a reference standard, and selecting hemodialysis if the MSLN level in the peritoneal fluid is below a certain fraction of reference standard. In some examples, the reference standard may be based, at least in part, on a change from an initial MSLN value measured at the initiation of or within one, two, three months from the initiation of dialysis treatment. For example, if the MSLN level is 50%, 40%, 30%, 20% or less than the reference standard, then peritoneal dialysis may be discontinued and hemodialysis may be initiated.

In another aspect, a method of assessing the suitability of continued peritoneal dialysis treatment is described. In certain examples, the method comprises continuing peritoneal dialysis if an MPF level in peritoneal fluid is above a certain fraction of a reference standard, and discontinuing peritoneal dialysis if the MPF level in the peritoneal fluid is below a certain fraction of a reference standard. In some examples, the reference standard may be based, at least in part, on a change from an initial MPF value measured at the initiation of dialysis treatment or within one, two three months from the initiation of dialysis treatment. For example, if the MPF level is 50%, 40%, 30%, 20% or less than the reference standard value, then peritoneal dialysis may be discontinued. In certain examples, hemodialysis may be initiated if peritoneal dialysis is discontinued.

In an additional embodiment, a method of assessing the suitability of continued peritoneal dialysis treatment is described. In certain examples, the method comprises continuing peritoneal dialysis if an MSLN level in peritoneal fluid is above a certain fraction of a reference standard, and discontinuing peritoneal dialysis if the MSLN level in the peritoneal fluid is below a certain fraction of a reference standard. In some examples, the reference standard may be based, at least in part, on a change from an initial MSLN value measured at the initiation of dialysis treatment or within one, two, three months of initiating dialysis treatment. For example, if the MSLN level is 50%, 40%, 30%, 20% or less than the reference standard, then peritoneal dialysis may be discontinued. In certain examples, hemodialysis may be initiated if peritoneal dialysis is discontinued.

Kits

In certain embodiments, kits configured to detect the presence and/or level of MPF or MSLN in a body fluid sample are provided. The kits may be configured in many different ways including single or multiple antibodies, standards, buffers, reagents and the like. Illustrative configurations are described below.

In certain examples, a kit for assessing the presence and/or level of MSLN, MPF, or fragments thereof, in peritoneal fluid obtained from a patient is provided. In certain examples, the kit comprises a first binding protein (for example, e.g., an antibody) for binding the Mesothelin or MPF peptide or a fragment thereof, and an instructional material that describes contacting peritoneal fluid with the first agent. The format of the kit is not critical—many standard formats can be used, such as ELISA, latex bead aggregation, and surface plasmon resonance formats. The kit can include a Mesothelin or MPF peptide for use as a positive control. Of course, the kit can also include reagents for assessing other known markers of pathological conditions of mesothelial membranes or tissues or organs within mesothelial cavities, as well as reagents for assessing the performance of dialytic fluid exchange.

In other examples, kits for detecting the presence and/or level of mesothelin or MPF peptides in a spent peritoneal dialysis solution sample obtained from a mammal (e.g., a human patient) is provided. The kit comprises a first agent (for example, a binding protein) for binding the mesothelin or MPF peptide, a second agent for assessing binding of the respective peptide with the agent, and an instructional material for using the first agent and the second agent. Embodiments of such kits can be used, for example, to determine if a subject is at increased risk of developing a pathological condition of the peritoneum. For example, the kit can comprise a labeled compound or agent capable of determining the amount of mesothelin or MPF peptides in a spent peritoneal dialysis solution sample. Kits can include instructions for assessing whether the tested subject is suffering from or is at risk of developing a pathological condition if the amount of mesothelin or MPF peptides is below a normal level or has decreased by a certain factor compared to an initial level, established, for example, by measurement of the respective analyte in the same patient's blood or spent peritoneal dialysis solution at a previous time, for example prior to or shortly after the initiation of peritoneal dialysis treatment.

In embodiments where the kit includes an antibody, the kit can comprise, for example: (1) a first antibody (for example, attached to a solid support) which specifically binds with mesothelin or MPF peptides and, optionally, (2) a second, different antibody which specifically binds with either the same peptide (for example, at a epitope distinct from the epitope at which the first antibody binds) or the first antibody and is conjugated to a detectable agent. Alternatively, the kit can comprise the first antibody and a labeled ligand of the first antibody. After contacting the first antibody with a patient's spent peritoneal dialysis solution sample, binding of the labeled ligand with the first antibody can be assessed in a competition-type assay, as described herein.

In some examples, the kits can further comprise reagents and/or instructions for assessing occurrence in spent peritoneal dialysis solution or serum or another body fluid of the patient another marker indicative of occurrence of a pathological condition in the patient, including but not limited to uremic toxins or indicators of uremic toxicity, markers indicative of inflammatory reaction, solute exchange across the peritoneal membrane, and markers of bacterial and fungal infection, ions and small organic molecules whose balance may be disturbed due to the kidney dysfunction, such as potassium, calcium, creatinine, CRP, as well as glucose degradation products, advanced glycosylation end products, or other markers of damage inflicted by specific components of peritoneal dialysis solution such as glucose, or by diseases associated with chronic kidney failure, such as diabetes mellitus.

In certain embodiments, the kits (and the methods described herein) can be used alone to assess occurrence of a mesothelin or MPF peptide in spent peritoneal dialysis solution of a human patient or experimental animal, and such occurrence is indicative of the health and cytological integrity of the peritoneal mesothelium. If desired, a greater number of pathological or biochemical states can be detected to provide greater confidence in the status of the peritoneal cavity by using more than one marker of the status of the peritoneal cavity in the patient's spent peritoneal dialysis solution. Any additional marker(s) can include, but are not limited to, mesothelin, MPF, CA125, or other marker(s) normally found in spent peritoneal dialysis solution, in blood, or in other body fluids or in several of such fluids. The kits and methods described herein may also contain instructions pertaining to pathological or physical methods of assessing peritoneal health, such as peritoneal endoscopy, biopsy, or ultrasound imaging. The kits and methods described herein for assessing occurrence of mesothelin or MPF peptides in spent peritoneal dialysis solution can be used in conjunction with kits and methods of detecting the same or other mesothelin or MPF peptides in serum.

The kits and methods described herein for assessing occurrence of MSLN or MPF peptides in spent peritoneal dialysis solution obtained from a patient can be used to assess the likelihood that the patient will develop a pathological condition for a component of the peritoneal cavity. Detection of a pronounced decreased accumulation of mesothelin or MPF peptides in a patient's spent peritoneal dialysis solution is an indication that the patient is more likely to develop complications from peritoneal dialysis treatment early on than an otherwise identical patient in whose spent peritoneal dialysis solution the accumulation of MSLN or MPF decreases less. It is recognized that the difference between being afflicted with a condition, the earliest stages of the condition, and enhanced susceptibility to the condition may be substantially indistinguishable. Nonetheless, the outcome of each of these processes is development of the condition to the detriment of the patient's health. For this reason, assessment of any of these states using the kits and methods disclosed herein is useful.

In some examples, the kits may include mesothelin or MPF specific antibodies that can be used diagnostically or prognostically to monitor mesothelin or MPF levels in serum or spent peritoneal dialysis solution fluid of patients with kidney disease as part of a clinical testing procedure, for example, to determine the efficacy of a given treatment regimen.

In other embodiments, the kits and methods described herein can be used to determine whether an agent (for example, an agonist, antagonist, peptidomimetic, protein, peptide, nucleic acid, small molecule, or other therapeutic candidate) can be administered to a subject in order to alleviate, inhibit, reverse, or prevent peritoneal complications from peritoneal dialysis treatment. For example, such methods can be used to determine whether a specific peritoneal dialysis solution, an agent or class of agents added to peritoneal dialysis solution before performing peritoneal dialysis, or an agent or class of agent administered to the patient systematically (orally, intravenously, intraperitoneally or otherwise), can prevent the deterioration of the peritoneal mesothelium during peritoneal dialysis treatment, or can reverse such deterioration during ongoing peritoneal dialysis treatment or after peritoneal dialysis has been discontinued. Such kits can, for example, assist in avoiding the painful and dangerous peritoneal complications that frequently develop after long-term peritoneal dialysis treatment.

Detecting the antibodies used in the kits may be facilitated by coupling the antibody to a detectable substance. Examples of detectable substances include various enzymes, prosthetic groups, fluorescent materials, luminescent materials, bioluminescent materials, paramagnetic materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride orphycoerythrin; an example of a luminescent material includes luminol; examples of bioluminescent materials include luciferase, luciferin, and aequorin, and examples of suitable radioactive material include I, S or H. Illustrative paramagnetic labels include, but are not limited to, spin labels, paramagnetic metals and other species having an unpaired electron. Such components may come with the kit or may be obtained separately. In some examples, one or more antibodies may be pre-labeled such that the end-user can immediately use the components of the kit.

Use of standardized assay apparatus permits automation of the method described herein. For example, many different standardized assay containers are known, such as 24-, 48-, 96-, and 384-well plastic plates. Where these containers are adapted to fit a robotic apparatus, automated analysis of samples can be achieved, permitting high-throughput screening of many samples in a relatively short time. Automated assay apparatus and containers adapted for their use in computer-controlled assays are known in the art and will be readily adapted by the person of ordinary skill in the art, given the benefit of this disclosure, for the kits and methods described herein.

In certain examples, the components of the kits may be prepackaged in a cartridge, vials of other forms to facilitate use by an end-user. For example, one or more antibodies may be packaged in cartridge form such that the cartridge can be attached to a multiple stem pipette to eject the antibodies into a well-plate. In some examples, the cartridge may have eight tubes each including substantially the same amount of antibody such that antibody may be deposited in a single step into eight wells of a well-plate. Of course, other numbers of tubes including, but not limited to, two, four, eight, twelve, sixteen or more may be included in a cartridge as well. In some examples, a cartridge including pre-packaged standards may be included such that deposition of the contents of each tube provides a different concentration of standard in different wells of a microtiter plate. This pre-packaging can reduce pipetting errors and overall contamination of the standards.

In another embodiment, a kit for use in detecting the level of MPF in a body fluid (or more particularly, the level in peritoneal fluid), the kit comprising a first binding agent that binds to an epitope of MPF is provided.

In certain embodiments, the binding agent is selected from a small molecule and a protein (e.g., a ligand, antibody or antigen binding fragments thereof). In some embodiments, the binding protein is an antibody or antigen binding fragment thereof that binds to MPF, e.g., binds to at least 10 or at least 20 contiguous amino acids shown in SEQ ID NO.: 1 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 4). In some embodiments, the binding protein is an antibody or antigen binding fragment thereof comprising three light chain (LC) complementarity determining regions (CDRs) of antibody 20-10 (as shown in FIG. 3) or antibody 41-28 (as shown in FIG. 5). In some embodiments, the binding protein is an antibody or antigen binding fragment thereof comprising three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the binding protein further includes one or more framework regions from the heavy chain and/or light chain of antibody 20-10 or antibody 41-28. In some embodiments, the antibody or antigen binding fragment thereof includes a constant region or a portion of a constant region, e.g., a constant region or portion of a constant region described herein.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the kit includes an agent that binds to the binding agent wherein the an agent that binds to the binding agent is labeled. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody. In some embodiments, the kit may include instructions, e.g., instructions for use to determine the condition of the peritoneal cavity and/or peritoneal membrane.

In one embodiment, the kit may further comprise a second binding agent of MPF, for example an antibody or antigen binding fragment thereof that is effective to bind to a different epitope than the first binding agent. In certain examples, the second binding agent may be an antibody, or antigen binding fragment thereof. In some examples, the second binding agent comprises a detectable label. In certain examples, the detectable label is a radioactive label, a fluorescent label, a luminescent label, a paramagnetic label, or an enzyme. In certain embodiments, the kit may further comprise a detectable label that can be coupled to the first binding agent or the second binding agent or both. In some examples, the detectable label is a radioactive label, a fluorescent label, a luminescent label, a paramagnetic label, or an enzyme. In other examples, the kit may comprise a set of MPF standards for use in constructing a standard curve. In some examples, the MPF standards are recombinant MPF. In some examples, the kit may comprise MPF comprising a detectable label. In certain examples, the detectable label is a radioactive label, a fluorescent label, a luminescent label, a paramagnetic label, or an enzyme.

In an additional embodiment, a kit for use in detecting the level of MSLN in a body fluid (or more particularly, the level in peritoneal fluid), the kit comprising a first binding agent that binds to an epitope of MSLN is provided.

In certain examples, the binding agent is selected from a small molecule and a protein (e.g., a ligand, antibody or antigen binding fragments thereof). In some embodiments, the binding protein is an antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the binding protein is an antibody or antigen binding fragment thereof comprising three heavy chain (HC) complementarity determining regions (CDRs) of IC14-30 (as shown in FIG. 6) or antibody 11-25 (as shown in FIG. 8). In some embodiments, the binding protein is an antibody or antigen binding fragment thereof comprising three light chain (LC) complementarity determining regions (CDRs) of antibody IC14-30 (as shown in FIG. 7) or antibody 11-25 (as shown in FIG. 9). In some embodiments, the binding protein is an antibody or antigen binding fragment thereof comprising three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the binding protein further includes one or more framework regions from the heavy chain and/or light chain of antibody IC14-30 or antibody 11-25. In some embodiments, the antibody or antigen binding fragment thereof includes a constant region or a portion of a constant region, e.g., a constant region or portion thereof described herein.

In certain embodiments, the binding agent can be directly or indirectly labeled, e.g., with a detectable label. In some examples, the detectable label may be a radioactive label, a fluorescent label, a luminescent label, a paramagnetic label, or an enzyme. In some embodiments, the detectable label is directly associated with the binding agent. In other embodiments, the kit further includes an agent that binds to the binding agent and, e.g., the agent that binds the binding agent is labeled. For example, in one embodiment, the binding agent may be an antibody or antigen binding fragment thereof and the antibody or antigen binding fragment can be contacted with a labeled agent that binds to the antibody or antigen binding fragment thereof. A non-limiting example of such an agent is an anti-idiotypic antibody. In some embodiments, the kit may include instructions, e.g., instructions for use to determine the condition of the peritoneal cavity and/or peritoneal membrane.

In one embodiment, the kit may further comprise a second binding agent of MSLN, for example an antibody or antigen binding fragment thereof that is effective to bind to a different epitope or site than the first binding agent. In some examples, the second binding agent comprises a detectable label. In certain examples, the detectable label is a radioactive label, a fluorescent label, a luminescent label, a paramagnetic label, or an enzyme. In certain embodiments, the kit may further comprise a detectable label that can be coupled to the first binding agent or the second binding agent or both. In some examples, the detectable label is a radioactive label, a fluorescent label, a luminescent label, a paramagnetic label, or an enzyme. In other examples, the kit may comprise a set of MSLN standards for use in constructing a standard curve. In some examples, the MSLN standards are recombinant MSLN. In some examples, the kit may comprise MSLN comprising a detectable label. In certain examples, the detectable label is a radioactive label, a fluorescent label, a luminescent label, a paramagnetic label, or an enzyme.

In another embodiment, a kit for detecting the level of MPF or MLSN in a body fluid (or more particularly, the level in peritoneal fluid) is provided. In certain examples, the kit comprises a first antibody, or antigen binding fragment thereof, effective to bind to MPF and a second antibody, or antigen binding fragment thereof, effective to bind to MSLN, e.g., at a different epitope than the first antibody or antigen binding fragment thereof.

In certain embodiments, the first antibody, or antigen binding fragment thereof, binds to MPF, e.g., binds to at least 10 or at least 20 contiguous amino acids shown in SEQ ID NO.: 1 or a variant thereof. In some embodiments, the antibody, or antigen binding fragment thereof, is an antibody or antigen binding fragment described herein. In some embodiments, the first antibody or antigen binding fragment thereof comprising three heavy chain (HC) complementarity determining regions (CDRs) of antibody 20-10 (as shown in FIG. 2) or antibody 41-28 (as shown in FIG. 4). In some embodiments, the first antibody or antigen binding fragment thereof comprising three light chain (LC) complementarity determining regions (CDRs) of antibody 20-10 (as shown in FIG. 3) or antibody 41-28 (as shown in FIG. 5). In some embodiments, the first antibody or antigen binding fragment thereof comprising three heavy chain (HC) complementarity determining regions (CDRs) of antibody 20-10 (as shown in FIG. 2) or antibody 41-28 (as shown in FIG. 4) and three light chain (LC) complementarity determining regions (CDRs) of antibody 20-10 (as shown in FIG. 3) or antibody 41-28 (as shown in FIG. 5). In some embodiments, the first antibody includes one or more framework regions from the heavy chain and/or light chain of antibody 20-10 or antibody 41-28. In some embodiments, the first antibody or antigen binding fragment thereof includes a constant region or a portion of a constant region, e.g., a constant region or portion thereof described herein.

In certain examples, the second antibody or antigen binding fragment thereof that binds to MSLN, e.g., binds to at least 10 or at least 20 contiguous amino acids shown in SEQ ID NO.: 2 or a variant thereof. In some embodiments, the antibody or antigen binding fragment thereof is an antibody or antigen binding fragment described herein. In some embodiments, the second antibody or antigen binding fragment thereof comprises three heavy chain (HC) complementarity determining regions (CDRs) of IC14-30 (as shown in FIG. 6) or antibody 11-25 (as shown in FIG. 8). In some embodiments, the second antibody or antigen binding fragment thereof comprises three light chain (LC) complementarity determining regions (CDRs) of antibody IC14-30 (as shown in FIG. 7) or antibody 11-25 (as shown in FIG. 9). In some embodiments, the second antibody or antigen binding fragment thereof comprises three heavy chain (HC) complementarity determining regions (CDRs) of antibody IC14-30 (as shown in FIG. 6) or antibody 11-25 (as shown in FIG. 8) and three light chain (LC) complementarity determining regions (CDRs) of antibody IC14-30 (as shown in FIG. 7) or antibody 11-25 (as shown in FIG. 9). In some embodiments, the second antibody or antigen binding fragment thereof includes one or more framework regions from the heavy chain and/or light chain of antibody IC14-30 or antibody 11-25. In some embodiments, the second antibody or antigen binding fragment thereof includes a constant region or a portion of a constant region, e.g., a constant region or portion thereof described herein.

In certain embodiments, the kit may include instructions for using the first and second antibodies. In some examples, one of the first and second antibodies comprises a detectable label. In certain examples, the detectable label is a radioactive label, a fluorescent label, a luminescent label, a paramagnetic label, or an enzyme. In other examples, the kit may include a detectable label that can be coupled to the first antibody or the second antibody or both. In some examples, the detectable label is a radioactive label, a fluorescent label, a luminescent label, a paramagnetic label, or an enzyme. In one embodiment, the kit may include a set of MPF standards for use in constructing a standard curve. In some examples, the MPF standards are recombinant MPF. In other examples, the kit may include a set of MSLN standards. In some examples, the MSLN standards are recombinant MSLN. In additional examples, the kit may comprise MPF comprising a detectable label, MSLN comprising a detectable label, or both. In some examples, the detectable label is a radioactive label, a fluorescent label, a luminescent label, a paramagnetic label, or an enzyme.

Antibody and Antigen Production

Certain embodiments disclosed herein are directed to proteins that bind to MPF or MSLN and include at least one immunoglobin variable region. For example, the MPF or MSLN binding protein can include a heavy chain (HC) immunoglobulin variable domain sequence and a light chain (LC) immunoglobulin variable domain sequence. A number of illustrative MPF and MSLN binding proteins are described herein and shown in the figures.

In certain examples, the MPF or MSLN binding protein may be an isolated protein (for example, at least 70, 80, 85, 90, 91, 92, 93, 94, 95, 96, 97, 98, or 99% free of other proteins).

In some examples, the MPF or MSLN binding proteins may be antibodies. For example, MPF or MSLN antibodies may have their HC and LC variable domain sequences included in a single polypeptide (e.g., scFv) or on different polypeptides (e.g., IgG or Fab).

Several MPF and Mesothelin antibodies are known in the art. For example, Clone 41-28 in combination with Clone 20-10 are known to detect MPF with high sensitivity, and Clone 11-25 in combination with Clone MN are known to detect mesothelin with high sensitivity (Iwahori K, Osaki T, Serada S, Fujimoto M, Suzuki H, Kishi Y, Yokoyama A, Hamada H, Fujii Y, Yamaguchi K, Hirashima T, Matsui K, Tachibana I, Nakamura Y, Kawase I, Naka T. Megakaryocyte potentiating factor as a tumor marker of malignant pleural mesothelioma: Evaluation in comparison with mesothelin. Lung Cancer, 2008, in press).

In certain embodiments described herein, clone 11-25 in combination with Clone IC14-30 can detect mesothelin with high sensitivity. Thus, for example, clone IC14-30 can be bound to a substrate and used as a 'capture' antibody to bind mesothelin peptide present in a patient's spent dialysis fluid under appropriate antibody-binding conditions, and clone 11-25 can be detectably labeled and contacted with the 'capture' antibody after contacting the 'capture' antibody with the patient's spent dialysis fluid.

Similarly, clone 20-10 can be bound to a substrate and used as a 'capture' antibody to bind MPF peptide present in a patient's spent dialysis fluid under appropriate antibody-binding conditions, and clone 41-28 can be detectably labeled and contacted with the 'capture' antibody after contacting the 'capture' antibody with the patient's spent dialysis fluid.

Binding of the detectably labeled antibody with the 'capture' antibody indicates that the mesothelin or MPF peptide was present in the patient's spent dialysis fluid. Analysis of the amount of detectable label co-localized with the 'capture' antibody can provide the level of the peptide that is present.

It is known that there exist some variants of MPF and mesothelin, specifically splice variants and polymorphisms summarized in Swiss-Prot entry Q13421 (entry version 64, last modified on Mar. 18, 2008). From these sequences, it is apparent that the sequences shown in FIGS. 1 and 2 (SEQ ID NOs: 1 and 2, respectively) represent useful portions of mesothelin and MPF peptides. Antibodies raised against all or a portion (for example, 10, 20, 50, or 200 consecutive residues) of either of these sequences can be expected to bind specifically with a broad range of mesothelin or MPF peptides, including those that occur in the spent dialysis solution of peritoneal dialysis patients.

Methods of generating antibodies are well known and only briefly summarized here. An immunogen typically is used to prepare antibodies by immunizing a suitable (for example, immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent. Mesothelin or MPF, or a fragment thereof, can be used as an immunogen to generate antibodies using standard techniques for polyclonal and monoclonal antibody preparation. A fragment of Mesothelin or MPF, when used as an immunogen, desirably comprises at least 10 (preferably 12, 15, 20, 50, 100, or 200 or more) amino acid residues of the amino acid sequence of any of SEQ ID NOs: 1-2 or the amino acid sequence of another variant of mesothelin or MPF.

Appropriate Mesothelin or MPF peptides for generation of antibodies useful in the kits and methods described herein comprise a portion of at least 20 consecutive amino acid residues that is at least 90% (preferably at least 95% or 100%) identical to 20 consecutive residues of a sequence selected from the group consisting of SEQ ID NOs: 1-2 or the know variants described in Swiss-Prot entry Q13421.

The MPF or MSLN may be recombinantly expressed to provide suitable amounts of MPF or MSLN for use in producing the antibodies. For example, a recombinant MPF protein may be produced by amplifying the coding part for amino acids 1-288 from the cDNA encoding the transcript variant 1 for human mesothelin (Genbank accession no. NM_005823) using Taq DNA polymerase (or other suitable polymerase) and suitable primers (for example, 5'-CGGAATTCGCCGC-CACCATGGCCTTGCCAACGGCTCGACCCCTGTTG-3' (SEQ ID NO: 23) and 5'-GCTCTAGAGATGGTTCCGT-TCAGGCTGCCGCCAGGATGG-3' (SEQ ID NO:_24)), as described, for example, in the Iwahori et al. article (Lung Cancer 2008). The amplicon may be inserted into a EcoRI/XbaI site of mammalian expression plasmid pcDNA3.1/myc-His (Invitrogen, Carlsbad, Calif.) and transfected into HEK 293T cells by lipofection (Lipofectamine-2000; Invitrogen) The culture supernatant may be applied to a TALON resin according to the manufacturer's instructions (Clontech, Mountain View, Calif.). The purified MPF protein may be obtained by dialysis using 4.0 liters of PBS and kept frozen at $-80°$ C. until it is used as an immunogen or as a standard in the methods, kits and devices disclosed herein.

Similarly, MSLN may be produced by amplifying the coding part for amino acids 297-580 of the same cDNA discussed in reference to the MPF and using primers (for example, 5'-AAATTTCCCAAGCTTGTGGAGAAGA-CAGCCTGTCCTTCAGGCAAG-3'(SEQ ID NO: 25) and 5'-AAGGAAAAAAGCGGCCGCGCCCTGTAGC-CCCAGCCCCAGCGTGTCCAG-3'(SEQ ID NO: 26)). The amplified DNA may be inserted into the HindIII/NotI site of expression vector pSecTag2B (Invitrogen). The plasmid DNA may be transfected into HEK 293T cells, and recombinant MSLN may be produced in the culture supernatant and purified as described in reference to the recombinant MPF. The recombinant MSLN may be used as an immunogen or as a standard in the methods, kits and devices disclosed herein.

Polyclonal antibodies can be prepared as described above by immunizing a suitable subject with a polypeptide as an immunogen. The antibody titer in the immunized subject can be monitored over time by standard techniques, such as with an enzyme linked immunosorbent assay (ELISA) using immobilized polypeptide. If desired, the antibody molecules can be harvested or isolated from the subject (for example, from the blood or serum of the subject) and further purified by well-known techniques, such as protein A chromatography to obtain the IgG fraction.

At an appropriate time after immunization, for example, when the specific antibody titers are highest, antibody-producing cells can be obtained from the subject and used to prepare monoclonal antibodies by standard techniques, such as the hybridoma technique originally described by Kohler and Milstein (1975) Nature 256: 495-497, the human B cell hybridoma technique (Kozbor et al. (1983) Immunol. Today 4: 72), the EBV-hybridoma technique (Cole et al. (1985), Monoclonal Antibodies and Cancer Therapy, Alan R. Liss, Inc., pp. 77-96) or trioma techniques. The technology for producing hybridomas is well known (see generally Current Protocols in Immunology (1994) Coligan et al. (Eds.) John Wiley & Sons, Inc., New York, N.Y.). Hybridoma cells producing a monoclonal antibody are detected by screening the hybridoma culture supernatants for antibodies that bind the polypeptide of interest, for example, using a standard ELISA assay.

In one embodiment, monoclonal antibodies may be prepared against MPF and MSLN by immunizing 4-6 week old BALB/c mice with an appropriate immunogen (for example, either MPF or MSLN) at selected times, for example, days 0, 7, 14, and 16. Following the last injection, lymphocytes of the spleen may be collected and fused with P3U1 myeloma cells in a 50% polyethylene glycol 4000 solution (Wako, Osaka, JP) on day 18. The fused cells may be plated on 96-well plates with RPMI-1640 medium containing 15% fetal calf serum, an antibiotic and HAT solution (Invitrogen). After 10 days incubation at 37° C. with 5% CO2 in a humidified environment, culture supernatants may be collected and screened for their ability to bind to the immunizing antigen using, for example, an ELISA assay. Positive hybridoma colonies may be expanded and subcloned by limiting dilution.

As an alternative to preparing monoclonal antibody-secreting hybridomas, a monoclonal antibody directed against a polypeptide can be identified and isolated by screening a recombinant combinatorial immunoglobulin library (for example, an antibody phage display library, or yeast display library, mammalian cell display library or bacterial cell display library, or similar) with the polypeptide of interest. Kits for generating and screening phage display libraries are commercially available (for example, the Pharmacia Recombinant Phage Antibody System, Catalog No. 27-9400-01; and the Stratagene SURFZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9: 1370-1372; Hay et al. (1992) Hum. Antibod. Hybridomas 3: 81-85; Huse et al. (1989) Science 246: 1275-1281; Griffiths et al. (1993) EMBO J. 12: 725-734.

Recombinant antibodies, such as chimeric and humanized monoclonal antibodies, comprising both human and non-human portions, which can be made using standard recombinant DNA techniques, may also be produced and used. Such chimeric and humanized monoclonal antibodies can be produced by recombinant DNA techniques known in the art, for example using methods described in PCT Publication No. WO 87/02671; European Patent Application 184, 187; European Patent Application 171,496; European Patent Application 173,494; PCT Publication No. WO 86/01533; U.S. Pat. No. 4,816,567; European Patent Application 125,023; Better et al. (1988) Science 240: 1041-1043; Liu et al. (1987) Proc. Natl. Acad. Sci. USA 84: 3439-3443; Liu et al. (1987) J. Immunol. 139: 3521-3526; Sun et al. (1987) Proc. Natl. Acad. Sci. USA 84: 214-218; Nishimura et al. (1987) Cancer Res. 47: 999-1005; Wood et al. (1985) Nature 314: 446-449; and Shaw et al. (1988) J. Natl. Cancer Inst. 80: 1553-1559); Morrison (1985) Science 229: 1202-1207; Oi et al. (1986) Bio/Techniques 4: 214; U.S. Pat. No. 5,225,539; Jones et al. (1986) Nature 321: 552-525; Verhoeyan et al. (1988) Science 239: 1534; and Beidler et al. (1988) J. Immunol. 141: 4053-4060.

In an additional embodiment, an antibody or antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MPF is provided. In one embodiment, the HC includes three CDRs from antibody 20-10. In one embodiment, the LC includes three CDRs from antibody 20-10. In some embodiments, the antibody or antigen binding fragment thereof includes one or more frameworks regions from the HC and/or LC of antibody 20-10.

In another embodiment, an antibody or antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MPF is provided. In one embodiment, the HC includes three CDRs from antibody 41-28. In one embodiment, the LC includes three CDRs from antibody 41-28. In some embodiments, the antibody or antigen binding fragment thereof includes one or more frameworks regions from the HC and/or LC of antibody 41-28.

In an additional embodiment, an antibody or antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MSLN is provided. In one embodiment, the HC includes three CDRs from antibody IC14-30. In one embodiment, the LC includes three CDRs from antibody IC14-30. In some embodiments, the antibody or antigen binding fragment thereof includes one or more frameworks regions from the HC and/or LC of antibody IC14-30.

In another embodiment, an antibody or antigen binding fragment thereof comprising a heavy chain (HC) immunoglobulin variable domain sequence and a light chain (LC) immunoglobulin variable domain sequence, in which the HC and LC immunoglobulin variable domain sequences provide an antigen binding site that binds to a MSLN is provided. In one embodiment, the HC includes three CDRs from antibody 11-25. In one embodiment, the LC includes three CDRs from antibody 11-25. In some embodiments, the antibody or antigen binding fragment thereof includes one or more frameworks regions from the HC and/or LC of antibody 11-25.

Certain specific examples are described in more detail below to illustrate further some of the novel, features, aspects and embodiments of the technology described herein.

EXAMPLE 1

Production of Recombinant MPF Protein

Recombinant MPF protein was produced by amplifying the part coding for amino acids 1-288 from the cDNA encoding the transcript variant 1 for human mesothelin precursor protein (GenBank accession no. NM_005823) by polymerase chain reaction, using the primers 5'-CGGAATTCGC-CGCCACCATGGCCTTGCCAACGGCTC-GACCCCTGTTG-3' (SEQ ID NO: 23) and 5'-GCTCTAGAGATGGTCCGTTCAGGCTGC-CGCCAGGATGG-3' (SEQ ID NO: 27). The amplified DNA was inserted into the EcoRI/XbaI site of mammalian expression plasmid pcDNA3.1/myc-His (Invitrogen) and transfected into HEK 293T cells. MPF protein was purified from the culture supernatant of the transfected cells using a TALON resin. The purified MPF protein thus obtained was dialyzed with PBS twice and kept frozen at −80° C. until use.

EXAMPLE 2

Production of Recombinant Mesothelin Protein

Recombinant mesothelin protein was produced by amplifying the part coding for amino acids 297-580 from the cDNA encoding the transcript variant 1 for human mesothelin precursor protein (GenBank accession no. NM_005823) by polymerase chain reaction, using the primers 5'-AAATTTC-CCAAGCTTGTGGAGAAGACAGCCTGTC-CTTCAGGCAAG-3' (SEQ ID NO: 25) and 5'-AAG-GAAAAAAGCGGCCGCGCCCTGTAGCCCCAGCCCC AGCGTGTCCAG-3' (SEQ ID NO: 26). The amplified DNA was inserted into the HindIII/NotI site of expression vector pSecTag2B (Invitrogen). It should be noted that amino acids 297-580 of the protein encoded by clone NM 005823 are shared as a common sequence by isoforms 1 and 3 of human mesothelin, as described by Scholler et al. (Proc. Natl. Acad. Sci. USA. 1999; 96(20):11531-6). The mesothelin expression plasmid was transfected into HEK 293T cells. Mesothelin protein was purified from the culture supernatant of the transfected cells using a TALON resin. The purified mesothelin protein thus obtained was dialyzed with PBS twice and kept frozen at −80° C. until use.

EXAMPLE 3

Generation of MPF Antibodies

To generate monoclonal antibodies (mAbs) against MPF, 4- to 6-week old BALB/c mice were immunized with the purified recombinant MPF protein intraperitoneally on day 0, 7, 14, and 16 (10 micrograms/shot). On the 18$^{th}$ day after the 4th immunization, lymphocytes of spleen were collected and fused with P3U1 myeloma cells with 50% polyethylene glycol 4000 solution. The fused cells were plated on 96-well plates with RPMI-1640 medium containing 15% fetal calf serum, penicillin/streptomycin and HAT solution (Invitrogen). After 10 days incubation at 37° C. with 5% $CO_2$ in a humidified environment, culture supernatants were collected and screened for the ability to bind to the immunizing antigen by an indirect ELISA using the recombinant MPF protein. Selected positive hybridoma colonies were expanded and subcloned by limiting dilution. Subcloned hybridomas were cultured and the isotype of subcloned antibodies was determined using an isostrip kit from Roche. Antibody purification was carried out by protein A affinity chromatography. Following a competition assay for the immunogens among obtained clones, clone 20-10 and clone 41-28 (both IgG1 Kappa) were selected to construct an ELISA for the detection of MPF ELISA. Clone 41-28 was biotinylated using ECL Protein Biotination Module from GE Healthcare.

EXAMPLE 4

Generation of Mesothelin Antibodies

To generate monoclonal antibodies (mAbs) against mesothelin, 4- to 6-week old BALB/c mice were immunized with the purified recombinant mesothelin protein intraperitoneally on day 0, 7, 14, and 16 (10 micrograms/shot). On the 18$^{th}$ day after the 4th immunization, lymphocytes of spleen were collected and fused with P3U1 myeloma cells with 50% polyethylene glycol 4000 solution. The fused cells were plated on 96-well plates with RPMI-1640 medium containing 15% fetal calf serum, penicillin/streptomycin and HAT solution (Invitrogen). After 10 days incubation at 37° C. with 5% $CO_2$ in a humidified environment, culture supernatants were collected and screened for the ability to bind to the immunizing antigen by an indirect ELISA using the recombinant mesothelin protein. Selected positive hybridoma colonies were expanded and subcloned by limiting dilution. Subcloned hybridomas were cultured and the isotype of subcloned antibodies was determined using an isostrip kit from Roche. Antibody purification was carried out by protein A affinity chromatography. Following a competition assay for the immunogens among obtained clones, clone 11-25 (IgG2b Kappa) and clone IC14-30 (IgG1 Kappa) were selected to construct an ELISA for the detection of MPF ELISA. Clone 11-25 was biotinylated using ECL Protein Biotination Module from GE Healthcare.

EXAMPLE 5

Characterization of MPF Antibodies

To determine the nucleotide sequence of CDR regions of anti-MPF monoclonal antibodies, 20-10 and 41-28, total RNA was collected from the hybridoma that produces 20-10 and 4'-28, respectively, generated according to Example 3. Messenger RNAs in the collected total RNA were reverse-transcribed to complementary DNA using Oligo $(dT)_{12-18}$ (SEQ ID NO: 28) Primers (purchased from Invitrogen). From this DNA, the nucleotide sequence of immunoglobulin variable region was amplified by PCR technique using primers 5'-ATGGGATGGAGCGGGGTCTTTCTCTT-3' (SEQ ID NO: 29) and 5'-CAGTGGATAGACAGATGGGGG-3' (SEQ ID NO: 30) for heavy chain of 20-10, and primers 5'-ATGAGTGTGCTCACTCAGGTCCTGGCGTTG-3' (SEQ ID NO: 31) and 5'-ACTGGATGGTGGGAAGATGG-3' (SEQ ID NO: 32) for light chain of 20-10, and primers 5'-ATGGCT-TGGGTGTGGACCTTGCTATTCCTG-3' (SEQ ID NO: 33) and 5'-CAGTGGATAGACAGATGGGGG-3' (SEQ ID NO: 30) for heavy chain of 41-28, and primers 5'-ATGAAGT-TGCCTGTTAGGCTGTTGGTGCTG-3' (SEQ ID NO: 34) and 5'-ACTGGATGGTGGGAAGATGG-3' (SEQ ID NO: 32) for light chain of 41-28. The amplified cDNA was inserted into the EcoRV site of pBluescript II KS(+) plasmid (Stratagene). Subsequently the sequence of the VH and VL region was analyzed by a gene sequencer (3130/3100-Avant™ Genetic Analyzer Capillary Arrays; Applied Biosystems). Determination of FR1, 2, 3, and 4, and CDR1, 2, and 3 regions were performed using IgG blast (NCBI database) and SEQUENCES OF PROTEINS OF IMMUNOLOGICAL INTEREST, VOL. I, 5$^{th}$ EDITION, 1991; NIH Publication No. 91-3242 (Elvin A. Kabat, et al.).

EXAMPLE 6

Characterization of MSLN Antibodies

To determine the nucleotide sequence of CDR region of anti-MSLN monoclonal antibodies, IC14-30 and 11-25, total RNA was collected from the hybridoma that produces IC14-30 and 11-25, respectively, generated according to Example 4. Messenger RNAs in the collected total RNA were reverse-transcribed to complementary DNA using Oligo $(dT)_{12-18}$ (SEQ ID NO: 28) Primers (purchased from Invitrogen). From this DNA, the nucleotide sequence of immunoglobulin variable region sequence was amplified by PCR technique using primers 5'-ATGAAATGCAGCTGGGGCATCTTCTTC-3' (SEQ ID NO: 35) and 5'-CAGTGGATAGACA-GATGGGGG-3' (SEQ ID NO: 30) for heavy chain of IC14-30, and primers 5'-ATGGGCTTCAAGATGGAGTCACA-GATCCAGG-3' (SEQ ID NO: 36) and 5'-ACTGGATGGTGGGAAGATGG-3' (SEQ ID NO: 32) for light chain of IC14-30, and primers 5'-ATGGCTGTCT-TGGGGCTGCTCTTCTGC-3' (SEQ ID NO: 37) and 5'-CAGTGGATAGACTGATGGGGG-3' (SEQ ID NO: 38) for heavy chain of 11-25, and primers 5'-ATGAAGTTGCCT-GTTAGGCTGTTGGTGCTG-3' (SEQ ID NO: 34) and 5'-ACTGGATGGTGGGAAGATGG-3' (SEQ ID NO: 32) for light chain of 11-25. The amplified cDNA was inserted into the EcoRV site of pBluescript II KS(+) plasmid (Stratagene). Subsequently the sequence of the VH and VL region was analyzed by a gene sequencer (3130/3100-Avant™ Genetic Analyzer Capillary Arrays; Applied Biosystems). Determination of FR1, 2, 3, and 4, and CDR1, 2, and 3 regions were performed using IgG blast (NCBI database) and SEQUENCES OF PROTEINS OF IMMUNOLOGICAL INTEREST, VOL. I, 5$^{th}$ EDITION, 1991; NIH Publication No. 91-3242 (Elvin A. Kabat, et al.).

EXAMPLE 7

Sandwich ELISA Assay for Assessing MPF in a Sample

A typical assay used to detect MPF peptides in a spent peritoneal dialysis solution sample is now described. Assays were performed in a 96-well clear, flat-bottom microtiter plate (Nunc) that had been previously coated with 100 microliters of capture antibody (monoclonal antibody clone 20-10 as described in Iwahori et al., Lung Cancer, 2008, referenced herein) at a concentration of 5 micrograms per milliliter in carbonate-bicarbonate buffer, overnight at 4 degrees Celsius. Each well was then blocked by filling it with a with 200 microliters phosphate buffered saline containing 1.0% BSA for 2 hours at room temperature, after which time the BSA suspension was removed from the wells.

Standard solutions were prepared by diluting the recombinant MPF protein to 2, 1, 0.5, 0.25, 0.125, 0.0624 and 0.0313 nanograms per milliliter. Sample diluent used for standard dilutions as well as detection antibodies was a 1% (w/v) suspension of BSA in phosphate buffered physiological saline.

Figure 10A:
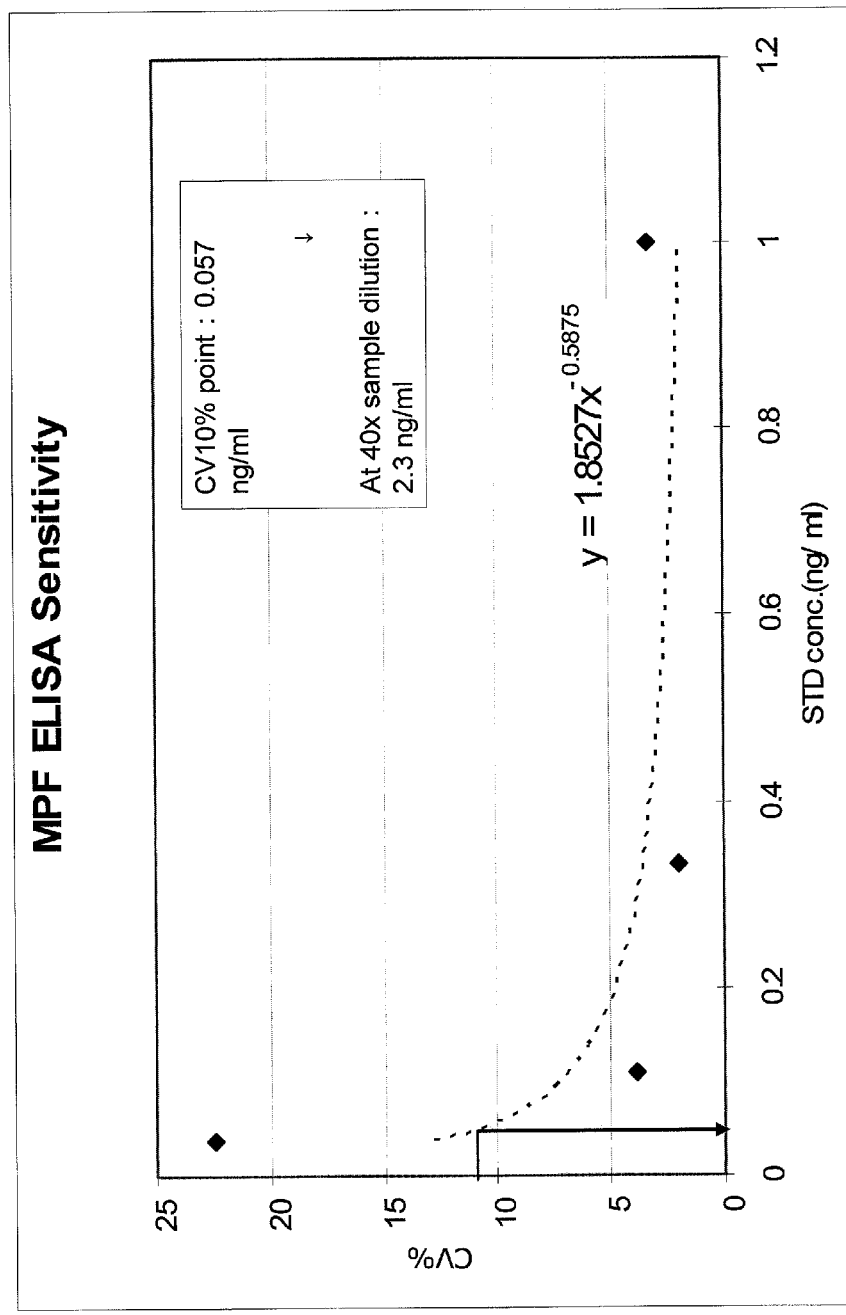
FIG. 10A shows the results of a functional sensitivity test of an assay used to detect MPF and FIG. 10B shows the results of a functional sensitivity test of an assay used to detect mesothelin (MSLN), in accordance with certain examples.

To perform the assay, 50 microliters of each standard dilution, controls, a spent peritoneal dialysis fluid sample, or a diluted spent peritoneal dialysis fluid sample was added to individual wells. Typically, spent peritoneal dialysis samples were diluted 40-fold in sample diluent. The plate was incubated for 1 hour at room temperature, and the wells were thereafter washed with tris-buffered saline containing 0.05% (v/v) Tween20 surfactant. 100 Microliters of a 0.25 microgram per milliliter suspension of horse radish peroxidase conjugated monoclonal antibody 41-28 was added to each well. The plate was incubated for 1 hour at room temperature, and wells were thereafter washed with tris-buffered saline containing 0.013% (v/v) Tween20 surfactant. 100 Microliters of 3,3',5,5'-tetramethylbenzidine (TMB; achromogenic substrate for horseradish peroxidase) was added to each well to generate signal. The plate was incubated for 30 minutes at room temperature before adding 100 microliters of TMB Stop solution (0.36 normal sulfuric acid) to halt the peroxidase reaction. Blue color generated by the action of the peroxidase on TMB was assessed using a plate reader to measure the absorbance at 450 nanometers. The sensitivity of the MPF ELISA was determined by measuring serial 3-fold dilutions of concentration standard, and measuring each concentration in 8 separate wells. The mean OD and standard deviation of each concentration was determined. The lower limit of quantitative measurement was determined as the concentration below which the standard deviation is expected to be 10% of the mean, and was found to be 57 picogram per milliliter, which is equal to 2.28 nanograms per milliliter at 40 fold sample dilution (shown in FIG. 10A).

EXAMPLE 8

Sandwich ELISA Assay for Assessing Mesothelin in a Sample

A typical assay used to detect mesothelin peptides in a spent peritoneal dialysis solution sample is now described. Assays were performed in a 96-well clear, flat-bottom microtiter plate (Nunc) that had been previously coated with 100 microliters of capture antibody (monoclonal antibody clone IC14-30 at a concentration of 5 micrograms per milliliter in carbonate-bicarbonate buffer, overnight at 4 C. Each well was then blocked by filling it with a with 200 microliters phosphate buffered saline containing 1.0% BSA for 2 hours at room temperature, after which time the BSA suspension was removed from the wells.

Standard solutions were prepared by diluting the recombinant Mesothelin protein to 25, 12.5, 6.25, 3.125, 1.5625, 0.78125 and 0.390626 nanograms per milliliter. Sample diluent used for standard dilutions as well as detection antibodies was a 1% (w/v) suspension of BSA in PBS.

Figure 10B:
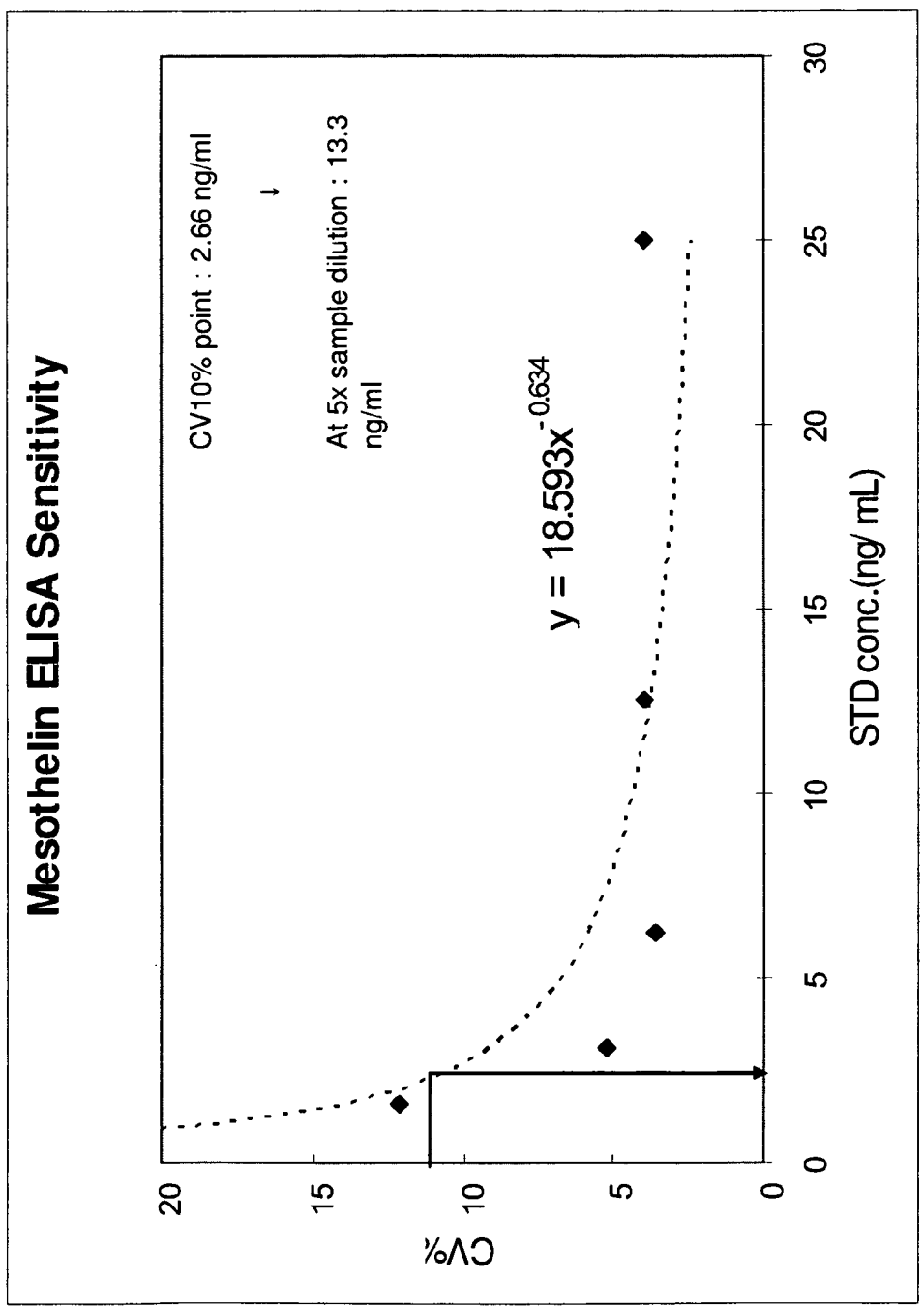

To perform the assay, 100 microliters of each standard dilution, controls, a spent peritoneal dialysis fluid sample, or a diluted spent peritoneal dialysis fluid sample was added to individual wells. Typically, spent peritoneal dialysis samples were diluted 5-fold in sample diluent The plate was incubated for 1 hour at room temperature, and the wells were thereafter washed with tris-buffered saline containing 0.013% (v/v) Tween20 surfactant. 100 Microliters of a 0.3 microgram per milliliter suspension of biotinylated monoclonal antibody 11-25 was added to each well. After incubating the plate for 1 hour at room temperature and thereafter washing each well with tris-buffered saline containing Tween20 surfactant, 100 microliters of a 1:20000 dilution of Streptavidin-horseradish peroxidase (obtained from DAKO) was added to each well, and the plate was incubated for 1 hour at room temperature. 100 Microliters of 3,3',5,5'-tetramethylbenzidine (TMB; achromogenic substrate for horseradish peroxidase) was added to each well to generate signal. The plate was incubated for 30 minutes at room temperature before adding 100 microliters of TMB Stop solution (0.36 normal sulfuric acid) to halt the peroxidase reaction. Blue color generated by the action of the peroxidase on TMB was assessed using a plate reader to measure the absorbance at 450 nanometers. The sensitivity of the MSLN ELISA was determined by measuring serial 2-fold dilutions of concentration standard, and measuring each concentration in 8 separate wells. The mean OD and standard deviation of each concentration was determined. The lower limit of quantitative measurement was determined as the concentration below which the standard deviation is expected to be 10% of the mean, and was found to be 2.66 nanogram per milliliter, which is equal to 13.3 nanograms per milliliter at 5 fold sample dilution (shown in FIG. 10B). The detection limit was determined as the lowest concentration where the mean+2 standard deviations is lower than the mean−2 standard deviation of the next higher concentration. The detection limit was found to be 0.78 nanogram per milliliter.

EXAMPLE 9

Figure 11:
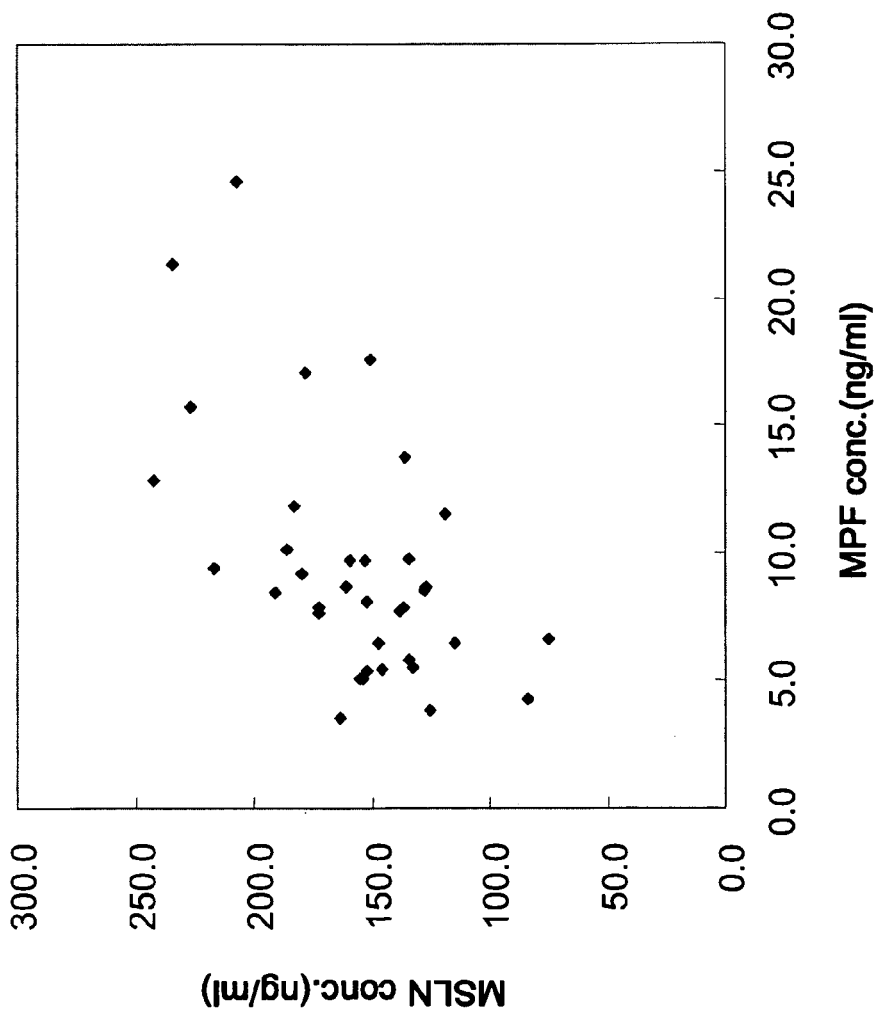
FIG. 11 shows the mesothelin and MPF protein detected in the serum of 38 healthy Japanese persons, in accordance with certain examples.

Detection of MPF Peptides and Mesothelin Peptides in the Serum of Healthy Individuals Both MPF and mesothelin were quantified in serum taken from 38 healthy Japanese persons. Informed consent was obtained and blood was drawn from healthy volunteers, allowed to coagulate, and solid matter was removed by centrifugation. The ELISA used for quantifying MPF in serum is described in Example 7, and the ELISA used to quantify MSLN in serum is the one described in Iwahori et al. (Lung Cancer, 2008), which uses a different capture antibody but the same detection antibody as described in Example 7. The result is shown in FIG. 11.

Most healthy individuals had detectable amounts of both proteins in their serum. The correlation was determined to be $R^2=0.31$ (Pearson's Coefficient). This data demonstrates that the two biomarkers are detectable in the bloodstream of healthy individuals, and that both biomarkers are clearly distinct and diagnostically not equivalent.

EXAMPLE 10

Decrease Over Time of MPF Peptides and Mesothelin Peptides Accumulation in the Peritoneal Dialysis Fluid of Individual Patients Peritoneal dialysis is one of the treatments for end-stage renal disease and serves as a replacement for lost kidney function.

310 dialysis samples were obtained from 84 patients who had given informed consent on different dates (ranging from 1 to 32 draws per patient). The night before a visit to the clinic, patients injected 2000 ml peritoneal dialysis solution into their peritoneal cavity. At the clinic, 9-10 hours after injection, the peritoneal dialysis was removed, samples were taken for analysis and the remainder was discarded. Samples were kept below −40 degree Celsius until used.

Samples were diluted as described in Examples 7 and 8 (1:40 in PBS with 1% BSA for measuring MPF, and 1:5 in PBS with 1% BSA for measuring MSLN). Dialysis solution was used as a negative control. 100 Microliters of each sample dilution was tested in the assay described in Example 1. The results, shown in FIG. 14, indicate that MPF is useful as a marker in peritoneal dialysis fluid.

43 out of the 84 patients monitored had no known incidence of peritonitis prior to or during the observation period, for 22 out of those patients, spent peritoneal dialysis solution samples over a 3 month interval (91-98 days) could be obtained. These patients had already carried out peritoneal dialysis for between 154-3884 days at the start of this study. FIG. 12 demonstrates that, the concentration of both mesothelin and MPF in the spent peritoneal dialysis buffer of individual patients decreased. The decrease of both MSLN and MPF was highly significant ($p<0.001$, as determined with the dependent Student's T-test) Furthermore, it was apparent that those of the 22 patients with a shorter history of peritoneal dialysis tended to have higher overall levels of both markers (data not shown but similar to FIG. 14).

EXAMPLE 11

Accumulation of MPF Peptides and Mesothelin Peptides in Peritoneal Dialysis Fluid During Acute Inflammatory Insult With the method described in Example 10, MPF and mesothelin in spent dialysis solution was followed over the course of peritonitis due to bacterial or fungal infection in several patients and compared to inflammatory markers including white blood cell count and Matrix Metalloproteinase 2 (MMP-2) concentrations in the peritoneal dialysis fluid.

As shown in FIG. 13, for a typical patient MPF and Mesothelin concentration in the spent peritoneal dialysis solution decreased rapidly at the time of inflammation, but in some cases recovered to pre-infectious levels after the inflammatory infection had subsided.

EXAMPLE 12

Accumulation of MPF Peptides and Mesothelin Peptides in Peritoneal Dialysis Fluid is Lower in Long-Time Peritoneal Dialysis Patients The samples in this studies were grouped into four groups according to the time length of time of peritoneal dialysis treatment:

Group 1: <1 Year Group: 20 patients with CAPD treatment time 240+/−81 days (mean+/−standard deviation), aged 59+/−12 years;

Group 2: 1-3 Years Group: 34 patients with CAPD treatment time 584+/−168 days, aged 63+/−13 years;

Group 3: 3-5 Years Group: 12 patients with CAPD treatment time 1385+/−225 days, aged 67+/−12 years; and Group 4: >5 Years Group: 18 patients with CAPD treatment time 2557+/−633 days, aged 64+/−9 years.

Figure 14:
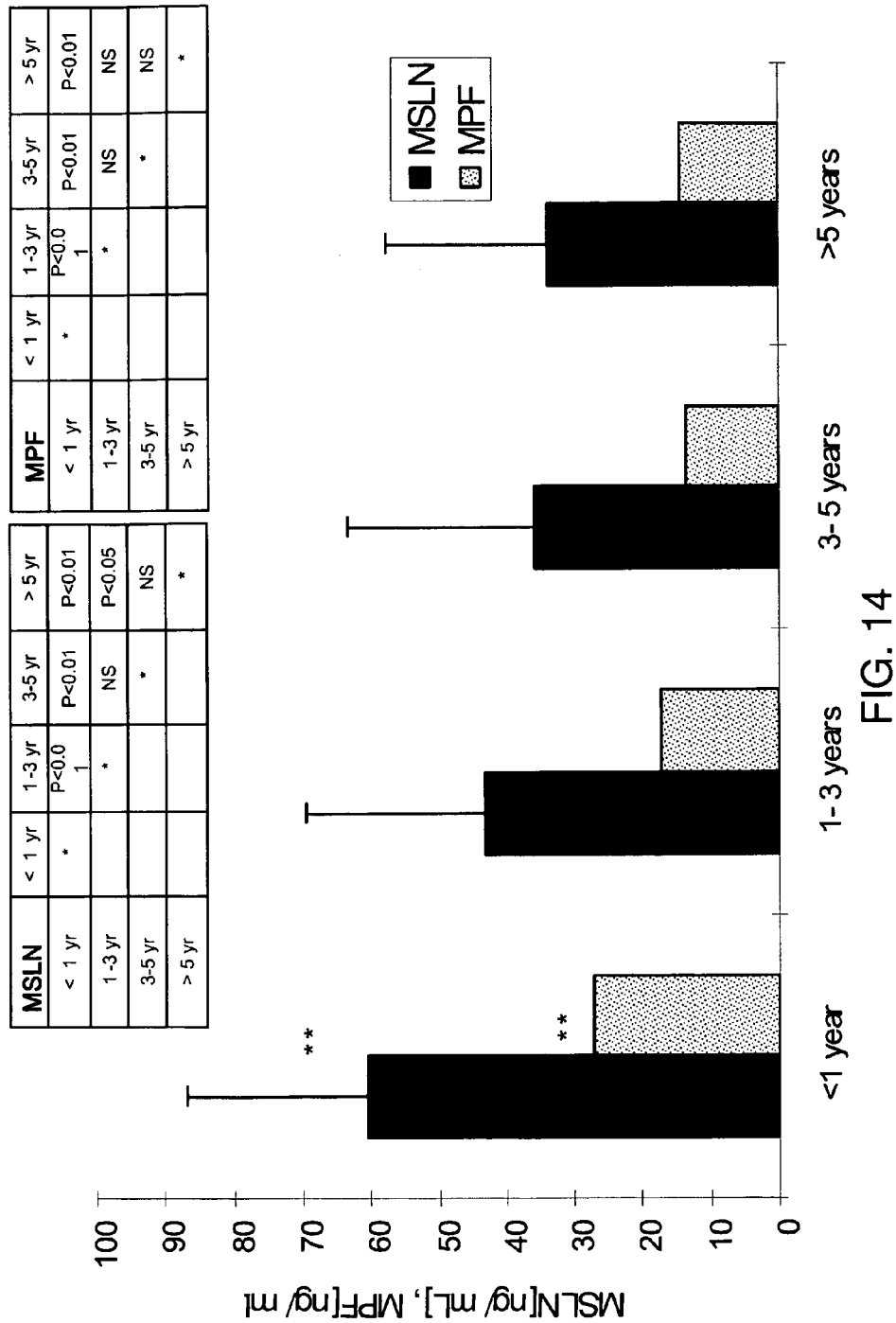
FIG. 14 is a bar graph showing that on average, less MPF and mesothelin accumulates in the dialysis buffer of patients who have carried out peritoneal dialysis for a longer time, in accordance with certain examples.

MPF and Mesothelin levels were determined as described in Example 10. As shown in FIG. 14, the average mesothelin and MPF accumulation in peritoneal dialysis solution decreased steadily with treatment duration. The decrease was statistically significant (P<0.01, Mann-Whitney U test) between Group 1 and any other group for both MSLN and MPF, and between Group 2 and Group 4 for MSLN.

EXAMPLE 13

Mesothelin and MPF in Spent Dialysate Predicts Treatment Method Survival

In a retrospective analysis of therapeutic outcome, the 18 patients who had been on peritoneal dialysis for more than 5 years (Group 4 of Example 10) were divided into patients still on peritoneal dialysis treatment at the end of the observation period (12 patients, 33 samples) and patients who had to discontinue peritoneal dialysis treatment (6 patients, 47 samples).

MPF and Mesothelin levels were determined as described in Example 10. As shown in FIG. 15, both mesothelin and MPF were significantly (P<0.005) lower in samples from patients who had to discontinue peritoneal dialysis treatment, compared to the group who continued peritoneal dialysis treatment. These data indicate that both mesothelin and MPF accumulation in the peritoneal dialysis solution are predictive indicators of the treatment outcome. Consequently, these markers provide useful guidance to discontinue peritoneal dialysis in time for a patient to avoid serious and irreversible damage to the peritoneum, including chronic pain and organ obstruction. The disclosure of every patent, patent application, and publication cited herein is hereby incorporated herein by reference in its entirety. In addition, the citation of certain publications discussed in the specification are listed below and also incorporated herein by reference.

When introducing elements of the examples disclosed herein, the articles "a," "an," "the" and "said" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples. Should the meaning of the terms of the patents or publications incorporated herein by reference conflict with the meaning of the terms used in this disclosure, the meaning of the terms in this disclosure are intended to be controlling.

Although certain aspects, examples and embodiments have been described of this disclosure, that additions, substitutions, modifications, and alterations of the disclosed illustrative aspects, examples and embodiments are possible.

---

What is claimed is:

1. A composition comprising a heavy chain immunoglobulin variable domain sequence and a light chain immunoglobulin variable domain sequence, in which the heavy chain and the light chain immunoglobulin variable domain sequences provide an antigen binding site that binds to a MSLN; and the heavy chain and the light chain immunoglobulin variable domain sequences comprise heavy chain complementarity determining regions CDR1, CDR2 and CDR3 and light chain complementary determining regions CDR1, CDR2 and CDR3 of SEQ ID NO: 9 and SEQ ID NO: 10.

2. A composition comprising a heavy chain immunoglobulin variable domain sequence and a light chain immunoglobulin variable domain sequence, in which the heavy chain and the light chain immunoglobulin variable domain sequences provide an antigen binding site that binds to a MSLN; and the heavy chain and the light chain immunoglobulin variable domain sequences comprise heavy chain complementarity determining regions CDR1, CDR2 and CDR3 and light chain complementary determining regions CDR1, CDR2 and CDR3 of SEQ ID NO: 11 and SEQ ID NO: 12.

3. A kit for use in detecting the level of MSLN in a body fluid, the kit comprising: the composition of claim 1; and instructions for using the antibody to detect the level of MSLN in the body fluid or peritoneal fluid.

4. The kit of claim 3, further comprising the composition of claim 2.

5. A kit for use in detecting the level of MSLN in a body fluid, the kit comprising: the composition of claim 2; and instructions for using the antibody to detect the level of MSLN in the body fluid or peritoneal fluid.

* * * * *

SEQUENCE LISTING

```
<160> NUMBER OF SEQ ID NOS: 38

<210> SEQ ID NO 1
<211> LENGTH: 262
<212> TYPE: PRT
<213> ORGANISM: Homo sapiens

<400> SEQUENCE: 1

Ser Arg Thr Leu Ala Gly Glu Thr Gly Gln Glu Ala Ala Pro Leu Asp
1               5                   10                  15

Gly Val Leu Ala Asn Pro Pro Asn Ile Ser Ser Leu Ser Pro Arg Gln
            20                  25                  30

Leu Leu Gly Phe Pro Cys Ala Glu Val Ser Gly Leu Ser Thr Glu Arg
        35                  40                  45

Val Arg Glu Leu Ala Val Ala Leu Ala Gln Lys Asn Val Lys Leu Ser
    50                  55                  60

Thr Glu Gln Leu Arg Cys Leu Ala His Arg Leu Ser Glu Pro Pro Glu
65                  70                  75                  80

Asp Leu Asp Ala Leu Pro Leu Asp Leu Leu Leu Phe Leu Asn Pro Asp
                85                  90                  95

Ala Phe Ser Gly Pro Gln Ala Cys Thr Arg Phe Phe Ser Arg Ile Thr
            100                 105                 110
```

```
Lys Ala Asn Val Asp Leu Leu Pro Arg Gly Ala Pro Glu Arg Gln Arg
            115                 120                 125

Leu Leu Pro Ala Ala Leu Ala Cys Trp Gly Val Arg Gly Ser Leu Leu
    130                 135                 140

Ser Glu Ala Asp Val Arg Ala Leu Gly Gly Leu Ala Cys Asp Leu Pro
145                 150                 155                 160

Gly Arg Phe Val Ala Glu Ser Ala Glu Val Leu Leu Pro Arg Leu Val
                165                 170                 175

Ser Cys Pro Gly Pro Leu Asp Gln Asp Gln Gln Glu Ala Ala Arg Ala
            180                 185                 190

Ala Leu Gln Gly Gly Pro Pro Tyr Gly Pro Ser Thr Trp Ser
    195                 200                 205

Val Ser Thr Met Asp Ala Leu Arg Gly Leu Leu Pro Val Leu Gly Gln
210                 215                 220

Pro Ile Ile Arg Ser Ile Pro Gln Gly Ile Val Ala Ala Trp Arg Gln
225                 230                 235                 240

Arg Ser Ser Arg Asp Pro Ser Trp Arg Gln Pro Glu Arg Thr Ile Leu
                245                 250                 255

Arg Pro Arg Phe Arg Arg
            260

<210> SEQ ID NO 2
<211> LENGTH: 311
<212> TYPE: PRT
<213> ORGANISM: Homo sapiens

<400> SEQUENCE: 2

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
                20                  25                  30

Asp Ala Ala Leu Leu Ala Thr Gln Met Asp Arg Val Asn Ala Ile Pro
            35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Ala Pro Arg Arg Pro Leu Pro Gln Val Ala Thr Leu Ile
        115                 120                 125

Asp Arg Phe Val Lys Gly Arg Gly Gln Leu Asp Lys Asp Thr Leu Asp
    130                 135                 140

Thr Leu Thr Ala Phe Tyr Pro Gly Tyr Leu Cys Ser Leu Ser Pro Glu
145                 150                 155                 160

Glu Leu Ser Ser Val Pro Pro Ser Ser Ile Trp Ala Val Arg Pro Gln
                165                 170                 175

Asp Leu Asp Thr Cys Asp Pro Arg Gln Leu Asp Val Leu Tyr Pro Lys
            180                 185                 190

Ala Arg Leu Ala Phe Gln Asn Met Asn Gly Ser Glu Tyr Phe Val Lys
    195                 200                 205

Ile Gln Ser Phe Leu Gly Gly Ala Pro Thr Glu Asp Leu Lys Ala Leu
    210                 215                 220
```

```
Ser Gln Gln Asn Val Ser Met Asp Leu Ala Thr Phe Met Lys Leu Arg
225                 230                 235                 240

Thr Asp Ala Val Leu Pro Leu Thr Val Ala Glu Val Gln Lys Leu Leu
            245                 250                 255

Gly Pro His Val Glu Gly Leu Lys Ala Glu Arg His Arg Pro Val
        260                 265                 270

Arg Asp Trp Ile Leu Arg Gln Arg Gln Asp Asp Leu Asp Thr Leu Gly
        275                 280                 285

Leu Gly Leu Gln Gly Gly Ile Pro Asn Gly Tyr Leu Val Leu Asp Leu
    290                 295                 300

Ser Met Gln Glu Ala Leu Ser
305                 310

<210> SEQ ID NO 3
<211> LENGTH: 8
<212> TYPE: PRT
<213> ORGANISM: Homo sapiens

<400> SEQUENCE: 3

Pro Gln Ala Pro Arg Arg Pro Leu
1               5

<210> SEQ ID NO 4
<211> LENGTH: 64
<212> TYPE: PRT
<213> ORGANISM: Homo sapiens

<400> SEQUENCE: 4

Val Gln Gly Gly Arg Gly Gly Gln Ala Arg Ala Gly Arg Ala Gly
1               5                   10                  15

Gly Val Glu Val Gly Ala Leu Ser His Pro Ser Leu Cys Arg Gly Pro
            20                  25                  30

Leu Gly Asp Ala Leu Pro Pro Arg Thr Trp Thr Cys Ser His Arg Pro
        35                  40                  45

Gly Thr Ala Pro Ser Leu His Pro Gly Leu Arg Ala Pro Leu Pro Cys
    50                  55                  60

<210> SEQ ID NO 5
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Trp Ser Gly Val Phe Leu Phe Leu Ala Ala Thr Ala Thr Gly
1               5                   10                  15

Val His Ser Gln Val Gln Leu Gln Gln Ser Gly Pro Glu Leu Val Arg
            20                  25                  30

Pro Gly Ala Ser Val Lys Met Ser Cys Lys Ala Ser Gly Tyr Thr Phe
        35                  40                  45

Thr Thr Tyr Trp Met His Trp Val Arg Gln Arg Pro Gly Gln Gly Leu
    50                  55                  60

Glu Trp Ile Gly Val Ile Asp Pro Ser Asn Asn Asp Ser Lys Leu Asn
65                  70                  75                  80

Gln Lys Phe Asn Asp Lys Ala Ser Leu Thr Val Asp Thr Ser Ser Asn
                85                  90                  95

Thr Ala Tyr Met Gln Leu Ser Ser Leu Thr Ser Glu Asp Ser Ala Val
            100                 105                 110
```

```
Tyr Tyr Cys Ala Arg Arg Leu Val Tyr Ala Met Asp Ser Trp Gly
            115                 120                 125

Gln Gly Thr Pro Val Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
            165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
            195                 200                 205

Ser Ser Thr Trp Pro Ser Glu Thr Val Thr Cys Asn Val Ala His Pro
            210                 215                 220

Ala Ser Ser Thr Lys Val Asp Lys Lys Ile Gly Ser Arg Ser Ala
225                 230                 235

<210> SEQ ID NO 6
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Val Leu Thr Gln Val Leu Ala Leu Leu Leu Leu Trp Leu Thr
1               5                   10                  15

Asp Ala Gly Cys Asp Ile Gln Met Thr Gln Ser Pro Ala Ser Leu Ala
            20                  25                  30

Ala Ser Val Gly Glu Thr Val Thr Ile Thr Cys Arg Ala Ser Glu Asn
        35                  40                  45

Ile Tyr Tyr Ser Leu Thr Trp Tyr Gln Gln Lys Gln Gly Arg Ser Pro
    50                  55                  60

Gln Leu Leu Ile Tyr Asn Ala Ile Asn Leu Glu Asp Gly Val Pro Ser
65                  70                  75                  80

Arg Phe Ser Gly Ser Gly Ser Gly Thr Gln Phe Ser Met Lys Ile Asn
                85                  90                  95

Ser Met Gln Pro Glu Asp Ser Ala Thr Tyr Phe Cys Lys Gln Ala Tyr
            100                 105                 110

Asp Val Pro Phe Thr Phe Gly Ser Gly Thr Lys Leu Glu Ile Lys Arg
            115                 120                 125

Ala Asp Ala Ala Pro Thr Val Ser Ile Phe Pro Pro Ser Ser
            130                 135                 140

<210> SEQ ID NO 7
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30
```

```
Pro Gly Glu Thr Val Lys Ile Ser Cys Lys Ala Ser Gly Tyr Thr Phe
         35                  40                  45

Thr His Tyr Gly Met Asn Trp Val Lys Gln Ala Pro Gly Lys Gly Leu
     50                  55                  60

Lys Trp Met Gly Trp Ile Asn Thr Tyr Thr Gly Glu Pro Ser Tyr Ala
 65                  70                  75                  80

Asp Asp Phe Lys Gly Arg Phe Ala Phe Ser Leu Glu Thr Ser Ala Ser
                 85                  90                  95

Thr Ala Tyr Leu Gln Ile Asn Asn Leu Lys Asn Glu Asp Met Ala Thr
            100                 105                 110

Tyr Phe Cys Ala Arg Arg Asp Tyr Gly Thr Ser His Trp Tyr Leu
            115                 120                 125

Asp Val Trp Gly Ala Gly Thr Thr Val Thr Val Ser Ser Ala Lys Thr
        130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
                180                 185                 190

Thr Phe Pro Ala Val Leu Gln Ser Asp Leu Tyr Thr Leu Ser Ser Ser
            195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Gly Ser
225                 230                 235                 240

Arg Ser Ala

<210> SEQ ID NO 8
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Phe
            35                  40                  45

Val His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Phe Tyr Tyr Cys
            100                 105                 110

Phe Gln Gly Ser His Val Pro Tyr Thr Phe Gly Gly Gly Thr Lys Leu
            115                 120                 125

Glu Ile Lys Arg Ala Asp Ala Ala Pro Thr Val Ser Ile Phe Pro Pro
        130                 135                 140

Ser Ser
```

<210> SEQ ID NO 9
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Lys Cys Ser Trp Gly Ile Phe Phe Leu Met Ala Val Val Thr Gly
1               5                   10                  15

Val Asn Ser Glu Val Gln Leu Gln Gln Ser Gly Ala Asp Leu Val Lys
            20                  25                  30

Pro Gly Ala Ser Val Lys Leu Ser Cys Ile Val Ser Ala Phe Asn Ile
        35                  40                  45

Glu Asp Thr Tyr Met His Trp Val Lys Gln Arg Pro Glu Gln Gly Leu
    50                  55                  60

Glu Trp Ile Gly Ser Ile Asp Pro Ala His Asp Asn Ala Lys Tyr Asp
65                  70                  75                  80

Pro Lys Phe Gln Val Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Lys Ser Asp Gly Phe Tyr Phe Asp Ser Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Gly Ser Arg Ser Ala
225                 230                 235

<210> SEQ ID NO 10
<211> LENGTH: 146
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Met Gly Phe Lys Met Glu Ser Gln Ile Gln Val Phe Val Phe Val Leu
1               5                   10                  15

Leu Trp Leu Ser Gly Ile Asp Gly Asp Ile Val Met Thr Gln Ser Gln
            20                  25                  30

Lys Phe Met Ser Thr Ser Val Gly Asp Arg Val Ser Ile Thr Cys Lys
        35                  40                  45

Ala Ser Gln Asn Val Arg Ser Ala Val Ala Trp Tyr Gln Gln Lys Pro
    50                  55                  60

Gly Gln Ser Pro Lys Ala Leu Ile Tyr Leu Ala Ser Asn Arg His Thr
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Asp Tyr Phe Cys
            100                 105                 110

Leu Gln His Trp Asn Tyr Pro Leu Ser Val Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser
145

<210> SEQ ID NO 11
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Val Leu Gly Leu Leu Phe Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ser Tyr Gly Val Gln Trp Val Arg Gln Pro Pro Gly Lys Gly Leu
    50                  55                  60

Glu Trp Leu Gly Val Ile Trp Ala Gly Gly Ser Thr Lys Tyr Asn Ser
65                  70                  75                  80

Ala Leu Met Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Asp Asp Tyr Arg Arg Thr Ser Leu Tyr Ala Met
        115                 120                 125        Met

Asp Tyr Trp Gly Gln Gly Thr Ser Val Thr Val Ser Ser Ala Lys Thr
    130                 135                 140

Thr Pro Pro Ser Val Tyr Pro Leu
145                 150

<210> SEQ ID NO 12
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

-continued

```
Val His Ser Asn Gly Asn Thr Tyr Leu His Trp Tyr Leu Gln Lys Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
                100                 105                 110

Ser Gln Ser Thr His Val Pro Tyr Thr Phe Gly Gly Gly Thr Lys Leu
            115                 120                 125

Glu Ile Lys Arg Ala Asp Ala Ala Pro Thr Val Ser Ile Phe Pro Pro
        130                 135                 140

Ser
145
```

<210> SEQ ID NO 13
<211> LENGTH: 6
<212> TYPE: PRT
<213> ORGANISM: Homo sapiens

<400> SEQUENCE: 13

```
Met Gln Glu Ala Leu Ser
 1               5
```

<210> SEQ ID NO 14
<211> LENGTH: 718
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(717)

<400> SEQUENCE: 14

```
atg gga tgg agc ggg gtc ttt ctc ttc ttg gca gca aca gct aca ggt     48
Met Gly Trp Ser Gly Val Phe Leu Phe Leu Ala Ala Thr Ala Thr Gly
 1               5                  10                  15 gtc cac tcc cag gtc caa ctg cag cag tct ggg cct gaa ctg gtg agg     96
Val His Ser Gln Val Gln Leu Gln Gln Ser Gly Pro Glu Leu Val Arg
            20                  25                  30 cct ggg gct tca gtg aag atg tcc tgc aag gct tca ggc tat acc ttc    144
Pro Gly Ala Ser Val Lys Met Ser Cys Lys Ala Ser Gly Tyr Thr Phe
        35                  40                  45 acc acc tac tgg atg cac tgg gtg aga cag agg cct gga caa ggc ctt    192
Thr Thr Tyr Trp Met His Trp Val Arg Gln Arg Pro Gly Gln Gly Leu
     50                  55                  60 gag tgg att ggc gtg att gat cct tcc aat aat gat tct aaa tta aat    240
Glu Trp Ile Gly Val Ile Asp Pro Ser Asn Asn Asp Ser Lys Leu Asn
 65                  70                  75                  80 cag aag ttc aac gat aag gcc tca ttg act gta gac aca tcc tcc aac    288
Gln Lys Phe Asn Asp Lys Ala Ser Leu Thr Val Asp Thr Ser Ser Asn
                 85                  90                  95 aca gcc tac atg cag ctc agc agc ctg aca tct gag gac tct gca gtc    336
Thr Ala Tyr Met Gln Leu Ser Ser Leu Thr Ser Glu Asp Ser Ala Val
                100                 105                 110 tat tac tgt gca aga cga ctg gtt tac tat gct atg gac tcc tgg ggt    384
Tyr Tyr Cys Ala Arg Arg Leu Val Tyr Tyr Ala Met Asp Ser Trp Gly
            115                 120                 125 caa gga acc cca gtc acc gtc tcc tca gcc aaa acg aca ccc cca tct    432
Gln Gly Thr Pro Val Thr Val Ser Ser Ala Lys Thr Thr Pro Pro Ser
```

```
gtc tat cca ctg gcc cct gga tct gct gcc caa act aac tcc atg gtg      480
Val Tyr Pro Leu Ala Pro Gly Ser Ala Ala Gln Thr Asn Ser Met Val
145                 150                 155                 160 acc ctg gga tgc ctg gtc aag ggc tat ttc cct gag cca gtg aca gtg      528
Thr Leu Gly Cys Leu Val Lys Gly Tyr Phe Pro Glu Pro Val Thr Val
                165                 170                 175 acc tgg aac tct gga tcc ctg tcc agc ggt gtg cac acc ttc cca gct      576
Thr Trp Asn Ser Gly Ser Leu Ser Ser Gly Val His Thr Phe Pro Ala
            180                 185                 190 gtc ctg cag tct gac ctc tac act ctg agc agc tca gtg act gtc ccc      624
Val Leu Gln Ser Asp Leu Tyr Thr Leu Ser Ser Ser Val Thr Val Pro
        195                 200                 205 tcc agc acc tgg ccc agc gag acc gtc acc tgc aac gtt gcc cac ccg      672
Ser Ser Thr Trp Pro Ser Glu Thr Val Thr Cys Asn Val Ala His Pro
    210                 215                 220 gcc agc agc acc aag gtg gac aag aaa att gga tcc aga tct gcg g         718
Ala Ser Ser Thr Lys Val Asp Lys Lys Ile Gly Ser Arg Ser Ala
225                 230                 235

<210> SEQ ID NO 15
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(426)

<400> SEQUENCE: 15 atg agt gtg ctc act cag gtc ctg gcg ttg ctg ctg ctg tgg ctt aca       48
Met Ser Val Leu Thr Gln Val Leu Ala Leu Leu Leu Leu Trp Leu Thr
1               5                   10                  15 gac gca gga tgt gac atc cag atg act cag tct cca gcc tcc ctg gct       96
Asp Ala Gly Cys Asp Ile Gln Met Thr Gln Ser Pro Ala Ser Leu Ala
            20                  25                  30 gca tct gtg gga gaa act gtc acc atc aca tgt cga gca agt gag aac      144
Ala Ser Val Gly Glu Thr Val Thr Ile Thr Cys Arg Ala Ser Glu Asn
        35                  40                  45 att tac tac agt tta aca tgg tat cag cag aag caa ggg aga tct cct      192
Ile Tyr Tyr Ser Leu Thr Trp Tyr Gln Gln Lys Gln Gly Arg Ser Pro
    50                  55                  60 cag ctc ctg atc tat aat gca atc aac ttg gaa gat ggt gtc cca tcg      240
Gln Leu Leu Ile Tyr Asn Ala Ile Asn Leu Glu Asp Gly Val Pro Ser
65                  70                  75                  80 agg ttc agt ggc agt gga tct ggg aca cag ttt tct atg aag atc aac      288
Arg Phe Ser Gly Ser Gly Ser Gly Thr Gln Phe Ser Met Lys Ile Asn
                85                  90                  95 agc atg cag cct gaa gat tcc gca act tat ttc tgt aaa cag gct tat      336
Ser Met Gln Pro Glu Asp Ser Ala Thr Tyr Phe Cys Lys Gln Ala Tyr
            100                 105                 110 gac gtt cca ttc acg ttc ggc tcg ggg aca aag ttg gaa ata aaa cgg      384
Asp Val Pro Phe Thr Phe Gly Ser Gly Thr Lys Leu Glu Ile Lys Arg
        115                 120                 125 gct gat gct gca cca act gta tcc atc ttc cca cca tcc agt                426
Ala Asp Ala Ala Pro Thr Val Ser Ile Phe Pro Pro Ser Ser
    130                 135                 140

<210> SEQ ID NO 16
<211> LENGTH: 730
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(729)

<400> SEQUENCE: 16

| | | | | | | | | | | | | | | | | |
|---|---|---|---|---|---|---|---|---|---|---|---|---|---|---|---|---|
| atg | gct | tgg | gtg | tgg | acc | ttg | cta | ttc | ctg | atg | gca | gct | gcc | caa | agt | 48 |
| Met | Ala | Trp | Val | Trp | Thr | Leu | Leu | Phe | Leu | Met | Ala | Ala | Ala | Gln | Ser | |
| 1 | | | | 5 | | | | | 10 | | | | | 15 | | |
| gcc | caa | gca | cag | atc | cag | ttg | gtg | cag | tct | gga | cct | gag | ctg | aag | aag | 96 |
| Ala | Gln | Ala | Gln | Ile | Gln | Leu | Val | Gln | Ser | Gly | Pro | Glu | Leu | Lys | Lys | |
| | | 20 | | | | | 25 | | | | | 30 | | | | |
| cct | gga | gag | aca | gtc | aag | atc | tcc | tgc | aag | gct | tct | ggg | tat | acc | ttc | 144 |
| Pro | Gly | Glu | Thr | Val | Lys | Ile | Ser | Cys | Lys | Ala | Ser | Gly | Tyr | Thr | Phe | |
| | | 35 | | | | | 40 | | | | | 45 | | | | |
| aca | cac | tat | gga | atg | aac | tgg | gtg | aag | cag | gct | cca | gga | aag | ggt | tta | 192 |
| Thr | His | Tyr | Gly | Met | Asn | Trp | Val | Lys | Gln | Ala | Pro | Gly | Lys | Gly | Leu | |
| | 50 | | | | | 55 | | | | | 60 | | | | | |
| aag | tgg | atg | ggc | tgg | ata | aac | acc | tac | act | gga | gag | cca | tca | tat | gct | 240 |
| Lys | Trp | Met | Gly | Trp | Ile | Asn | Thr | Tyr | Thr | Gly | Glu | Pro | Ser | Tyr | Ala | |
| 65 | | | | | 70 | | | | | 75 | | | | | 80 | |
| gat | gac | ttc | aag | gga | cgg | ttt | gcc | ttc | tct | ttg | gaa | acc | tct | gcc | agt | 288 |
| Asp | Asp | Phe | Lys | Gly | Arg | Phe | Ala | Phe | Ser | Leu | Glu | Thr | Ser | Ala | Ser | |
| | | | | 85 | | | | | 90 | | | | | 95 | | |
| act | gcc | tat | ttg | cag | atc | aac | aac | ctc | aaa | aat | gag | gac | atg | gct | aca | 336 |
| Thr | Ala | Tyr | Leu | Gln | Ile | Asn | Asn | Leu | Lys | Asn | Glu | Asp | Met | Ala | Thr | |
| | | 100 | | | | | 105 | | | | | 110 | | | | |
| tat | ttc | tgt | gcc | agg | agg | agg | gac | tac | ggt | act | agc | cac | tgg | tac | ctc | 384 |
| Tyr | Phe | Cys | Ala | Arg | Arg | Arg | Asp | Tyr | Gly | Thr | Ser | His | Trp | Tyr | Leu | |
| | | 115 | | | | | 120 | | | | | 125 | | | | |
| gat | gtc | tgg | ggc | gca | ggg | acc | acg | gtc | acc | gtc | tcc | tca | gcc | aaa | acg | 432 |
| Asp | Val | Trp | Gly | Ala | Gly | Thr | Thr | Val | Thr | Val | Ser | Ser | Ala | Lys | Thr | |
| | 130 | | | | | 135 | | | | | 140 | | | | | |
| aca | ccc | cca | tct | gtc | tat | cca | ctg | gcc | cct | gga | tct | gct | gcc | caa | act | 480 |
| Thr | Pro | Pro | Ser | Val | Tyr | Pro | Leu | Ala | Pro | Gly | Ser | Ala | Ala | Gln | Thr | |
| 145 | | | | | 150 | | | | | 155 | | | | | 160 | |
| aac | tcc | atg | gtg | acc | ctg | gga | tgc | ctg | gtc | aag | ggc | tat | ttc | cct | gag | 528 |
| Asn | Ser | Met | Val | Thr | Leu | Gly | Cys | Leu | Val | Lys | Gly | Tyr | Phe | Pro | Glu | |
| | | | | 165 | | | | | 170 | | | | | 175 | | |
| cca | gtg | aca | gtg | acc | tgg | aac | tct | gga | tcc | ctg | tcc | agc | ggt | gtg | cac | 576 |
| Pro | Val | Thr | Val | Thr | Trp | Asn | Ser | Gly | Ser | Leu | Ser | Ser | Gly | Val | His | |
| | | | 180 | | | | | 185 | | | | | 190 | | | |
| acc | ttc | cca | gct | gtc | ctg | cag | tct | gac | ctc | tac | act | ctg | agc | agc | tca | 624 |
| Thr | Phe | Pro | Ala | Val | Leu | Gln | Ser | Asp | Leu | Tyr | Thr | Leu | Ser | Ser | Ser | |
| | | | 195 | | | | | 200 | | | | | 205 | | | |
| gtg | act | gtc | ccc | tcc | agc | acc | tgg | ccc | agc | gag | acc | gtc | acc | tgc | aac | 672 |
| Val | Thr | Val | Pro | Ser | Ser | Thr | Trp | Pro | Ser | Glu | Thr | Val | Thr | Cys | Asn | |
| | 210 | | | | | 215 | | | | | 220 | | | | | |
| gtt | gcc | cac | ccg | gcc | agc | agc | acc | aag | gtg | gac | aag | aaa | att | gga | tcc | 720 |
| Val | Ala | His | Pro | Ala | Ser | Ser | Thr | Lys | Val | Asp | Lys | Lys | Ile | Gly | Ser | |
| 225 | | | | | 230 | | | | | 235 | | | | | 240 | |
| aga | tct | gcg | g | | | | | | | | | | | | | 730 |
| Arg | Ser | Ala | | | | | | | | | | | | | | |

<210> SEQ ID NO 17
<211> LENGTH: 438
<212> TYPE: DNA
<213> ORGANISM: Artificial Sequence
<220> FEATURE:
<223> OTHER INFORMATION: Description of Artificial Sequence: Synthetic -continued

```
        polynucleotide
<220> FEATURE:
<221> NAME/KEY: CDS
<222> LOCATION: (1)..(438)

<400> SEQUENCE: 17 atg aag ttg cct gtt agg ctg ttg gtg ctg atg ttc tgg att cct gct      48
Met Lys Leu Pro Val Arg Leu Leu Val Leu Met Phe Trp Ile Pro Ala
1               5                   10                  15 tcc agc agt gat gtt ttg atg acc caa act cca ctc tcc ctg cct gtc      96
Ser Ser Ser Asp Val Leu Met Thr Gln Thr Pro Leu Ser Leu Pro Val
                20                  25                  30 agt ctt gga gat caa gcc tcc atc tct tgc aga tct agt cag agc ttt     144
Ser Leu Gly Asp Gln Ala Ser Ile Ser Cys Arg Ser Ser Gln Ser Phe
            35                  40                  45 gta cat agt aat gga aat act tat tta gaa tgg tac ctg cag aaa cca     192
Val His Ser Asn Gly Asn Thr Tyr Leu Glu Trp Tyr Leu Gln Lys Pro
        50                  55                  60 ggc cag tct cca aag ctc ctg atc tac aaa gtt tcc aac cga ttt tct     240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
                85                  90                  95 ctc aag atc agc aga gtg gag gct gag gat ctg gga ttt tat tac tgc     336
Leu Lys Ile Ser Arg Val Glu Ala Glu Asp Leu Gly Phe Tyr Tyr Cys
                100                 105                 110 ttt caa ggt tca cat gtt ccg tac acg ttc gga ggg ggg acc aag ctg     384
Phe Gln Gly Ser His Val Pro Tyr Thr Phe Gly Gly Gly Thr Lys Leu
            115                 120                 125 gaa ata aaa cgg gct gat gct gca cca act gta tcc atc ttc cca cca     432
Glu Ile Lys Arg Ala Asp Ala Ala Pro Thr Val Ser Ile Phe Pro Pro
        130                 135                 140 tcc agt                                                              438
Ser Ser
145

<210> SEQ ID NO 18
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(714)

<400> SEQUENCE: 18 atg aaa tgc agc tgg ggc atc ttc ttc ctg atg gca gtg gtt aca ggg      48
Met Lys Cys Ser Trp Gly Ile Phe Phe Leu Met Ala Val Val Thr Gly
1               5                   10                  15 gtc aat tca gag gtt cag ctg cag cag tcg ggg gca gac ctt gtg aag      96
Val Asn Ser Glu Val Gln Leu Gln Gln Ser Gly Ala Asp Leu Val Lys
                20                  25                  30 cca ggg gcc tca gtc aag ttg tcc tgc ata gtt tct gcc ttc aac att     144
Pro Gly Ala Ser Val Lys Leu Ser Cys Ile Val Ser Ala Phe Asn Ile
            35                  40                  45 gaa gac acc tat atg cac tgg gtg aag cag agg cct gaa cag ggc ctg     192
Glu Asp Thr Tyr Met His Trp Val Lys Gln Arg Pro Glu Gln Gly Leu
        50                  55                  60 gag tgg att ggg agt att gac cct gcg cat gat aat gct aaa tat gac     240
Glu Trp Ile Gly Ser Ile Asp Pro Ala His Asp Asn Ala Lys Tyr Asp
65                  70                  75                  80
```

```
ccg aag ttc cag gtc aag gcc act atc aca gca gac aca tcc tcc aat        288
Pro Lys Phe Gln Val Lys Ala Thr Ile Thr Ala Asp Thr Ser Ser Asn
                 85                  90                  95 aca gcc tac ctg cag ctc agc agc ctg aca tct gag gac act gcc gtc        336
Thr Ala Tyr Leu Gln Leu Ser Ser Leu Thr Ser Glu Asp Thr Ala Val
            100                 105                 110 tat tac tgt gct aaa tcg gat ggt ttc tac ttt gac tcc tgg ggc caa        384
Tyr Tyr Cys Ala Lys Ser Asp Gly Phe Tyr Phe Asp Ser Trp Gly Gln
        115                 120                 125 ggc acc act ctc aca gtc tcc tca gcc aaa acg aca ccc cca tct gtc        432
Gly Thr Thr Leu Thr Val Ser Ser Ala Lys Thr Thr Pro Pro Ser Val
    130                 135                 140 tat cca ctg gcc cct gga tct gct gcc caa act aac tcc atg gtg acc        480
Tyr Pro Leu Ala Pro Gly Ser Ala Ala Gln Thr Asn Ser Met Val Thr
145                 150                 155                 160 ctg gga tgc ctg gtc aag ggc tat ttc cct gag cca gtg aca gtg acc        528
Leu Gly Cys Leu Val Lys Gly Tyr Phe Pro Glu Pro Val Thr Val Thr
                165                 170                 175 tgg aac tct gga tcc ctg tcc agc ggt gtg cac acc ttc cca gct gtc        576
Trp Asn Ser Gly Ser Leu Ser Ser Gly Val His Thr Phe Pro Ala Val
            180                 185                 190 ctg cag tct gac ctc tac act ctg agc agc tca gtg act gtc ccc tcc        624
Leu Gln Ser Asp Leu Tyr Thr Leu Ser Ser Ser Val Thr Val Pro Ser
        195                 200                 205 agc acc tgg ccc agc gag acc gtc acc tgc aac gtt gcc cac ccg gcc        672
Ser Thr Trp Pro Ser Glu Thr Val Thr Cys Asn Val Ala His Pro Ala
    210                 215                 220 agc agc acc aag gtg gac aag aaa att gga tcc aga tct gcg                714
Ser Ser Thr Lys Val Asp Lys Lys Ile Gly Ser Arg Ser Ala
225                 230                 235

<210> SEQ ID NO 19
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(438)

<400> SEQUENCE: 19 atg ggc ttc aag atg gag tca cag atc cag gtc ttt gta ttc gtg ttg         48
Met Gly Phe Lys Met Glu Ser Gln Ile Gln Val Phe Val Phe Val Leu
1               5                   10                  15 ctc tgg ttg tct gga att gat ggt gac att gtg atg acc cag tct caa         96
Leu Trp Leu Ser Gly Ile Asp Gly Asp Ile Val Met Thr Gln Ser Gln
            20                  25                  30 aaa ttc atg tcc aca tca gta gga gac agg gtc agc atc acc tgc aag        144
Lys Phe Met Ser Thr Ser Val Gly Asp Arg Val Ser Ile Thr Cys Lys
        35                  40                  45 gcc agc cag aat gtt cgc tct gct gtg gcc tgg tat caa cag aaa cca        192
Ala Ser Gln Asn Val Arg Ser Ala Val Ala Trp Tyr Gln Gln Lys Pro
    50                  55                  60 ggg cag tct cct aaa gca ttg att tac ttg gca tcc aac cgg cac act        240
Gly Gln Ser Pro Lys Ala Leu Ile Tyr Leu Ala Ser Asn Arg His Thr
65                  70                  75                  80 gga gtc cct gat cgc ttc aca ggc agt gga tct ggg aca gat ttc act        288
Gly Val Pro Asp Arg Phe Thr Gly Ser Gly Ser Gly Thr Asp Phe Thr
                85                  90                  95 ctc acc att agc aat gtg caa tct gag gac ctg gca gat tat ttc tgt        336
Leu Thr Ile Ser Asn Val Gln Ser Glu Asp Leu Ala Asp Tyr Phe Cys
```

```
Leu Thr Ile Ser Asn Val Gln Ser Glu Asp Leu Ala Asp Tyr Phe Cys
                100                 105                 110 ctg caa cat tgg aat tat cct cta tcg gtc gga ggg ggg acc aag ctg        384
Leu Gln His Trp Asn Tyr Pro Leu Ser Val Gly Gly Gly Thr Lys Leu
        115                 120                 125 gaa ata aaa cgg gct gat gct gca cca act gta tcc atc ttc cca cca        432
Glu Ile Lys Arg Ala Asp Ala Ala Pro Thr Val Ser Ile Phe Pro Pro
    130                 135                 140 tcc agt                                                                 438
Ser Ser <210> SEQ ID NO 20
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(456)

<400> SEQUENCE: 20 atg gct gtc ttg ggg ctg ctc ttc tgc ctg gtt gca ttt cca agc tgt         48
Met Ala Val Leu Gly Leu Leu Phe Cys Leu Val Ala Phe Pro Ser Cys
1               5                   10                  15 gtc ctg tcc cag gtg cag ctg aag gag tca gga cct ggc ctg gtg gcg         96
Val Leu Ser Gln Val Gln Leu Lys Glu Ser Gly Pro Gly Leu Val Ala
            20                  25                  30 ccc tca cag agt ctg tcc atc act tgc act gtc tct ggg ttt tca tta        144
Pro Ser Gln Ser Leu Ser Ile Thr Cys Thr Val Ser Gly Phe Ser Leu
        35                  40                  45 acc agc tat ggt gta cag tgg gtt cgc cag cct cca gga aag ggt ctg        192
Thr Ser Tyr Gly Val Gln Trp Val Arg Gln Pro Pro Gly Lys Gly Leu
    50                  55                  60 gag tgg ctg gga gta ata tgg gct ggt gga agc aca aaa tat aat tcg        240
Glu Trp Leu Gly Val Ile Trp Ala Gly Gly Ser Thr Lys Tyr Asn Ser
65                  70                  75                  80 gct ctc atg tcc aga ctg agc atc agc aaa gac aac tcc aag agc caa        288
Ala Leu Met Ser Arg Leu Ser Ile Ser Lys Asp Asn Ser Lys Ser Gln
                85                  90                  95 gtt ttc tta aaa atg aac agt ctg caa act gat gac aca gcc atg tac        336
Val Phe Leu Lys Met Asn Ser Leu Gln Thr Asp Asp Thr Ala Met Tyr
            100                 105                 110 tac tgt gcc aga gat gat tac tac cgt cgt acc tcc ctc tat gct atg        384
Tyr Cys Ala Arg Asp Asp Tyr Tyr Arg Arg Thr Ser Leu Tyr Ala Met
        115                 120                 125 gac tac tgg ggt caa gga acc tca gtc acc gtc tcc tca gcc aaa aca        432
Asp Tyr Trp Gly Gln Gly Thr Ser Val Thr Val Ser Ser Ala Lys Thr
    130                 135                 140 aca ccc cca tca gtc tat cca ctg                                        456
Thr Pro Pro Ser Val Tyr Pro Leu
145                 150

<210> SEQ ID NO 21
<211> LENGTH: 437
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(435)
```

-continued

```
<400> SEQUENCE: 21 atg aag ttg cct gtt agg ctg ttg gtg ctg atg ttc tgg att cct gct        48
Met Lys Leu Pro Val Arg Leu Leu Val Leu Met Phe Trp Ile Pro Ala
1               5                   10                  15 tcc agc agt gat gtt ttg atg acc caa act cca ctc tcc ctg cct gtc        96
Ser Ser Ser Asp Val Leu Met Thr Gln Thr Pro Leu Ser Leu Pro Val
            20                  25                  30 agt ctt gga gat caa gcc tcc atc tct tgc aga tct agt cag agc ctt       144
Ser Leu Gly Asp Gln Ala Ser Ile Ser Cys Arg Ser Ser Gln Ser Leu
        35                  40                  45 gta cac agt aat gga aac acc tat tta cat tgg tac ctg cag aag cca       192
Val His Ser Asn Gly Asn Thr Tyr Leu His Trp Tyr Leu Gln Lys Pro
    50                  55                  60 ggc cag tct cca aag ctc ctg atc tac aaa gtt tcc aac cga ttt tct       240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg aca gat ttc aca       288
Gly Val Pro Asp Arg Phe Ser Gly Ser Gly Ser Gly Thr Asp Phe Thr
                85                  90                  95 ctc aag atc agc aga gtg gag gct gag gat ctg gga gtt tat ttc tgc       336
Leu Lys Ile Ser Arg Val Glu Ala Glu Asp Leu Gly Val Tyr Phe Cys
            100                 105                 110 tct caa agt aca cat gtt ccg tac acg ttc gga ggg ggg acc aag ctg       384
Ser Gln Ser Thr His Val Pro Tyr Thr Phe Gly Gly Gly Thr Lys Leu
        115                 120                 125 gaa ata aaa cgg gct gat gct gca cca act gta tcc atc ttc cca cca       432
Glu Ile Lys Arg Ala Asp Ala Ala Pro Thr Val Ser Ile Phe Pro Pro
    130                 135                 140 tcc ag                                                                 437
Ser
145

<210> SEQ ID NO 22
<211> LENGTH: 24
<212> TYPE: PRT
<213> ORGANISM: Homo sapiens

<400> SEQUENCE: 22

Gly Thr Pro Cys Leu Leu Gly Pro Gly Pro Val Leu Thr Val Leu Ala
1               5                   10                  15

Leu Leu Leu Ala Ser Thr Leu Ala
            20

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cggaattcgc cgccaccatg gccttgccaa cggctcgacc cctgttg                    47

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
```

-continued gctctagaga tggttccgtt caggctgccg ccaggatgg         39

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaatttccca agcttgtgga gaagacagcc tgtccttcag gcaag         45

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aaggaaaaaa gcggccgcgc cctgtagccc cagccccagc gtgtccag         48

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctctagaga tggtccgttc aggctgccgc caggatgg         38

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(18)
<223> OTHER INFORMATION: May or may not be present

<400> SEQUENCE: 28
tttttttttt tttttttt         18

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgggatgga gcggggtctt tctctt         26

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 30
cagtggatag acagatgggg g                                              21

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atgagtgtgc tcactcaggt cctggcgttg                                     30

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
actggatggt gggaagatgg                                                20

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atggcttggg tgtggacctt gctattcctg                                     30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atgaagttgc ctgttaggct gttggtgctg                                     30

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgaaatgca gctggggcat cttcttc                                        27

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
```

```
atgggcttca agatggagtc acagatccag g                                 31

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atggctgtct tggggctgct cttctgc                                      27

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagtggatag actgatgggg g                                            21
```